US010526336B2

(12) United States Patent
Kuduk et al.

(10) Patent No.: US 10,526,336 B2
(45) Date of Patent: Jan. 7, 2020

(54) FUSED HETEROARYL DERIVATIVES AS OREXIN RECEPTOR ANTAGONISTS

(71) Applicant: Merck Sharp & Dohme Corp., Rahway, NJ (US)

(72) Inventors: Scott D. Kuduk, Harleysville, PA (US); Nigel Liverton, Harleysville, PA (US); Douglas C. Beshore, Lower Gwynedd, PA (US); Na Meng, Shanghai (CN); Yunfu Luo, Shanghai (CN)

(73) Assignee: Merck, Sharp & Dohme Corp., Rahway, NJ (US)

( * ) Notice: Subject to any disclaimer, the term of this patent is extended or adjusted under 35 U.S.C. 154(b) by 114 days.

(21) Appl. No.: 15/535,315

(22) PCT Filed: Dec. 18, 2015

(86) PCT No.: PCT/US2015/066548
§ 371 (c)(1),
(2) Date: Jun. 12, 2017

(87) PCT Pub. No.: WO2016/106106
PCT Pub. Date: Jun. 30, 2016

(65) Prior Publication Data
US 2018/0370973 A1  Dec. 27, 2018

(30) Foreign Application Priority Data

Dec. 23, 2014 (WO) .............. PCT/CN21014/094592

(51) Int. Cl.
A61K 31/519 (2006.01)
A61K 31/4545 (2006.01)
A61K 31/4985 (2006.01)
C07D 487/04 (2006.01)
A61K 45/06 (2006.01)
C07D 471/04 (2006.01)
C07D 498/02 (2006.01)
C07D 498/04 (2006.01)

(52) U.S. Cl.
CPC ............ *C07D 487/04* (2013.01); *A61K 45/06* (2013.01); *C07D 471/04* (2013.01); *C07D 498/02* (2013.01); *C07D 498/04* (2013.01)

(58) Field of Classification Search
None
See application file for complete search history.

(56) References Cited

U.S. PATENT DOCUMENTS

| 7,951,797 | B2 | 5/2011 | Breslin et al. |
|---|---|---|---|
| 8,242,121 | B2 | 8/2012 | Coleman et al. |
| 8,263,586 | B2 | 9/2012 | Cox et al. |
| 8,349,872 | B2 | 1/2013 | Coleman et al. |
| 8,357,700 | B2 | 1/2013 | Cox et al. |
| 8,357,709 | B2 | 1/2013 | Coleman et al. |
| 8,362,009 | B2 | 1/2013 | Bergman et al. |
| 8,399,494 | B2 | 3/2013 | Bergman et al. |
| 8,466,281 | B2 | 6/2013 | Coleman et al. |
| 8,618,102 | B2 | 12/2013 | Coleman et al. |
| 8,623,863 | B2 | 1/2014 | Coleman et al. |
| 8,669,272 | B2 | 3/2014 | Breslin et al. |
| 8,685,961 | B2 | 4/2014 | Brashear et al. |
| 8,710,076 | B2 | 4/2014 | Breslin et al. |
| 8,940,898 | B2 | 1/2015 | Kuduk et al. |
| 9,029,364 | B2 | 5/2015 | Kuduk et al. |
| 9,156,819 | B2 | 10/2015 | Kuduk et al. |
| 9,546,152 | B2 | 1/2017 | Kuduk et al. |
| 9,550,786 | B2 | 1/2017 | Cooke et al. |
| 9,556,145 | B2 | 1/2017 | Kuduk et al. |
| 9,556,190 | B2 | 1/2017 | Kuduk et al. |
| 9,586,934 | B2 | 3/2017 | Kuduk et al. |
| 9,586,950 | B2 | 3/2017 | Kuduk et al. |
| 9,617,246 | B2 | 4/2017 | Kuduk et al. |
| 9,624,197 | B2 | 4/2017 | Kuduk et al. |
| 2010/0029736 | A1 | 2/2010 | Cox et al. |
| 2011/0195957 | A1 | 8/2011 | Bergman et al. |
| 2011/0201632 | A1 | 8/2011 | Breslin et al. |
| 2011/0288098 | A1 | 11/2011 | Alvaro et al. |
| 2012/0196901 | A1 | 8/2012 | Coleman et al. |
| 2015/0322039 | A1 | 11/2015 | Kuduk et al. |
| 2015/0322040 | A1 | 11/2015 | Kuduk et al. |
| 2015/0322041 | A1 | 11/2015 | Kuduk et al. |
| 2016/0016935 | A1 | 1/2016 | Kuduk et al. |
| 2016/0068510 | A1 | 3/2016 | Kuduk et al. |
| 2016/0068514 | A1 | 3/2016 | Kuduk et al. |
| 2016/0102073 | A1 | 4/2016 | Kuduk et al. |
| 2016/0176858 | A1 | 6/2016 | Liverton et al. |

(Continued)

FOREIGN PATENT DOCUMENTS

| WO | 2004026866 | 4/2004 |
|---|---|---|
| WO | 2010048010 | 4/2010 |

(Continued)

OTHER PUBLICATIONS

Roecker, et al., Orexin Receptor Antagonists: New Therapeutic Agents for the Treatment of Insomnia, Journal of Medicinal Chemistry, 2016, 504-530, 59(2).

(Continued)

*Primary Examiner* — Samantha L Shterengarts
(74) *Attorney, Agent, or Firm* — J. Eric Thies; John C. Todaro

(57) ABSTRACT

The present invention is directed to fused heteroaryl derivative compounds which are antagonists of orexin receptors. The present invention is also directed to uses of the compounds described herein in the potential treatment or prevention of neurological and psychiatric disorders and diseases in which orexin receptors are involved. The present invention is also directed to pharmaceutical compositions comprising these compounds. The present invention is also directed to uses of these pharmaceutical compositions in the prevention or treatment of such diseases in which orexin receptors are involved.

9 Claims, No Drawings

(56) References Cited

U.S. PATENT DOCUMENTS

| | | |
|---|---|---|
| 2016/0185768 A1 | 6/2016 | Liverton et al. |
| 2016/0304490 A1 | 10/2016 | Kuduk et al. |
| 2016/0318900 A1 | 11/2016 | Kuduk et al. |
| 2016/0318923 A1 | 11/2016 | Kuduk et al. |

FOREIGN PATENT DOCUMENTS

| | | |
|---|---|---|
| WO | 2010048012 | 4/2010 |
| WO | 2010048016 | 4/2010 |
| WO | 2014099698 | 6/2014 |
| WO | 2014113303 | 7/2014 |
| WO | 2014176142 | 10/2014 |
| WO | 2016069510 | 5/2016 |
| WO | 2016069512 | 5/2016 |
| WO | 2016069515 | 5/2016 |
| WO | 2016069517 | 5/2016 |
| WO | 2016069519 | 5/2016 |
| WO | 2016085783 | 6/2016 |
| WO | 2016085784 | 6/2016 |
| WO | 2016089721 | 6/2016 |
| WO | 2016089722 | 6/2016 |
| WO | 2016100154 | 6/2016 |
| WO | 2016100156 | 6/2016 |
| WO | 2016100157 | 6/2016 |
| WO | 2016100161 | 6/2016 |
| WO | 2016100162 | 6/2016 |
| WO | 2016106105 | 6/2016 |
| WO | 2016106106 | 6/2016 |

OTHER PUBLICATIONS

Skudlarek, et al., Investigation of orexin-2 selective receptor antagonists: Structural modifications resulting in dual orexin receptor antagonists, Bioorganic & Medicinal Chemistry Letters, 2017, 1364-1370, 27(6).

Malherbe, et al., Mapping the Bindign Pocket of Dual Antagonist Almorexant to Human Orexin 1 and Orexin 2 Receptors:: . . . , Molecular Pharmacology, 2010, pp. 81-96, 78.

FUSED HETEROARYL DERIVATIVES AS OREXIN RECEPTOR ANTAGONISTS

CROSS REFERENCE TO RELATED APPLICATIONS

This application is a U.S. National Phase application under 35 U.S.C. § 371 of PCT Application No. PCT/US2015/066548, filed Dec. 18, 2015, which claims priority from PCT Application No. PCT/CN2014/094592, filed Dec. 23, 2014.

BACKGROUND OF THE INVENTION

The orexins (hypocretins) comprise two neuropeptides produced in the hypothalamus: orexin A (OX-A) (a 33 amino acid peptide) and orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behavior (Sakurai T. et al., Cell, 1998, 92, 573-585). Orexins regulate states of sleep and wakefulness opening potentially novel therapeutic approaches for narcoleptic or insomniac patients (Chemelli R. M. et al., Cell, 1999, 98, 437-451). Orexins have also been indicated as playing a role in arousal, reward, learning and memory (Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A, and the orexin-2 receptor (OX2 or OX2R) is capable of binding OX-A as well as OX-B. The physiological actions in which orexins are presumed to participate are thought to be expressed via one or both of OX1 receptor and OX2 receptor as the two subtypes of orexin receptors.

SUMMARY OF THE INVENTION

The present invention is directed to fused heteroaryl derivative compounds which are antagonists of orexin receptors. The present invention is also directed to uses of the compounds described herein in the potential treatment or prevention of neurological and psychiatric disorders and diseases in which orexin receptors are involved. The present invention is also directed to pharmaceutical compositions comprising these compounds. The present invention is also directed to uses of these pharmaceutical compositions in the prevention or treatment of such diseases in which orexin receptors are involved.

DETAILED DESCRIPTION OF THE INVENTION

The present invention is directed to compounds of the formula I:

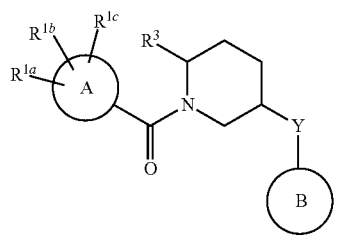

I wherein:
A is selected from the group consisting of phenyl, naphthyl and heteroaryl;
B is selected from the group consisting of:

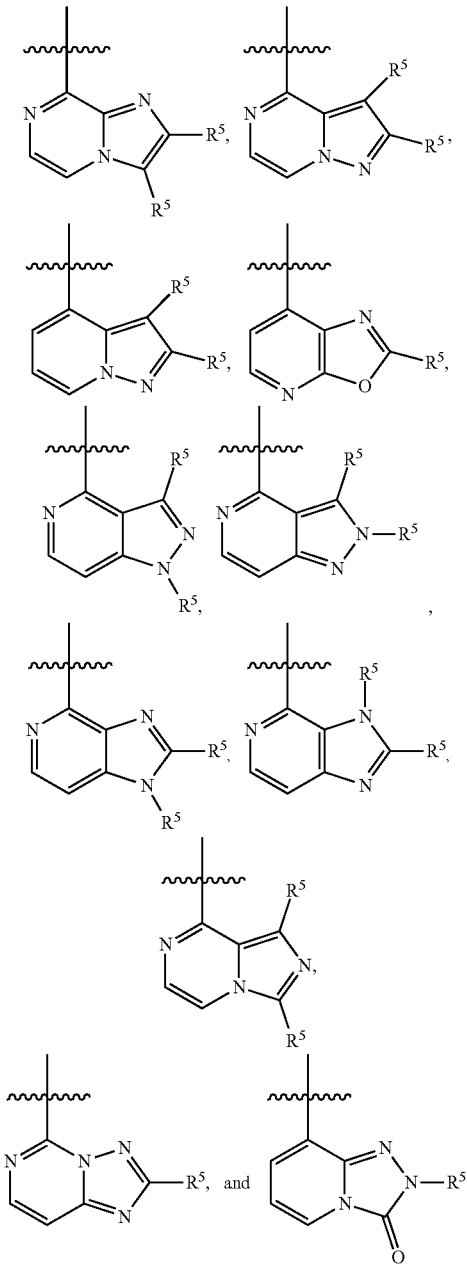

Y is O, S or NH;
$R^{1a}$, $R^{1b}$ and $R^{1c}$ are independently selected from the group consisting of:
(1) hydrogen,
(2) halogen,
(3) hydroxyl,
(4) $-(CH_2)_s-(C=O)_m-O_n-C_{1-6}$alkyl, and where the alkyl is unsubstituted or substituted with one or more substituents selected from $R^4$,
(5) $-(CH_2)_s-(C=O)_m-O_n-C_{3-6}$cycloalkyl, where the cycloalkyl is unsubstituted or substituted with one or more substituents selected from $R^4$, (6) —(CH$_2$)$_s$—(C=O)$_m$—C$_{2-4}$alkenyl, where the alkenyl is unsubstituted or substituted with one or more substituents selected from R$^4$,
(7) —(CH$_2$)$_s$—(C=O)$_m$—C$_{2-4}$alkynyl, where the alkynyl is unsubstituted or substituted with one or more substituents selected from R$^4$,
(8) —(CH$_2$)$_s$—(C=O)$_m$—O$_n$-phenyl or —(CH$_2$)$_s$—(C=O)$_m$—O$_n$-naphthyl, where the phenyl or naphthyl is unsubstituted or substituted with one or more substituents selected from R$^4$,
(9) —(CH$_2$)$_s$—(C=O)$_m$—O$_n$—X, wherein X is heterocyclyl or heteroaryl, wherein the heterocyclyl or heteroaryl is unsubstituted or substituted with one or more substituents selected from R$^4$,
(10) —(CH$_2$)$_s$—(C=O)$_m$—NR$^{10}$R$^{11}$,
(11) —(CH$_2$)$_s$—S(O)$_2$—NR$^{10}$R$^{11}$,
(12) —(CH$_2$)$_s$—S(O)$_q$—R$^{12}$, where q is 0, 1 or 2 and where R$^{12}$ is selected from the definitions of R$^{10}$ and R$^{11}$,
(13) —CO$_2$H,
(14) —CN, and
(15) —NO$_2$;
where m is 0 or 1, n is 0 or 1 (wherein if m is 0 or n is 0, a bond is present);
is independently 0, 1, 2 or 3;
R$^3$ is selected from hydrogen, C$_{1-6}$alkyl and C$_{3-6}$cycloalkyl, wherein the alkyl or cycloalkyl is unsubstituted or substituted with one or more substituents selected from R$^4$;
R$^4$ is independently selected from the group consisting of:
  (1) hydroxyl,
  (2) halogen,
  (3) C$_{1-6}$alkyl,
  (4) —C$_{3-6}$cycloalkyl,
  (5) —O—C$_{1-6}$alkyl,
  (6) —O(C=O)—C$_{1-6}$alkyl,
  (7) —NH$_2$,
  (7) —NH—C$_{1-6}$alkyl,
  (8) —NO$_2$,
  (9) phenyl,
  (10) heterocyclyl,
  (11) —CO$_2$H, and
  (12) —CN;
R$^5$ is independently selected from the group consisting of: hydrogen, halogen, OH, NH$_2$, CN, C$_1$-C$_6$alkylOR$^6$, —O(C=O)—C$_{1-6}$alkyl, —(C=O)—NR$^6{}_2$, C$_{1-6}$alkyl, C$_{1-6}$alkenyl, C$_3$-C$_8$cycloalkyl, wherein the alkyl, alkenyl or cycloalkyl is optionally substituted with one or more moieties selected from the group consisting of halogen, OH and NH$_2$;
R$^6$ is independently hydrogen or C$_{1-6}$alkyl;
R$^{10}$ and R$^{11}$ are independently selected from the group consisting of:
  (a) hydrogen,
  (b) C$_{1-6}$alkyl, which is unsubstituted or substituted with R$^4$,
  (c) C$_{3-6}$alkenyl, which is unsubstituted or substituted with R$^4$,
  (d) C$_{3-6}$alkynyl, which is unsubstituted or substituted with R$^4$,
  (e) C$_{3-6}$cycloalkyl which is unsubstituted or substituted with R$^4$,
  (f) phenyl, which is unsubstituted or substituted with R$^4$, and
  (g) heterocyclyl, which is unsubstituted or substituted with R$^4$,
or a pharmaceutically acceptable salt thereof.

An embodiment of the present invention is directed to compounds of Formula Ia,

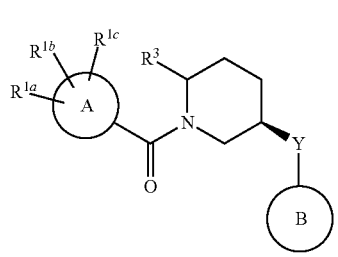

wherein:
A is selected from the group consisting of phenyl, thienyl, pyridyl and pyrimidinyl;
Y is O, S or NH;
R$^{1a}$ and R$^{1b}$ are both H, R$^{1c}$ is selected from the group consisting of:
  (1) hydrogen,
  (2) halogen,
  (3) hydroxyl,
  (4) —(CH$_2$)$_s$—(C=O)$_m$—O$_n$—C$_{1-6}$alkyl, and where the alkyl is unsubstituted or substituted with one or more substituents selected from R$^4$,
  (5) —(CH$_2$)$_s$—O$_n$—C$_{3-6}$cycloalkyl, where the cycloalkyl is unsubstituted or substituted with one or more substituents selected from R$^4$,
  (6) -phenyl, where the phenyl is unsubstituted or substituted with one or more substituents selected from R$^4$,
  (7) -heteroaryl selected from the group consisting of triazolyl, pyrimidinyl, tetrazolyl, pyrazolyl and pyridinyl, where the heteroaryl is unsubstituted or substituted with one or more substituents selected from R$^4$,
  (8) —(CH$_2$)$_s$—S(O)$_q$—R$^{12}$, where q is 0, 1 or 2 and where R$^{12}$ is selected from
    (a) C$_{1-6}$alkyl, which is unsubstituted or substituted with R$^4$,
    (b) C$_{3-6}$alkenyl, which is unsubstituted or substituted with R$^4$,
    (c) C$_{3-6}$alkynyl, which is unsubstituted or substituted with R$^4$,
  n is 0 or 1, m is 0 or 1, (wherein if m is 0 or n is 0, a bond is present)
  s is independently 0, 1, 2 or 3;
R$^3$ is selected from hydrogen or C$_{1-6}$alkyl, which is unsubstituted or substituted with one or more substituents selected from R$^4$;
R$^4$ is independently selected from the group consisting of:
  (1) hydroxyl,
  (2) halogen,
  (3) C$_{1-6}$alkyl,
  (4) —NH$_2$,
  (5) —NH—C$_{1-6}$alkyl,
  (6) —NO$_2$, and
  (7) —CN;
R$^5$ is independently selected from the group consisting of: hydrogen, halogen, OH, NH$_2$, CN, C$_1$-C$_6$alkylOR$^6$, C$_{1-6}$alkyl, wherein the alkyl is optionally substituted with one or more moieties selected from the group consisting of halogen, OH and NH$_2$;
R$^6$ is hydrogen or C$_{1-6}$alkyl;
or a pharmaceutically acceptable salt thereof.
A further embodiment of the present invention is directed to compounds of the formula Ib:

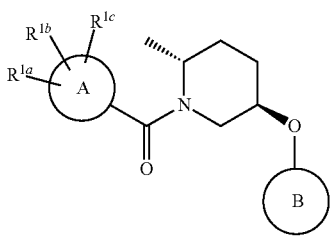

wherein A, B, $R^{1a}$, $R^{1b}$, and $R^{1c}$ are defined herein.

In one aspect of the foregoing embodiments, B is

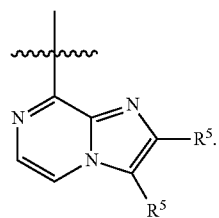

In another embodiment, B is

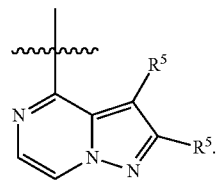

In one aspect of the foregoing embodiments, $R^{1a}$ and $R^{1b}$ are both H, $R^{1c}$ is heteroaryl selected from the group consisting of triazolyl, pyrimidinyl, tetrazolyl, pyrazolyl and pyridinyl. In another embodiment, $R^{1c}$ is $C_{1-6}$alkyl optionally substituted with halogen. In a further embodiment, $R^{1c}$ is phenyl. In yet a further embodiment, $R^{1c}$ is —(CH$_2$)$_s$—S(O)$_2$—C$_{1-6}$alkyl, and s is 0, 1 or 2.

In one aspect of the foregoing embodiments, $R^3$ is $C_{1-6}$alkyl. In another aspect of the foregoing embodiments, $R^3$ is methyl.

In another aspect of the foregoing embodiments, $R^5$ is selected from the group consisting of: halogen, CN, methyl, fluoro-methyl, difluoro-methyl, and trifluoro-methyl. In another aspect of the foregoing embodiments, $R^5$ is methyl.

In one aspect of the foregoing embodiments, A is selected from phenyl, pyridyl, thienyl and pyrimidinyl. In another aspect of the foregoing embodiments, A is phenyl. In another aspect of the foregoing embodiments, A is pyridyl. In a further aspect of the foregoing embodiments, A is thienyl. In a further aspect of the foregoing embodiments, A is pyrimidinyl.

Certain embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

Compounds of Formula I, and salts, solvates thereof, may exist in their tautomeric form (for example, as an amide or imino ether). All such tautomeric forms are contemplated herein as part of the present invention.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents. The term "cycloalkyl" means a monocyclic, bicyclic saturated aliphatic hydrocarbon group having the specified number of carbon atoms. The cycloalkyl may be fused with an aryl group such as phenyl, and it is understood that the cycloalkyl substituent is attached via the cycloalkyl group. For example, "cycloalkyl" includes cyclopropyl, methyl-cyclopropyl, 2,2-dimethyl-cyclobutyl, 2-ethyl-cyclopentyl, cyclohexyl, and so on.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

The term "heteroaryl" as used herein represents a stable monocyclic, bicyclic or tricyclic ring of up to 7 atoms in each ring, wherein at least one ring is aromatic and contains carbon and from 1 to 4 heteroatoms selected from the group consisting of O, N and S. In another embodiment, the term heteroaryl refers to a monocyclic, bicyclic or tricyclic aromatic ring of 5- to 14-ring atoms of carbon and from one to four heteroatoms selected from O, N, or S. As with the definition of heterocyclyl below, "heteroaryl" is also understood to include the N-oxide derivative of any nitrogen-containing heteroaryl. In cases where the heteroaryl substituent is bicyclic and one ring is non-aromatic or contains no heteroatoms, in one embodiment, the attachment is via the heteroatom containing aromatic ring, respectively. Examples of heteroaryl include but are not limited to benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, imidazolyl, indolinyl, indolyl, dihydroindolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydroquinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

"Heterocyclyl" means a non-aromatic saturated monocyclic, bicyclic, tricyclic or spirocyclic ring system comprising up to 7 atoms in each ring, or contains 3 to 14, or 5 to 10 ring atoms, in which one or more of the atoms in the ring system is an element other than carbon, for example, nitrogen, oxygen, phosphor or sulfur, alone or in combination. There are no adjacent oxygen and/or sulfur atoms present in the ring system. In one embodiment, the heterocyclyls contain about 5 to about 6 ring atoms. The heterocyclyl may be fused with an aromatic aryl group such as phenyl or heterocyclenyl. The heterocyclyl is optionally bridged (i.e., forming a bicyclic moiety), for example with a methylene, ethylene or propylene bridge. The prefix aza, oxa or thia before the heterocyclyl root name means that at least a nitrogen, oxygen or sulfur atom, respectively, is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom.

Attachment of a heterocyclyl substituent can occur via a carbon atom or via a heteroatom. In cases where the heterocyclyl substituent is bicyclic and one ring is aromatic, unsaturated and/or contains no heteroatoms, in one embodiment, the attachment is via the heteroatom containing non-aromatic saturated ring.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Examples of isotopes suitable for inclusion in the compounds of the invention include isotopes of hydrogen such as $^2H$ and $^3H$, carbon such as $^{11}C$, $^{13}C$ and $^{14}C$, nitrogen such as $^{13}N$ and $^{15}N$, oxygen such as $^{15}O$, $^{17}O$ and $^{18}O$, phosphorus such as $^{32}P$, sulfur such as $^{35}S$, fluorine such as $^{18}F$, iodine such as $^{123}I$ and $^{125}I$, and chlorine such as $^{36}Cl$. Certain isotopically-labelled compounds of Formula I, for example those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labelled compounds of Formula I can generally be prepared by conventional techniques known to those skilled in the art or by processes analogous to those described in the accompanying Examples using appropriate isotopically-labelled reagents in place of the non-labelled reagent previously employed.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which is selected from the group consisting of:
(2-(2H-1,2,3-triazol-2-yl)phenyl)((2R,5R)-5-(imidazo[1,2-a]pyrazin-8-yloxy)-2-methylpiperidin-1-yl)methanone;
((2R,5R)-5-(imidazo[1,2-a]pyrazin-8-yloxy)-2-methylpiperidin-1-yl)(2-((methylsulfonyl)methyl)phenyl)methanone;

((2R,5R)-5-(imidazo[1,2-a]pyrazin-8-yloxy)-2-methylpiperidin-1-yl)(2-(2,2,2-trifluoroethyl)phenyl)methanone;

((2R,5R)-5-(imidazo[1,2-a]pyrazin-8-yloxy)-2-methylpiperidin-1-yl)(2-propylphenyl)methanone;

(2-(2H-1,2,3-triazol-2-yl)phenyl)((2R,5R)-5-(imidazo[1,2-a]pyrazin-8-ylthio)-2-methylpiperidin-1-yl)methanone;

(2-(2H-1,2,3-triazol-2-yl)phenyl)((2R,5R)-2-methyl-5-((2-methylimidazo[1,2-a]pyrazin-8-yl)oxy)piperidin-1-yl)methanone;

(2-(2H-1,2,3-triazol-2-yl)thiophen-3-yl)((2R,5R)-2-methyl-5-((2-methylimidazo[1,2-a]pyrazin-8-yl)oxy)piperidin-1-yl)methanone;

(4-(2H-1,2,3-triazol-2-yl)thiophen-3-yl)((2R,5R)-2-methyl-5-((2-methylimidazo[1,2-a]pyrazin-8-yl)oxy)piperidin-1-yl)methanone;

1-(2-((2R,5R)-2-methyl-5-((2-methylimidazo[1,2-a]pyrazin-8-yl)oxy)piperidine-1-carbonyl)phenyl)cyclopropanecarbonitrile;

(4-fluoro-2-(2H-1,2,3-triazol-2-yl)phenyl)((2R,5R)-2-methyl-5-((2-methylimidazo[1,2-a]pyrazin-8-yl)oxy)piperidin-1-yl)methanone;

(2-(2H-tetrazol-2-yl)phenyl)((2R,5R)-2-methyl-5-((2-methylimidazo[1,2-a]pyrazin-8-yl)oxy)piperidin-1-yl)methanone;

((2R,5R)-2-methyl-5-((2-methylimidazo[1,2-a]pyrazin-8-yl)oxy)piperidin-1-yl)(2-((methylsulfonyl)methyl)phenyl)methanone;

((2R,5R)-2-methyl-5-((2-methylimidazo[1,2-a]pyrazin-8-yl)oxy)piperidin-1-yl)(4-(pyrimidin-2-yl)thiophen-3-yl)methanone;

((2R,5R)-2-methyl-5-((2-methylimidazo[1,2-a]pyrazin-8-yl)oxy)piperidin-1-yl)(2-(pyrimidin-2-yl)thiophen-3-yl)methanone;

(2-(2,2-difluoroethoxy)pyridin-3-yl)((2R,5R)-2-methyl-5-((2-methylimidazo[1,2-a]pyrazin-8-yl)oxy)piperidin-1-yl)methanone;

((2R,5R)-2-methyl-5-((2-methylimidazo[1,2-a]pyrazin-8-yl)oxy)piperidin-1-yl)(2-(2,2,2-trifluoroethoxy)pyridin-3-yl)methanone;

((2R,5R)-2-methyl-5-((2-methylimidazo[1,2-a]pyrazin-8-yl)oxy)piperidin-1-yl)(2-phenylpyridin-3-yl)methanone;

(2-(1H-pyrazol-1-yl)pyridin-3-yl)((2R,5R)-2-methyl-5-((2-methylimidazo[1,2-a]pyrazin-8-yl)oxy)piperidin-1-yl)methanone;

(2-(2H-1,2,3-triazol-2-yl)phenyl)((2R,5R)-2-methyl-5-((2-methylimidazo[1,2-a]pyrazin-8-yl)amino)piperidin-1-yl)methanone;

(2-(2H-1,2,3-triazol-2-yl)phenyl)((2R,5R)-5-((2-isopropylimidazo[1,2-a]pyrazin-8-yl)oxy)-2-methylpiperidin-1-yl)methanone;

(2-(2H-1,2,3-triazol-2-yl)phenyl)((2R,5R)-2-methyl-5-((2-(trifluoromethyl)imidazo[1,2-a]pyrazin-8-yl)oxy)piperidin-1-yl)methanone;

(2-(2H-1,2,3-triazol-2-yl)phenyl)((2R,5R)-2-methyl-5-((2-(trifluoromethyl)imidazo[1,2-a]pyrazin-8-yl)amino)piperidin-1-yl)methanone;

(2-(2H-1,2,3-triazol-2-yl)thiophen-3-yl)((2R,5R)-2-methyl-5-((2-(trifluoromethyl)imidazo[1,2-a]pyrazin-8-yl)amino)piperidin-1-yl)methanone;

8-(((3R,6R)-1-(2-(2H-1,2,3-triazol-2-yl)benzoyl)-6-methylpiperidin-3-yl)oxy)imidazo[1,2-a]pyrazine-2-carbonitrile;

(2-(2H-1,2,3-triazol-2-yl)phenyl)((2R,5R)-5-((2-(hydroxymethyl)imidazo[1,2-a]pyrazin-8-yl)oxy)-2-methylpiperidin-1-yl)methanone;

(2-(2H-1,2,3-triazol-2-yl)phenyl)((2R,5R)-5-((3-chloroimidazo[1,2-a]pyrazin-8-yl)oxy)-2-methylpiperidin-1-yl)methanone;

(2-(2H-tetrazol-2-yl)phenyl)((2R,5R)-5-((3-chloroimidazo[1,2-a]pyrazin-8-yl)oxy)-2-methylpiperidin-1-yl)methanone;

1-(2-((2R,5R)-5-((3-chloroimidazo[1,2-a]pyrazin-8-yl)oxy)-2-methylpiperidine-1-carbonyl)phenyl)cyclopropanecarbonitrile;

(2-(2H-1,2,3-triazol-2-yl)thiophen-3-yl)((2R,5R)-5-((3-chloroimidazo[1,2-a]pyrazin-8-yl)oxy)-2-methylpiperidin-1-yl)methanone;

(2-(2H-1,2,3-triazol-2-yl)phenyl)((2R,5R)-5-((3-chloroimidazo[1,2-a]pyrazin-8-yl)amino)-2-methylpiperidin-1-yl)methanone;

((2R,5R)-5-((3-chloroimidazo[1,2-a]pyrazin-8-yl)amino)-2-methylpiperidin-1-yl)(2-(pyrimidin-2-yl)phenyl)methanone;

(2-(2H-1,2,3-triazol-2-yl)phenyl)((2R,5R)-5-((3-fluoroimidazo[1,2-a]pyrazin-8-yl)oxy)-2-methylpiperidin-1-yl)methanone;

(2-(2H-1,2,3-triazol-2-yl)phenyl)((2R,5R)-5-((3-bromoimidazo[1,2-a]pyrazin-8-yl)oxy)-2-methylpiperidin-1-yl)methanone;

(2-(2H-1,2,3-triazol-2-yl)phenyl)((2R,5R)-2-methyl-5-((3-methylimidazo[1,2-a]pyrazin-8-yl)oxy)piperidin-1-yl)methanone;

8-(((3R,6R)-1-(2-(2H-1,2,3-triazol-2-yl)benzoyl)-6-methylpiperidin-3-yl)oxy)imidazo[1,2-a]pyrazine-3-carbonitrile;

(2-(2H-1,2,3-triazol-2-yl)phenyl)((2R,5R)-2-methyl-5-((3-vinylimidazo[1,2-a]pyrazin-8-yl)oxy)piperidin-1-yl)methanone;

(2-(2H-1,2,3-triazol-2-yl)phenyl)((2R,5R)-5-((3-ethylimidazo[1,2-a]pyrazin-8-yl)oxy)-2-methylpiperidin-1-yl)methanone;

(2-(2H-1,2,3-triazol-2-yl)phenyl)((2R,5R)-5-((3-(difluoromethyl)imidazo[1,2-a]pyrazin-8-yl)oxy)-2-methylpiperidin-1-yl)methanone;

((2R,5R)-5-((3-(difluoromethyl)imidazo[1,2-a]pyrazin-8-yl)oxy)-2-methylpiperidin-1-yl)(2-((methylsulfonyl)methyl)phenyl)methanone;

(2-(2H-1,2,3-triazol-2-yl)thiophen-3-yl)((2R,5R)-5-((3-(difluoromethyl)imidazo[1,2-a]pyrazin-8-yl)oxy)-2-methylpiperidin-1-yl)methanone;

(4-(2H-1,2,3-triazol-2-yl)thiophen-3-yl)((2R,5R)-5-((3-(difluoromethyl)imidazo[1,2-a]pyrazin-8-yl)oxy)-2-methylpiperidin-1-yl)methanone;

1-(2-((2R,5R)-5-((3-(difluoromethyl)imidazo[1,2-a]pyrazin-8-yl)oxy)-2-methylpiperidine-1-carbonyl)phenyl)cyclopropanecarbonitrile;

((2R,5R)-5-((3-(difluoromethyl)imidazo[1,2-a]pyrazin-8-yl)oxy)-2-methylpiperidin-1-yl)(4-fluoro-2-(2H-1,2,3-triazol-2-yl)phenyl)methanone;

(2-(2H-tetrazol-2-yl)phenyl)((2R,5R)-5-((3-(difluoromethyl)imidazo[1,2-a]pyrazin-8-yl)oxy)-2-methylpiperidin-1-yl)methanone;

((2R,5R)-5-((3-(difluoromethyl)imidazo[1,2-a]pyrazin-8-yl)oxy)-2-methylpiperidin-1-yl)(2-(methoxymethyl)phenyl)methanone;

(3-(1H-pyrazol-1-yl)pyrazin-2-yl)((2R,5R)-5-((3-(difluoromethyl)imidazo[1,2-a]pyrazin-8-yl)oxy)-2-methylpiperidin-1-yl)methanone;

((2R,5R)-5-((3-(difluoromethyl)imidazo[1,2-a]pyrazin-8-yl)oxy)-2-methylpiperidin-1-yl)(3-(pyridin-2-yl)pyrazin-2-yl)methanone;

methyl 2-((2R,5R)-5-((3-(difluoromethyl)imidazo[1,2-a]pyrazin-8-yl)oxy)-2-methylpiperidine-1-carbonyl)benzoate;

((2R,5R)-5-((3-(difluoromethyl)imidazo[1,2-a]pyrazin-8-yl)oxy)-2-methylpiperidin-1-yl)(3-phenylpyridin-2-yl)methanone;

((2R,5R)-5-((3-(difluoromethyl)imidazo[1,2-a]pyrazin-8-yl)oxy)-2-methylpiperidin-1-yl)(2-(2,2,2-trifluoroethoxy)pyridin-3-yl)methanone;

(2-(2,2-difluoroethoxy)pyridin-3-yl)((2R,5R)-5-((3-(difluoromethyl)imidazo[1,2-a]pyrazin-8-yl)oxy)-2-methylpiperidin-1-yl)methanone;

(2-(1H-pyrazol-1-yl)pyridin-3-yl)((2R,5R)-5-((3-(difluoromethyl)imidazo[1,2-a]pyrazin-8-yl)oxy)-2-methylpiperidin-1-yl)methanone;

((2R,5R)-5-((3-(difluoromethyl)imidazo[1,2-a]pyrazin-8-yl)oxy)-2-methylpiperidin-1-yl)(2-(pyrazin-2-yl)phenyl)methanone;

((2R,5R)-5-((3-(difluoromethyl)imidazo[1,2-a]pyrazin-8-yl)oxy)-2-methylpiperidin-1-yl)(2-(pyrimidin-2-yl)phenyl)methanone;

((2R,5R)-5-((3-(difluoromethyl)imidazo[1,2-a]pyrazin-8-yl)oxy)-2-methylpiperidin-1-yl)(4-(pyrimidin-2-yl)thiophen-3-yl)methanone;

((2R,5R)-5-((3-(difluoromethyl)imidazo[1,2-a]pyrazin-8-yl)oxy)-2-methylpiperidin-1-yl)(2-(pyrimidin-2-yl)thiophen-3-yl)methanone;

(2-(2H-1,2,3-triazol-2-yl)phenyl)((2R,5R)-2-methyl-5-((3-(trifluoromethyl)imidazo[1,2-a]pyrazin-8-yl)oxy)piperidin-1-yl)methanone;

(2-(2H-1,2,3-triazol-2-yl)thiophen-3-yl)((2R,5R)-2-methyl-5-((3-(trifluoromethyl)imidazo[1,2-a]pyrazin-8-yl)oxy)piperidin-1-yl)methanone;

1-(2-((2R,5R)-2-methyl-5-(trifluoromethyl)imidazo[1,2-a]pyrazin-8-yl)oxy)piperidine-1-carbonyl)phenyl)cyclopropanecarbonitrile;

(2-(2H-tetrazol-2-yl)phenyl)((2R,5R)-2-methyl-5-((3-(trifluoromethyl)imidazo[1,2-a]pyrazin-8-yl)oxy)piperidin-1-yl)methanone;

((2R,5R)-2-methyl-5-((3-(trifluoromethyl)imidazo[1,2-a]pyrazin-8-yl)oxy)piperidin-1-yl)(2-((methylsulfonyl)methyl)phenyl)methanone;

((2R,5R)-2-methyl-5-((3-(trifluoromethyl)imidazo[1,2-a]pyrazin-8-yl)oxy)piperidin-1-yl)(3-phenylpyridin-2-yl)methanone;

((2R,5R)-2-methyl-5-((3-(trifluoromethyl)imidazo[1,2-a]pyrazin-8-yl)oxy)piperidin-1-yl)(2-(2,2,2-trifluoroethoxy)pyridin-3-yl)methanone;

(2-(2,2-difluoroethoxy)pyridin-3-yl)((2R,5R)-2-methyl-5-((3-(trifluoromethyl)imidazo[1,2-a]pyrazin-8-yl)oxy)piperidin-1-yl)methanone;

(2-(1H-pyrazol-1-yl)pyridin-3-yl)((2R,5R)-2-methyl-5-(trifluoromethyl)imidazo[1,2-a]pyrazin-8-yl)oxy)piperidin-1-yl)methanone;

((2R,5R)-2-methyl-5-((3-(trifluoromethyl)imidazo[1,2-a]pyrazin-8-yl)oxy)piperidin-1-yl)(2-(pyrimidin-2-yl)phenyl)methanone;

(2-(2H-1,2,3-triazol-2-yl)phenyl)((2R,5R)-5-((3-(2,2-difluoro-1-hydroxyethyl)imidazo[1,2-a]pyrazin-8-yl)oxy)-2-methylpiperidin-1-yl)methanone;

(2-(2H-1,2,3-triazol-2-yl)phenyl)((2R,5R)-5-((3-(1-hydroxyethyl)imidazo[1,2-a]pyrazin-8-yl)oxy)-2-methylpiperidin-1-yl)methanone;

(2-(2H-1,2,3-triazol-2-yl)phenyl)((2R,5R)-2-methyl-5-(pyrazolo[1,5-a]pyrazin-4-yloxy)piperidin-1-yl)methanone;

(2-(2H-1,2,3-triazol-2-yl)thiophen-3-yl)((2R,5R)-2-methyl-5-(pyrazolo[1,5-a]pyrazin-4-yloxy)piperidin-1-yl)methanone;

(4-(2H-1,2,3-triazol-2-yl)thiophen-3-yl)((2R,5R)-2-methyl-5-(pyrazolo[1,5-a]pyrazin-4-yloxy)piperidin-1-yl)methanone;

1-(2-((2R,5R)-2-methyl-5-(pyrazolo[1,5-a]pyrazin-4-yloxy)piperidine-1-carbonyl)phenyl)cyclopropanecarbonitrile;

(4-fluoro-2-(2H-1,2,3-triazol-2-yl)phenyl)((2R,5R)-2-methyl-5-(pyrazolo[1,5-a]pyrazin-4-yloxy)piperidin-1-yl)methanone;

((2R,5R)-2-methyl-5-(pyrazolo[1,5-a]pyrazin-4-yloxy)piperidin-1-yl)(4-(pyrimidin-2-yl)thiophen-3-yl)methanone;

((2R,5R)-2-methyl-5-(pyrazolo[1,5-a]pyrazin-4-yloxy)piperidin-1-yl)(2-(pyrimidin-2-yl)thiophen-3-yl)methanone;

(2-(2H-tetrazol-2-yl)phenyl)((2R,5R)-2-methyl-5-(pyrazolo[1,5-a]pyrazin-4-yloxy)piperidin-1-yl)methanone;

((2R,5R)-5-(imidazo[1,2-a]pyrazin-8-yloxy)-2-methylpiperidin-1-yl)(2-((methylsulfonyl)methyl)phenyl)methanone;

((2R,5R)-2-methyl-5-(pyrazolo[1,5-a]pyrazin-4-yloxy)piperidin-1-yl)(3-(pyridin-2-yl)pyrazin-2-yl)methanone;

methyl 2-((2R,5R)-2-methyl-5-(pyrazolo[1,5-a]pyrazin-4-yloxy)piperidine-1-carbonyl)benzoate;

(3-(1H-pyrazol-1-yl)pyrazin-2-yl)((2R,5R)-2-methyl-5-(pyrazolo[1,5-a]pyrazin-4-yloxy)piperidin-1-yl)methanone;

(2-ethoxyphenyl)((2R,5R)-2-methyl-5-(pyrazolo[1,5-a]pyrazin-4-yloxy)piperidin-1-yl)methanone;

((2R,5R)-2-methyl-5-(pyrazolo[1,5-a]pyrazin-4-yloxy)piperidin-1-yl)(2-propylphenyl)methanone;

(2-isopropoxypyridin-3-yl)((2R,5R)-2-methyl-5-(pyrazolo[1,5-a]pyrazin-4-yloxy)piperidin-1-yl)methanone;

(2-isopropoxyphenyl)((2R,5R)-2-methyl-5-(pyrazolo[1,5-a]pyrazin-4-yloxy)piperidin-1-yl)methanone;

((2R,5R)-2-methyl-5-(pyrazolo[1,5-a]pyrazin-4-yloxy)piperidin-1-yl)(2-(pyrimidin-2-yl)phenyl)methanone;

(2-(2H-1,2,3-triazol-2-yl)phenyl)((2R,5R)-2-methyl-5-(pyrazolo[1,5-a]pyrazin-4-ylamino)piperidin-1-yl)methanone;

(2-(2H-1,2,3-triazol-2-yl)phenyl)((2R,5R)-2-methyl-5-(pyrazolo[1,5-a]pyrazin-4-ylthio)piperidin-1-yl)methanone;

(2-(2H-1,2,3-triazol-2-yl)phenyl)((2R,5R)-5-((3-bromopyrazolo[1,5-a]pyrazin-4-yl)oxy)-2-methylpiperidin-1-yl)methanone;

(2-(2H-1,2,3-triazol-2-yl)phenyl)((2R,5R)-2-methyl-5-((3-methylpyrazolo[1,5-a]pyrazin-4-yl)oxy)piperidin-1-yl)methanone;

(2-(2H-1,2,3-triazol-2-yl)phenyl)((2R,5R)-2-methyl-5-(pyrazolo[1,5-a]pyridin-4-yloxy)piperidin-1-yl)methanone;

(2-(2H-1,2,3-triazol-2-yl)phenyl)((2R,5R)-2-methyl-5-(oxazolo[5,4-b]pyridin-7-yloxy)piperidin-1-yl)methanone;

(2-(2H-tetrazol-2-yl)phenyl)((2R,5R)-2-methyl-5-(oxazolo[5,4-b]pyridin-7-yloxy)piperidin-1-yl)methanone;

methyl 2-((2R,5R)-2-methyl-5-(oxazolo[5,4-b]pyridin-7-yloxy)piperidine-1-carbonyl)benzoate;

(2-ethoxyphenyl)((2R,5R)-2-methyl-5-(oxazolo[5,4-b]pyridin-7-yloxy)piperidin-1-yl)methanone;

(2-(2H-1,2,3-triazol-2-yl)phenyl)((2R,5R)-2-methyl-5-((1-methyl-1H-pyrazolo[4,3-c]pyridin-4-yl)oxy)piperidin-1-yl)methanone;

(2-(2H-1,2,3-triazol-2-yl)phenyl)((2R,5R)-2-methyl-5-((1-methyl-1H-pyrazolo[4,3-c]pyridin-4-yl)amino)piperidin-1-yl)methanone;

(2-(2H-1,2,3-triazol-2-yl)phenyl)((2R,5R)-2-methyl-5-((2-methyl-2H-pyrazolo[4,3-c]pyridin-4-yl)amino)piperidin-1-yl)methanone;

(2-(2H-1,2,3-triazol-2-yl)phenyl)((2R,5R)-2-methyl-5-((1-methyl-1H-imidazo[4,5-c]pyridin-4-yl)oxy)piperidin-1-yl)methanone;

(2-(2H-1,2,3-triazol-2-yl)phenyl)((2R,5R)-2-methyl-5-((3-methyl-3H-imidazo[4,5-c]pyridin-4-yl)oxy)piperidin-1-yl)methanone;

(2-(2H-1,2,3-triazol-2-yl)phenyl)((2R,5R)-2-methyl-5-((3-methyl-3H-imidazo[4,5-c]pyridin-4-yl)amino)piperidin-1-yl)methanone;

(2-(2H-1,2,3-triazol-2-yl)phenyl)((2R,5R)-2-methyl-5-((1-methyl-1H-imidazo[4,5-c]pyridin-4-yl)amino)piperidin-1-yl)methanone;

(2-(2H-1,2,3-triazol-2-yl)phenyl)((2R,5R)-5-(imidazo[1,5-a]pyrazin-8-yloxy)-2-methylpiperidin-1-yl)methanone;

(2-(2H-1,2,3-triazol-2-yl)phenyl)((2R,5R)-2-methyl-5-((3-methylimidazo[1,5-a]pyrazin-8-yl)oxy)piperidin-1-yl)methanone;

(2-(2H-1,2,3-triazol-2-yl)phenyl)((2R,5R)-2-methyl-5-((2-methyl-[1,2,4]triazolo[1,5-c]pyrimidin-5-yl)oxy)piperidin-1-yl)methanone;

(2-(2H-1,2,3-triazol-2-yl)phenyl)((2R,5R)-2-methyl-5-((2-methyl-[1,2,4]triazolo[1,5-c]pyrimidin-5-yl)amino)piperidin-1-yl)methanone; and 8-(((3R,6R)-1-(2-(2H-1,2,3-triazol-2-yl)benzoyl)-6-methylpiperidin-3-yl)oxy)-2-methyl-[1,2,4]triazolo[4,3-a]pyridin-3(2H)-one;

or a pharmaceutically acceptable salt thereof.

The subject compounds are useful in a method of antagonizing orexin receptor activity in a patient such as a mammal in need of such inhibition comprising the administration of an effective amount of the compound. The present invention is directed to the use of the compounds disclosed herein as antagonists of orexin receptor activity. In addition to primates, especially humans, a variety of other mammals may be treated according to the method of the present invention. The present invention is directed to a compound of the present invention or a pharmaceutically acceptable salt thereof that could be useful in treating the disorders and diseases noted herein in humans and animals. The present invention may further be directed to a use of a compound of the present invention or a pharmaceutically acceptable salt thereof for the manufacture of a medicament for antagonizing orexin receptor activity or treating the disorders and diseases noted herein in humans and animals.

The subject treated in the present methods is generally a mammal, such as a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as orexin receptor OX1R and/or OX2R antagonists may be readily determined without undue experimentation by methodology well known in the art, including the "FLIPR $Ca^{2+}$ Flux Assay" (Okumura et al., Biochem. Biophys. Res. Comm. 280:976-981, 2001). In a typical experiment the OX1 and OX2 receptor antagonistic activity of the compounds of the present invention was determined in accordance with the following experimental method. For intracellular calcium measurements, Chinese hamster ovary (CHO) cells expressing the rat orexin-1 receptor or the human orexin-2 receptor, are grown in Iscove's modified DMEM containing 2 mM L-glutamine, 0.5 g/ml G418, 1% hypoxanthine-thymidine supplement, 100 U/ml penicillin, 100 µg/ml streptomycin and 10% heat-inactivated fetal calf serum (FCS). The cells are seeded at 20,000 cells/well into Becton-Dickinson black 384-well clear bottom sterile plates coated with poly-D-lysine. All reagents are from GIBCO-Invitrogen Corp. The seeded plates are incubated overnight at 37° C. and 5% $CO_2$. Ala-6,12 human orexin-A as the agonist is prepared as a 1 mM stock solution in 1% bovine serum albumin (BSA) and diluted in assay buffer (HBSS containing 20 mM HEPES, 0.1% BSA and 2.5 mM probenecid, pH7.4) for use in the assay at a final concentration of 70 pM. Test compounds are prepared as 10 mM stock solution in DMSO, then diluted in 384-well plates, first in DMSO, then assay buffer. On the day of the assay, cells are washed 3 times with 100 µl assay buffer and then incubated for 60 min (37° C., 5% $CO_2$) in 60 µl assay buffer containing 1 µl M Fluo-4AM ester, 0.02% pluronic acid, and 1% BSA. The dye loading solution is then aspirated and cells are washed 3 times with 100 µl assay buffer. 30 µl of that same buffer is left in each well. Within the Fluorescent Imaging Plate Reader (FLIPR, Molecular Devices), test compounds are added to the plate in a volume of 25 µl, incubated for 5 min and finally 25 µl of agonist is added. Fluorescence is measured for each well at 1 second intervals for 5 minutes and the height of each fluorescence peak is compared to the height of the fluorescence peak induced by 70 pM Ala-6,12 orexin-A with buffer in place of antagonist. For each antagonist, $IC_{50}$ value (the concentration of compound needed to inhibit 50% of the agonist response) is determined. Alternatively, compound potency can be assessed by a radioligand binding assay (described in Bergman et. al. Bioorg. Med. Chem. Lett. 2008, 18, 1425-

1430) in which the inhibition constant ($K_i$) is determined in membranes prepared from CHO cells expressing either the OX1 or OX2 receptor. The intrinsic orexin receptor antagonist activity of a compound which may be used in the present invention may be determined by these assays.

All of the final compounds of the following examples had activity in the FLIPR assay with an $IC_{50}$ of about 5 nM to 200 nM against the orexin-2 receptor. Additional data is provided in the following Examples. Such a result is indicative of the intrinsic activity of the compounds in use as antagonists of orexin-1 receptor and/or the orexin-2 receptor. In general, one of ordinary skill in the art would appreciate that a substance is considered to effectively antagonize the orexin receptor if it has an $IC_{50}$ of less than about 50 µM.

The orexin receptors have been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with orexin receptors, including one or more of the following conditions or diseases: sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders overeating, anorexia, bulimia, cachexia, dysregulated appetite control, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, lung disease, abnormal heart rhythms and arrythmias, myocardial infarction, congestive heart failure, coronary heart disease, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; sudden death, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, intestinal motility dyskinesias, obesity-related gastro-esophageal reflux, hypothalmic diseases, hypophysis diseases, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function, including cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; Huntington's disease and Tourette syndrome; Cushing's syndrome/disease; basophile adenoma; prolactinoma; hyperprolactinemia; hypophysis tumor/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions, seizure disorders, absence seisures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; dissociateive disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache and other diseases related to general orexin system dysfunction.

Thus, in certain embodiments the present invention may provide methods for: enhancing the quality of sleep; augmenting sleep maintenance; increasing REM sleep; increasing stage 2 sleep; decreasing fragmentation of sleep patterns; treating insomnia and all types of sleep disorders; treating or controlling sleep disturbances associated with diseases such as neurological disorders including neuropathic pain and restless leg syndrome; treating or controlling addiction disorders; treating or controlling psychoactive substance use and abuse; enhancing cognition; increasing memory retention; treating or controlling obesity; treating or controlling diabetes and appetite, taste, eating, or drinking disorders; treating or controlling hypothalamic diseases; treating or controlling depression; treating, controlling, ameliorating or reducing the risk of epilepsy, including absence epilepsy; treating or controlling pain, including neuropathic pain; treating or controlling Parkinson's disease; treating or controlling psychosis; treating or controlling dysthymic, mood, psychotic and anxiety disorders; treating or controlling depression, including major depression and major depression disorder; treating or controlling bipolar disorder; or treating, controlling, ameliorating or reducing the risk of schizophrenia, in a mammalian patient in need thereof which comprises administering to the patient a therapeutically effective amount of a compound of the present invention.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of orexin receptors. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day. The compounds may be administered before bedtime. For example, the compounds may be administered about 1 hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used alone. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with other compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, ornortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, including, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor a agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA: cholesterol acyltransferase (ACAT)) inhibitors such as avasimibe, and melinamide, (v) anti-oxidants, such as probucol, (vi) vitamin E, and (vii) thyromimetics; (f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579; (g) PPARδ agonists, such as those disclosed in WO97/28149; (h) PPAR α/δ agonists, such as muraglitazar, and the compounds disclosed in U.S. Pat. No. 6,414,002; (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid CB$_1$ receptor antagonists or inverse agonists, such as rimonabant, taranabant, AMT-251, and SR-14778 and SR 141716A (Sanofi Synthelabo), SLV-319 (Solvay), BAY 65-2520 (Bayer) and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001, 836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027; (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) Mc4r (melanocortin 4 receptor) agonists, such as CHIR86036 (Chiron), ME-10142, and ME-10145 (Melacure), CHIR86036 (Chiron); PT-141, and PT-14 (Palatin); (16)

5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR14613, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) (3-hydroxy steroid dehydrogenase-1 inhibitors (β-HSD-1); (26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6, beta-Ala11,Phe13,Nle14]Bn(6-14) and [D-Phe6,Phe13]Bn (6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl] benzoic acid (TTNPB), retinoic acid; (37) thyroid hormone β agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444, sitagliptin; and the compounds disclosed in U.S. Pat. No. 6,699,871, WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); (50) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 11β HSD-1 (11-beta hydroxy steroid dehydrogenase type 1) inhibitors such as BVT 3498, BVT 2733, and those disclosed in WO 01/90091, WO 01/90090, WO 01/90092, U.S. Pat. No. 6,730,690 and US 2004-0133011; (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide., (89) neuromedin U and analogs or derivatives thereof, (90) oxyntomodulin and analogs or derivatives thereof, and (91) Neurokinin-1 receptor antagonists (NK-1 antagonists) such as the compounds disclosed in: U.S. Pat. Nos. 5,162,339, 5,232,929, 5,242,930, 5,373,003, 5,387, 595, 5,459,270, 5,494,926, 5,496,833, and 5,637,699.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; citalopram, duloxetine, fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H$_3$ antagonists; AMPA agonists; PDE IV inhibitors; GABA$_A$ inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole.

In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone.

In another embodiment, the subject compound may be employed in combination with a nicotine agonist or a nicotine receptor partial agonist such as varenicline, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin® and Concerta®), atomoxetine (e.g., Strattera®), a monoamine oxidase inhibitor (MAOI), amphetamines (e.g., Adderall®)) and anti-obesity agents, such as apo-B/MTP inhibitors, 11Beta-hydroxy steroid dehydrogenase-1 (11Beta-HSD type 1) inhibitors, peptide YY3-36 or analogs thereof, MCR-4 agonists, CCK-A agonists, monoamine reuptake inhibitors, sympathomimetic agents, β3 adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists), thyromimetic agents, dehydroepiandrosterone or analogs thereof, glucocorticoid receptor antagonists, other orexin receptor antagonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and pharmaceutically acceptable salts thereof.

In another embodiment, the subject compound may be employed in combination with an anoretic agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptable salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a nonsteroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention may be effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art (e.g. PCT Patent Publications WO2001/68609, WO2004/085403, WO2005/118548, WO2008/147518, WO2009/143033 and WO2010/048012) or as illustrated herein. The following abbreviations are used herein: Me: methyl; Et: ethyl; t-Bu: tert-butyl; Ar: aryl; Ph: phenyl; BINAP: 2,2'-bis(diphenylphosphino)-1,1'-binaphthyl; Bn: benzyl; Ac: acetyl; Boc: tert-butyloxy carbonyl; BSA: bovine serum albumin; CbzCl: benzylchloroformate; CDI: carbonyl diimidazole; DCM: dichloromethane; DCE: dichloroethane; DEAD: diethylazodicarboxylate; DIPEA: N,N-diisopropylethylamine; DMF: N,N-dimethylformamide; DMSO: dimethylsulfoxide; $CH_2Cl_2$: dichloromethane; EDC: N-(3-Dimethylaminopropyl)-N'-ethylcarbodiimide; $Et_3N$: triethylamine; EtOAc: ethyl acetate; EtOH: ethanol; HCl: hydrogen chloride; HOAt: 1-hydroxy-7-azabenzotriazole; HOBT: hydroxybenzotriazole hydrate; HPLC: high performance liquid chromatography; Hunig's base: N,N-diisopropylethylamine; MeOH: methanol; $MgSO_4$: magnesium sulfate; MTBE: methyl tert-butyl ether; $NaHCO_3$: sodium bicarbonate; NaOH: sodium hydroxide; NMM: N-methylmorpholine; $PtO_2$: platinum oxide; PyClu: 1-(chloro-1-pyrrolidinylmethylene)-pyrrolidinium hexafluorophosphate; rt: room temperature; $SOCl_2$: thionyl chloride; T3P: 2,4,6-tripropyl-1,3,5,2,4,6-trioxatriphosphorinane-2,4,6-trioxide; THF: tetrahydrofuran; TFA: trifluoracetic acid; X-Phos: 2-(dicyclohexyl-phosphino)-2',4',6'-triisopropylbiphenyl; RT: room temperature. The compounds of the present invention can be prepared in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Example A: Synthesis of Compounds

Intermediate A 2-(2,2,2-Trifluoroethyl)benzoic Acid

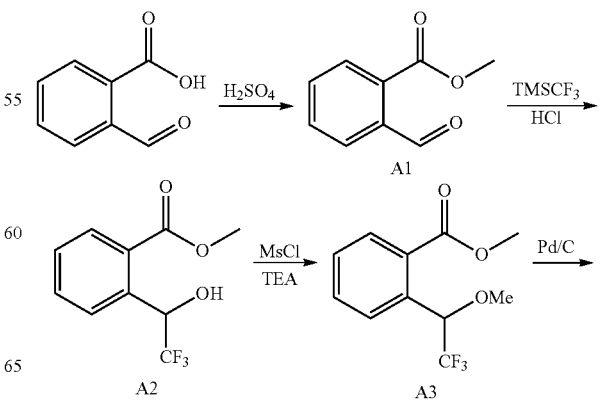

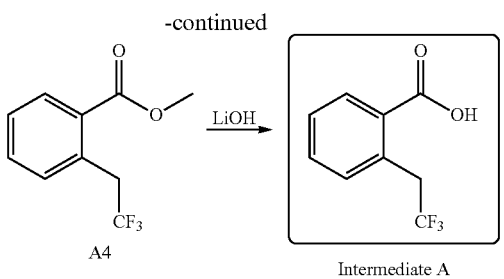

Step 1: Methyl 2-formylbenzoate (A1)

To a solution of $H_2SO_4$ (2 mL) in MeOH (100 mL) was added 2-formyl benzoic acid (10.0 g, 66.2 mmol). The resulting mixture was stirred at 70° C. overnight. After cooling to RT, the mixture was concentrated in vacuo, adjusted pH to 8 with aq. $NaHCO_3$ and extracted with EtOAc (10 mL×3). The combined organic layers were dried over anhydrous sodium sulfate, filtered and concentrated in vacuo. The residue was purified by silica gel gradient chromatography (10% EtOAc in petroleum ether) to give the title compound (4.80 g) as yellow oil. LRMS m/z (M+H) 165.1 found, 165.1 required $^1$H NMR ($CDCl_3$, 400 MHz): δ 10.58 (s, 1H), 7.89-7.95 (m, 2H), 7.60-7.63 (m, 2H), 3.95 (s, 3H).

Step 2: Methyl 2-(2,2,2-trifluoro-1-hydroxyethyl)benzoate (A2)

To a suspension of the compound from step 1 (3.60 g, 21.9 mmol) and CsF (1.67 g, 10.9 mmol) in dry THF (36 mL) at 0° C. was added $TMSCF_3$ (4.68 g, 32.9 mmol). The mixture was stirred at 0° C. for 1 h. The mixture was adjusted to pH 2 with 1N HCl solution and stirred for another 1 h and extracted with EtOAc (10 mL×3). The combined organic layers were dried over anhydrous sodium sulfate, filtered and concentrated in vacuo and the residue was purified by silica gel gradient chromatography (10% EtOAc in petroleum ether) to give the title compound (1.70 g) as colorless oil. LRMS m/z (M+H) 235.1 found, 235.1 required.

$^1$H NMR ($CDCl_3$, 400 MHz): δ 7.97 (d, J=8.0 Hz, 1H), 7.69 (d, J=8.0 Hz, 1H), 7.58 (t, J=7.2 Hz, 1H), 7.45 (t, J=7.2 Hz, 1H), 5.92 (br, 1H), 4.51 (br, 1H), 3.92 (s, 3H).

Step 3: methyl 2-(2,2,2-trifluoro-1-((methylsulfonyl)oxy)ethyl)benzoate (A3)

To a solution of the compound from step 2 (1.10 g, 4.70 mmol) and TEA (1.96 mL, 14.1 mmol) in DCM (10 mL) at RT was added MsCl (807 mg, 7.05 mmol) dropwise. The resulting mixture was stirred at RT for 1.5 hr, diluted with DCM and washed with brine (5 mL×2), dried over anhydrous sodium sulfate, filtered and the filtrate was concentrated in vacuo to give the title compound (1.40 g) as a white solid. LRMS m/z (M+H) 313.0 found, 313.0 required.

$^1$H NMR ($CDCl_3$, 400 MHz): δ 8.07 (d, J=7.6 Hz, 1H), 7.79 (d, J=8.4 Hz, 1H), 7.65 (t, J=6.0 Hz, 1H), 7.51-7.55 (m, 2H), 3.93 (s, 3H), 3.05 (s, 3H).

Step 4: methyl 2-(2,2,2-trifluoroethyl)benzoate (A4)

A solution of the product from step 3 (1.00 g, 3.20 mmol) in methanol (40 mL) was stirred in the presence of Pd/C (1.0 g) under 50 psi of $H_2$ atmosphere at 50° C. overnight. LCMS indicated the reaction was completed, the mixture was filtered through celite pad. The filtrate was concentrated in vacuo to give the title compound (550 mg) as colorless oil. LRMS m/z (M+H) 219.1 found, 219.1 required.

Step 5: 2-(2,2,2-trifluoroethyl)benzoic Acid (Intermediate A)

To a solution of the product from step 4 (550 mg, 2.50 mmol) in $MeOH/H_2O$ (10 mL/1 mL) was added LiOH (240 mg, 10.0 mmol) at RT. The resulting mixture was stirred at RT for 12 hours. Water (10 mL) was added and the mixture was washed with EtOAc (10 mL×2) and adjusted pH=~3 with conc.HCl and extracted with DCM (20 mL×3). The combined organic layers were washed with brine (20 mL), dried over sodium sulfate, filtered and the filtrate was concentrated in vacuo to give the title compound as a pale white solid (330 mg). LRMS m/z (M+H) 205.0 found, 205.0 required.

$^1$H NMR (Methanol-d4, 400 MHz): δ 7.99 (d, J=7.4 Hz, 1H), 7.49-7.58 (m, 1H), 7.37-7.49 (m, 2H), 4.09 (q, J=11.0 Hz, 2H)

Intermediate B

2-Propylbenzoic Acid

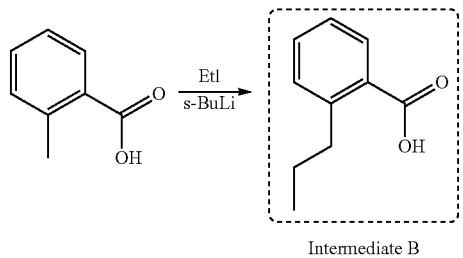

Step 1: 2-propylbenzoic Acid (Intermediate B)

To a solution of 2-methylbenzoic acid (20 g, 0.15 mmol) in THF (200 mL) was dropwise added s-BuLi (340 mL, 0.45 mmol) at −78° C. After addition, the mixture was stirred at −78° C. for 0.5 h. Then iodoethane (137 g, 0.88 mmol) was added. The resulting mixture was allowed to warm up to RT and stirred overnight, quenched with water and extracted with EtOAc (300 mL×3). The combined organic layers were washed with brine, dried over $MgSO_4$, filtered and concentrated in vacuo. The residue was purified by silica chromatography (50% EtOAc in petroleum ether) to give the title compound as a pale yellow oil (22 g). LRMS m/z (M+H) 165.1 found, 165.1 required.

$^1$H NMR (DMSO-d6, 400 MHz): δ 12.80 (brs, 1H), 7.75~7.73 (m, 1H), 7.39~7.43 (m, 1H), 7.22~7.36 (m, 2H), 2.87~2.84 (m, 2H), 1.49~1.54 (m, 2H), 0.84~0.87 (m, 3H).

Intermediate C 2-(1-Cyanocyclopropyl)benzoic Acid

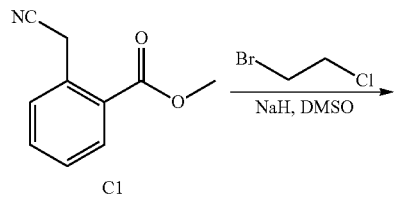

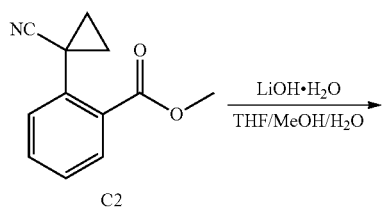

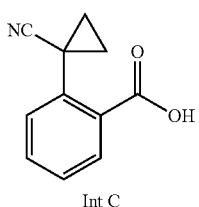

Int C

Step 1: Methyl 2-(1-cyanocyclopropyl)benzoate (C₂)

To a solution of NaH (1.1 g, 26.2 mmol) in DMSO (20 mL) was added compound C1 (2 g, 11.4 mmol); after stirring at room temperature under nitrogen for 1 h, 1-bromo-2-chloroethane (1.8 g, 12.6 mmol) was added, the mixture stirred at room temperature for 2h. The mixture was quenched with ice water (10 mL) and extracted with EtOAc (10 mL×3). The organic layer was combined, dried and concentrated in vacuo to give the crude compound, which was purified by column chromatography on silica gel eluting with (Petroleum Ether/EtOAc 20:1) to give the title compound (2 g) as a white solid. MS (ESI) m/e (M+H+) was detected.

Step 2: 2-(1-Cyanocyclopropyl)benzoic Acid (Intermediate C)

A solution of compound from step 1 in THF/MeOH/H₂O (3:1:1, 16 mL) was treated with lithium hydroxide in water (3 mL). The mixture was stirred overnight at room temperature. The THF and MeOH were removed in vacuo and the resulting solution acidified to pH ~1 with HCl (1 N) to give a white crystalline precipitate. The crystals were isolated by filtration, washed with water and dried in vacuo affording intermediate A as a white solid. MS (ESI) m/e (M+H⁺): 187.9.

Intermediate D 2-(2H-Tetrazol-2-yl)benzoic Acid

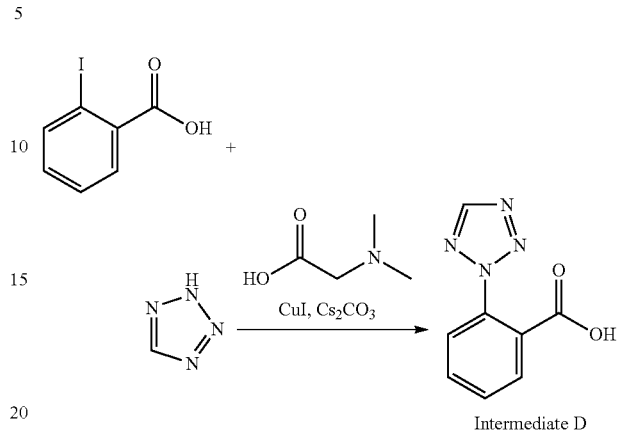

Intermediate D

To a 20 mL microwave tube was charged 2-iodobenzoic acid (1.85 g, 7.46 mmol), cesium carbonate (4.06 g, 12.5 mmol), copper(I) iodide (0.128 g, 0.671 mmol), and DMA (8.0 mL). N,N'-Dimethylglyine (0.131 g, 1.27 mmol) and tetrazole (1.29 g, 18.4 mmol) were added, and the solution was irradiated in a microwave reactor at 100° C. for 1 hour. The reaction was diluted with water and 1 N aqeous sodium hydroxide and washed with EtOAc. The aqueous fraction was acidified with conc. HCl and extracted 2× with EtOAc. The combined organic fractions were washed with brine, dried over magnesium sulfate, filtered, and concentrated. The residue was purified by silica gel gradient chromatography [0-85% (1% acetic acid in EtOAc) in hexanes], providing the title compound. ¹H NMR (400 MHz, CD₃OD): δ 7.72-7.84 (m, 3H), 8.07 (dd, J=7.6, 1.6 Hz, 1H), 8.90 (s, 1H) ppm. LRMS m/z (M+H) 191.1 found, 191.2.

Intermediate E 2-(2H)-1,2,3-Triazol-2-yl)thiophene-3-carboxylic Acid

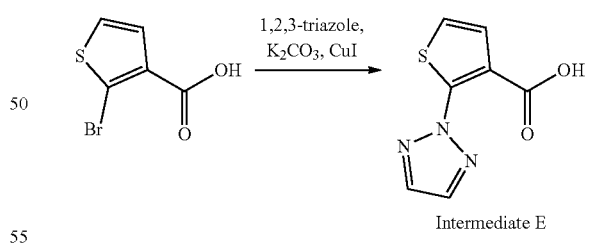

Intermediate E

A solution of 2-bromo-3-thiophene carboxylic acid (1.50 g, 7.24 mmol), 1H-1,2,3-triazole (0.600 g, 8.69 mmol), potassium carbonate (2.00 g, 14.5 mmol), and copper iodide (0.138 g, 0.724 mmol) in DMF (36.2 mL) was purged subsurface with nitrogen and heated to 75° C. for 96 h. The reaction was diluted with water, washed with ether, and acidified with conc. HCl. The acidic aqueous solution was extracted 3× with EtOAc and the combined organic fractions were washed with brine, dried over magnesium sulfate, filtered, and concentrated. The crude material was purified by silica gel gradient chromatography [0-70% (1% acetic acid in EtOAc) in hexanes], providing the title compound as an off-white solid. LRMS m/z (M+H) 196.2 found, 196.1 required.

Intermediate F

Potassium 2-(pyrimidin-2-yl)thiophene-3-carboxylate

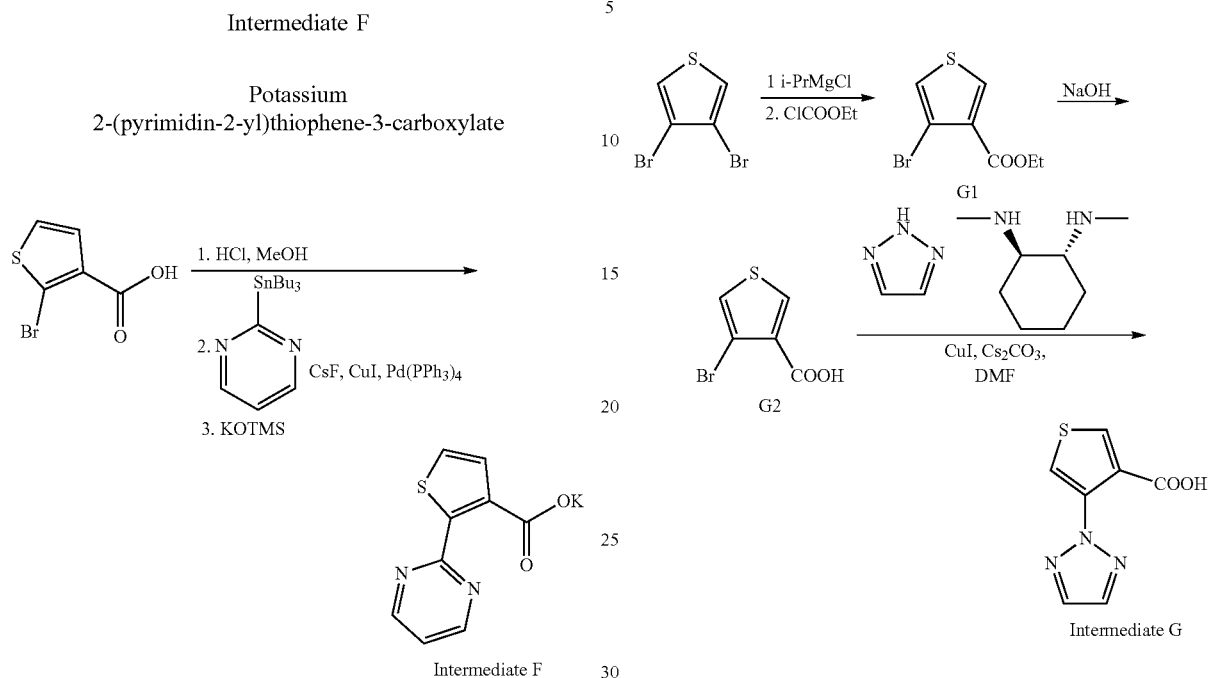

Intermediate F

A solution of 2-bromo-3-thiophene carboxylic acid (3.35 g, 16.2 mmol) in methanol (50 mL) was cooling to 0° C. and saturated with gaseous HCl. The solution was heated to 60° C. overnight, then concentrated in vacuo. The residue was redissolved in EtOAc, washed with saturated aqueous sodium bicarbonate and brine, dried over sodium sulfate, filtered, and concentrated, providing methyl 2-bromothiophene-3-carboxylate as yellow oil. LRMS m/z (M+H) 221.1 found, 221.0 required.

A solution of methyl 2-bromothiophene-3-carboxylate (1.74 g, 7.87 mmol), 2-(tributylstannyl)pyrimidine (4.36 g, 11.81 mmol), cesium fluoride (4.78 g, 31.5 mmol), and copper(I) iodide (0.450 g, 2.36 mmol) in DMF (16 mL) in a pressure vessel was purged subsurface with nitrogen and treated with palladium tetrakis (0.455 g, 0.394 mmol). The mixture was sealed and heated at 120° C. overnight. The reaction was partitioned between EtOAc and water and filtered through celite. The organic layer was washed with saturated aqueous sodium bicarbonate and brine, dried over MgSO$_4$, filtered, and concentrated. The residue was purified by silica gel gradient chromatography (0-30% EtOAc in hexanes), providing methyl 2-(pyrimidin-2-yl)thiophene-3-carboxylate as a yellow solid. LRMS m/z (M+H) 221.2 found, 221.1 required.

A solution of methyl 2-(pyrimidin-2-yl)thiophene-3-carboxylate (0.695 g, 3.16 mmol) and potassium trimethylsilanolate (0.506 g, 3.94 mmol) in THF (16 mL) was stirred at RT overnight, then diluted with ether and filtered through a glass frit. The solids were washed with ether, and the filtrate was concentrated, providing the title compound as a beige solid. LRMS m/z (M+H) 207.3 found, 207.1 required.

Intermediate G

4-[1,2,3]Triazol-2-yl-thiophene-3-carboxylic Acid

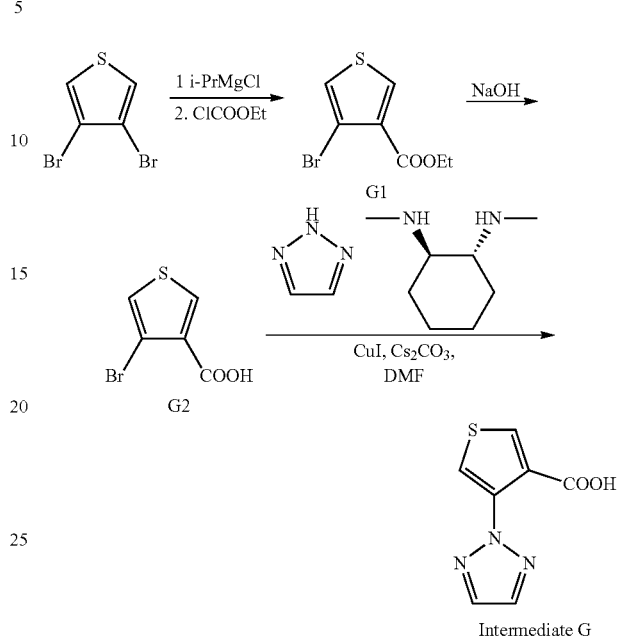

Intermediate G

Step 1: 4-Bromo-thiophene-3-carboxylic Acid Ethyl Ester (G1)

To a solution of 3,4-dibromothiophene (30 g, 0.12 mol) in THF (200 mL) at 0° C. was added i-PrMgCl (2.0 M solution in THF, 77 mL, 0.15 mol), keeping the temperature below 5° C. The resulting mixture was stirred at 0-5° C. for 5 h, ethyl chloroformate (14.4 mL, 0.15 mol) added dropwise with <10° C. and the resulting mixture warmed to RT, stirred overnight and quenched with the sat aqueous NH$_4$Cl. Most of the THF was then removed in vacuo, water added and the mixture extracted with EtOAc (80 mL×4). The combined organic layers were dried over Na$_2$SO$_4$, filtered, the filtrate concentrated in vacuo and the crude product purified by chromatography on silica (Petroleum ether:EtOAc=300:1) to provide the title compound (21 g) as a brown oil.

Step 2: 4-Bromo-thiophene-3-carboxylic Acid (G2)

To a solution of the product from step 1 (10 g, 43 mmol) in methanol (60 mL) was added sodium hydroxide (3.4 g, 86 mmol) and water (1 mL) and the mixture was stirred at RT overnight. The mixture was concentrated in vacuo, the residue diluted with water (30 mL) and extracted with EtOAc (25 mL×4). The pH of aqueous layer was adjusted to ~3 with 1M HCl and the aqueous phase extracted with EtOAc (25 mL×4). The combined extracts were dried over Na$_2$SO$_4$, filtered and the filtrate concentrated in vacuo to provide the title compound (7.9 g) as a yellow solid. LRMS m/z (M+H) 206.9, 208.9 found, 206.9, 208.9 required.

Step 3: 4-[1,2,3]Triazol-2-yl-thiophene-3-carboxylic Acid (Intermediate G)

To a mixture of the product from step 2 (7.9 g, 38 mmol), Cs$_2$CO$_3$ (24.8 g, 76 mmol) and CuI (2.88 g, 7.6 mmol) in DMF (200 mL) were added 2H-[1,2,3]triazole (5.24 g, 76 mmol) and N,N'-dimethyl-cyclohexane-1,2-diamine (0.9 g, 6.5 mmol) and the mixture was stirred at 110° C. overnight. The cooling mixture was adjusted to ~pH12 with 1M sodium hydroxide and extracted with EtOAc (50 mL×3). The aqueous layer was adjusted to pH 4 with 1M HCl and extracted with EtOAc (50 mL×4). The extracts was dried over $Na_2SO_4$, filtered, the filtrate concentrated in vacuo and the residue purified by chromatography on silica (Petroleum ether:EtOAc=10:1) to provide the title compound (4.1 g). LRMS m/z (M+H) 196.0 found, 196.0 required.

Intermediate H

4-Fluoro-2-(2H-1,2,3-triazol-2-yl)benzoic Acid

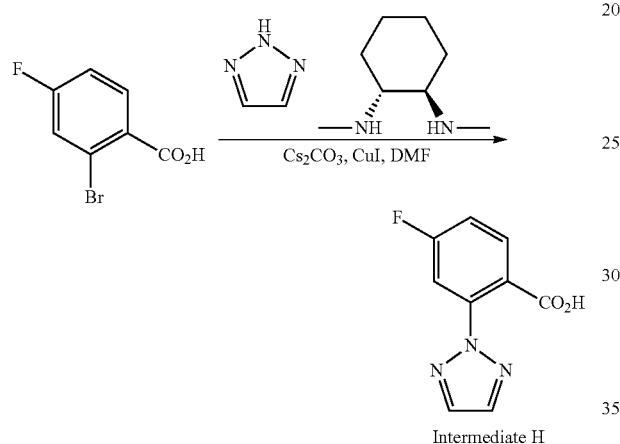

Intermediate H

To a mixture of 2-bromo-4-fluorobenzoic acid (30 g, 137 mmol), cesium carbonate (89.26 g, 274 mmol) and CuI (5.27 g, 27.4 mmol) in DMF (200 mL) were added N,N'-dimethylcyclohexane-1,2-diamine (3.7 mL, 23.3 mmol) and 1H-1,2,3-triazole (18.92 g, 274 mmol). The resulting mixture was stirred at 110° C. overnight, cooling, concentrated in vacuo and diluted with water (150 mL). The aqueous layer was extracted with EtOAc (300 mL×3). The aqueous layer was acidified with 2N HCl and extracted with EtOAc (300 mL×4). The combined organic layers were washed with brine (150 mL×3), dried over $Na_2SO_4$, filtered and the filtrate concentrated in vacuo. The residue was purified by chromatography on silica gel (petroleum ether:EtOAc=100:1~5:1) to provide the title compound (18.13 g) as a yellow solid. LRMS m/z (M+H) 208.0 found, 208.0 required.

Intermediates I, J, K

3-Fluoro-2-(2H-1,2,3-triazol-2-yl)benzoic Acid
5-Fluoro-2-(2H-1,2,3-triazol-2-yl)benzoic Acid
6-Fluoro-2-(2H-1,2,3-triazol-2-yl)benzoic Acid Intermediates I, J, K were prepared in a similar manner to that described for Intermediate H, replacing 2-bromo-4-fluorobenzoic acid with the appropriate bromo or iodo substituted fluorobenzoic acids.

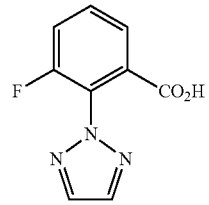

Intermediate I

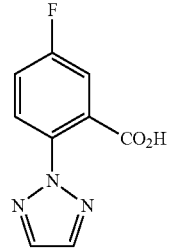

Intermediate J

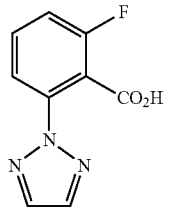

Intermediate K

Intermediate L 2-(1H-Pyrazol-1-yl)nicotinic Acid

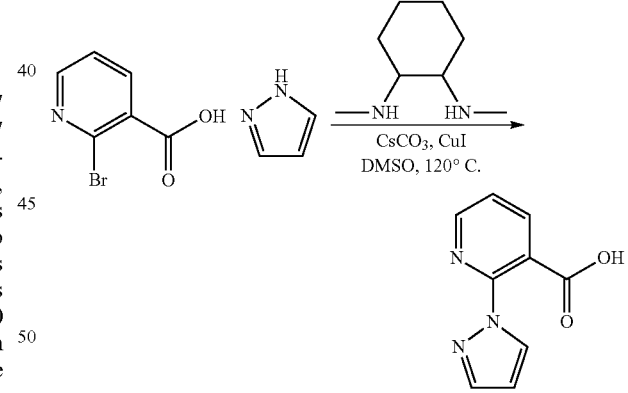

Step 1: 2-(1H-Pyrazol-1-yl)nicotinic Acid

To a solution of 2-bromonicotinic acid (1.4 g, 6.93 mmol) in DMSO (14 mL) was added 1H-pyrazole (0.707 g, 10.40 mmol), cesium carbonate (4.74 g, 14.55 mmol), copper(I) iodide (0.132 g, 0.693 mmol), and N1,N2-dimethylcyclohexane-1,2-diamine (0.099 g, 0.693 mmol). The mixture was sparged with nitrogen and heated at 120° C. overnight. The cooling reaction mixture was diluted with 1 N NaOH (15 mL) and washed with EtOAc (15 mL). The aqueous layer was acidified with 12 N HCl and extracted with EtOAc (4×20 mL). The combined organic layers were washed with brine, dried over $NaSO_4$, filtered, and the solvent was evaporated in vacuo. The crude material was purified by silica gel gradient chromatography [0-100% (5% AcOH in EtOAc)/hexanes]. The purified fractions were combined and azetroped with toluene (3×100 mL) to give 2-(1H-pyrazol-1-yl)nicotinic acid as a white solid. LSMS m/z (M+H) found, required.

Intermediate M 3-(Pyridin-2-yl)pyrazine-2-carboxylic Acid

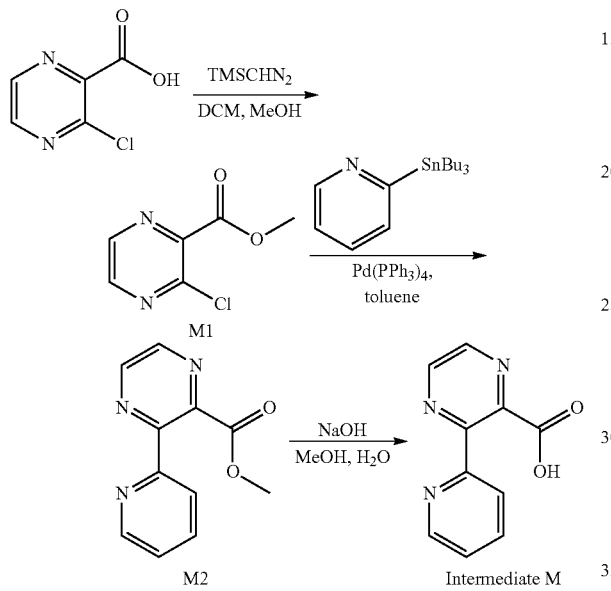

Step 1: methyl 3-chloropyrazine-2-carboxylate (M1)

To a solution of 3-chloropyrazine-2-carboxylic acid (100 mg, 0.63 mmol) in DCM/MeOH (2 mL:0.2 mL) was added TMSCHN$_2$ (0.47 mL, 0.95 mmol) at RT and the resulting mixture stirred at RT for 2 h. Acetic acid (0.2 mL) was added and the mixture diluted with water (2 mL) and extracted with DCM (4 mL×3). The combined organic layers were washed with brine, dried over Na$_2$SO$_4$, filtered and concentrated in vacuo to give the title compound (100 mg) as a colorless oil. LRMS m/z (M+H) 173.0 found, 173.0 required.

Step 2: Methyl 3-(pyridin-2-yl)pyrazine-2-carboxylate (M2)

To a solution of the product from step 1 (100 mg, 0.58 mmol) in toluene (2 mL) was added Pd(PPh$_3$)$_4$ (134 mg, 0.12 mmol) and 2-(tributylstannyl)pyridine (213 mg, 0.58 mmol) at room temperature and the resulting mixture heated to 100° C. overnight. After cooling to RT, the mixture was filtered and 5 mL of aq. KF solution was added to the filtrate. The resulting mixture was stirred for 30 mins and extracted with EtOAc (5 mL×3). The combined organic layers were washed with brine, dried over Na$_2$SO$_4$, filtered and concentrated in vacuo. The residue was purified by chromatography (30% EtOAc in petroleum ether) to provide the title compound (50 mg) as a colorless oil. LRMS m/z (M+H) 216.1 found, 216.1 required.

Step 3: 3-(Pyridin-2-yl)pyrazine-2-carboxylic Acid (Intermediate M)

A solution of the product from step 2 (50 mg, 0.23 mmol) and NaOH (27.8 mg, 0.69 mmol) in 2 mL of methanol and 0.1 mL of water was stirred at RT overnight. After adjusting to pH=5 with 1N HCl, the mixture was concentrated in vacuo. The residue was dissolved in EtOAc (8 mL), stirred for 10 mins and filtered. The filtrate was concentrated in vacuum to give the title compound (36 mg) as a white solid. LRMS m/z (M+H) 202.1 found, 202.1 required.

Intermediate N 2-(2,2-Difluoroethoxy)nicotinic Acid

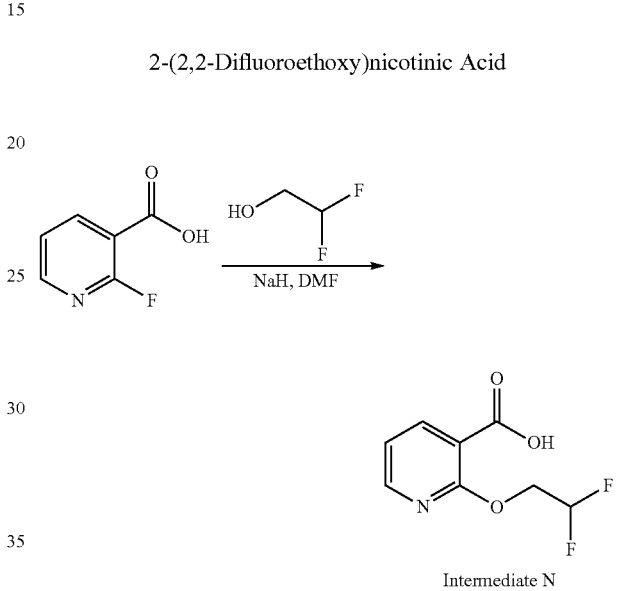

To a suspension of 2,2-difluoroethanol (492 mg, 6.0 mmol) in DMF (10 mL) at 0° C. was added NaH (180 mg, 4.5 mmol), and the mixture stirred at 0° C. for 0.5 h. A suspension of 2-fluoronicotinic acid (423 mg, 3.0 mmol) and NaH (180 mg, 4.5 mmol) in DMF (5 mL) was added dropwise at 0° C. and the resulting mixture stirred at RT overnight. The mixture was diluted with water, acidified to pH-3 with 1M HCl and extracted with EtOAc (50 mL×3). The combined organic layers were washed with brine, dried over MgSO$_4$, filtered, and concentrated in vacuo to give the crude product 2 (350 mg) which was used directly without any further purification. LRMS m/z (M+H) 204.1 found, 204.0 required.

The following intermediates were made as described above, replacing 2,2-difluoroethanol with the appropriate alcohol Intermediate O

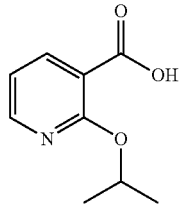

Intermediate P

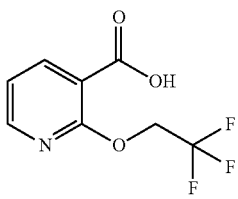

Example 1

(2-(2H-1,2,3-triazol-2-yl)phenyl)((2R,5R)-5-(imidazo[1,2-a]pyrazin-8-yloxy)-2-methylpiperidin-1-yl)methanone

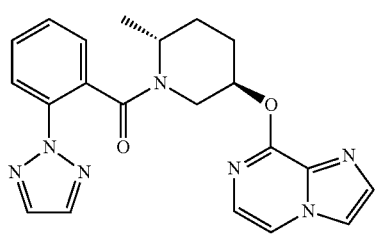 [SMILES: C[C@@H]1CC[C@@H](Oc2nccn3ccnc23)CN1C(=O)c1ccccc1-n1nccn1]

Scheme for the Preparation of Example 1

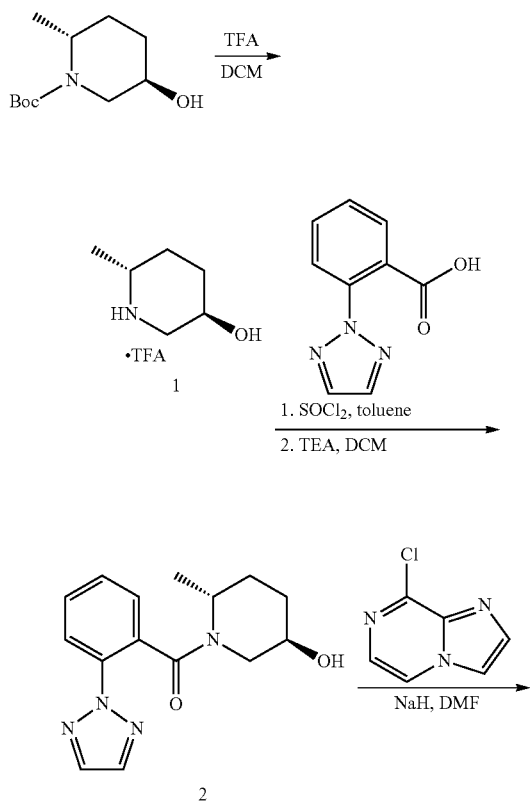

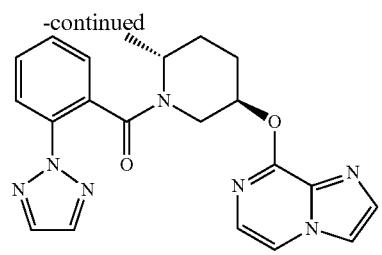

Example 1

Step 1: (3R,6R)-6-methylpiperidin-3-ol TFA Salt (1)

To a solution of (2R,5R)-tert-butyl 5-hydroxy-2-methylpiperidine-1-carboxylate (2.6 g, 12.1 mmol) in DCM (20 mL) was added with TFA (10 mL) at RT. The resulting mixture was stirred at RT for 3 hours, then concentrated in vacuo to give the title compound (1.9 g) as colorless oil. LRMS m/z (M+H) 116.1 found, 116.1 required.

Step 2: (2-(2H-1,2,3-triazol-2-yl)phenyl)((2R,5R)-5-hydroxy-2-methylpiperidin-1-yl)methanone (2)

To a solution of 2-(2H-1,2,3-triazol-2-yl)benzoic acid (1.0 g, 5.3 mmol) in toluene (10 mL) was added with $SOCl_2$ (0.77 mL, 10.6 mmol) at RT. The resulting mixture was stirred for 1 h at 80° C. After cooling to RT, the mixture was concentrated in vacuo to give colorless oil. This oil was dissolved in 6 mL of DCM and was added to a solution of the product from step 1 (1.0 g, 4.7 mmol) in DCM (6 mL). TEA (2.2 mL, 15.9 mmol) was added dropwise at 0° C. The mixture was stirred at this temperature for 30 min. The mixture was concentrated and the residue was purified by chromatography on silica (33% EtOAc in petroleum ether) to give the title compound (1.3 g) as a white solid. LRMS m/z (M+H) 287.1 found, 287.1 required.

Step 3: (2-(2H-1,2,3-triazol-2-yl)phenyl)((2R,5R)-5-(imidazo[1,2-a]pyrazin-8-yloxy)-2-methylpiperidin-1-yl)methanone (Example 1)

To a solution of the product form step 2 (82.9 mg, 0.29 mmol) in DMF (5 mL) was added NaH (14.0 mg, 0.35 mmol, 60 wt % in oil) at RT. The mixture was stirred at RT for 30 minutes, then 8-chloroimidazo[1,2-a]pyrazine (45.9 mg, 0.30 mmol) was added. The resulting mixture was heated to 40° C. for 2.5 hr. After cooling to RT, the mixture was poured into water (5 mL) and extracted with EtOAc (5 mL×3). The combined organic layer was washed with brine, dried over $MgSO_4$, filtered and concentrated in vacuo. The residue was purified by Prep-HPLC to afford the title compound (60 mg) as a brown solid. LRMS m/z (M+H) 404.1 found, 404.1 required.

Example 2

((2R,5R)-5-(imidazo[1,2-a]pyrazin-8-yloxy)-2-methylpiperidin-1-yl)(2-((methylsulfonyl)methyl)phenyl)methanone

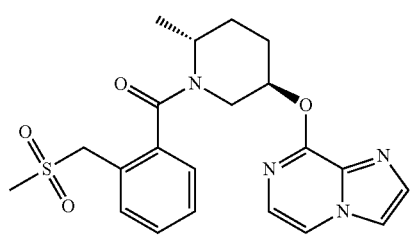 [SMILES: C[C@@H]1CC[C@@H](Oc2nccn3ccnc23)CN1C(=O)c1ccccc1CS(C)(=O)=O]

Scheme for the Preparation of Example 2

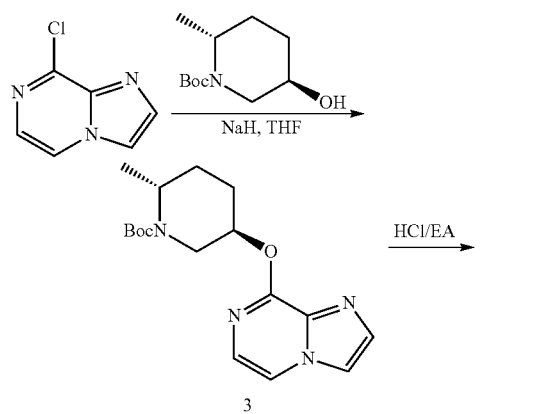

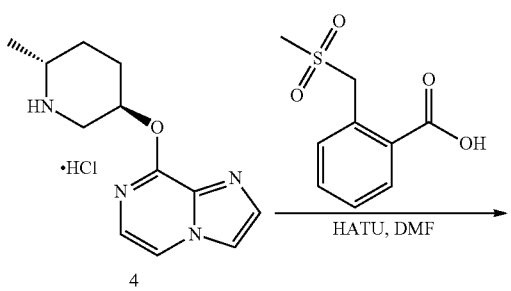

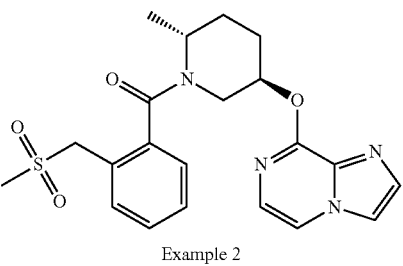

Example 2

Step 1: (2R,5R)-tert-butyl 5-(imidazo[1,2-a]pyrazin-8-yloxy)-2-methylpiperidine-1-carboxylate (3)

To a solution of (2R,5R)-tert-butyl 5-hydroxy-2-methylpiperidine-1-carboxylate (279 mg, 1.3 mmol) in THF (10 mL) was added NaH (64 mg, 1.6 mmol) at RT. The mixture was refluxed for 1 hour, then 8-chloroimidazo[1,2-a]pyrazine (215 mg, 1.4 mmol) was added. The resulting mixture was refluxed for 30 minutes. After TLC (75% EtOAc in petroleum ether) indicated that starting material disappeared, the mixture was cooling to RT, poured into water (10 mL) and extracted with EtOAc (10 mL×3). The combined organic layer was washed with water (10 mL) and brine (10 mL), dried over anhydrous sodium sulfate, filtered and concentrated in vacuo. The residue was purified by chromatography on silica (10% EtOAc in petroleum ether) to give the title compound (300 mg) as a white solid. LRMS m/z (M+H) 333.2 found, 333.2 required.

Step 2: 8-(((3R,6R)-6-methylpiperidin-3-yl)oxy)imidazo[1,2-a]pyrazine HCl Salt (4)

A solution of the product from step 1 (49.9 mg, 0.15 mmol) in HCl/EtOAc (2 mL, 4 N) was stirred at RT for 50 minutes. TLC (66% EtOAc in petroleum ether) indicated that starting material disappeared; the mixture was concentrated in vacuo to give the title compound (35 mg) as a white solid. LRMS m/z (M+H) 233.2 found, 233.2 required.

Step 3: ((2R,5R)-5-(imidazo[1,2-a]pyrazin-8-yloxy)-2-methylpiperidin-1-yl)(2-((methylsulfonyl)methyl)phenyl)methanone (Example 2)

A solution of the product from step 2 (40.3 mg, 0.15 mmol), 2-((methylsulfonyl)methyl)benzoic acid (32.1 mg, 0.15 mmol) and HATU (114 mg, 0.30 mmol) in DMF/TEA (3 mL/0.5 mL) was stirred at RT overnight. LCMS indicated that starting material disappeared. The mixture was purified by Prep-HPLC to give the title compound (33.9 mg) as a white solid. LRMS m/z (M+H) 429.2 found, 429.2 required.

The following compounds were prepared according to the general procedure provided in Example 2 and the procedures herein. The starting materials are either commercially available or may be prepared from commercially available reagents using conventional reactions well known in the art.

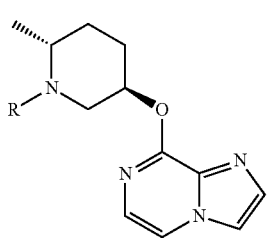

TABLE 1

| Example | R | Chemical Name | LRMS or HRMS (M + H⁺) |
|---|---|---|---|
| 3 | 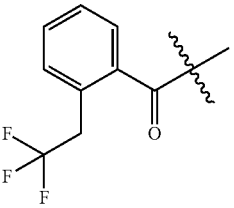 [SMILES: *C(=O)c1ccccc1CC(F)(F)F] | ((2R,5R)-5-(imidazo[1,2-α]pyrazin-8-yloxy)-2-methylpiperidin-1-yl)(2-(2,2,2-trifluoroethyl)phenyl)methanone | Calc'd 419.1, found 419.1 |

Example 4

((2R,5R)-5-(imidazo[1,2-a]pyrazin-8-yloxy)-2-methylpiperidin-1-yl)(2-propylphenyl)methanone Scheme for the Preparation of Example 4

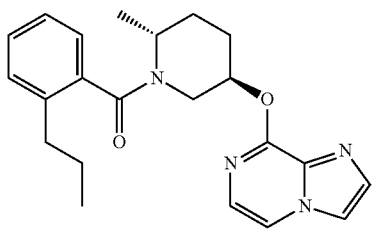 [SMILES: CCCc1ccccc1C(=O)N1C[C@H](Oc2nccn3ccnc23)CC[C@H]1C]

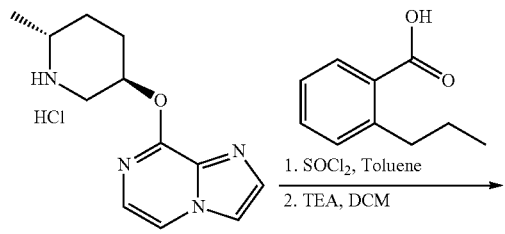

Example 4

Step 1: ((2R,5R)-5-(imidazo[1,2-a]pyrazin-8-yloxy)-2-methylpiperidin-1-yl)(2-propylphenyl)methanone (Example 4)

A mixture of 2-propylbenzoic acid (120 mg, 0.73 mmol) and SOCl₂ (6 mL) in toluene (6 mL) was refluxed for 3 hours. After cooling to RT, the mixture was concentrated in vacuo. The residue was dissolved in anhydrous DCM (2 mL). This solution was added to a solution of 8-((3R,6R)-6-methylpiperidin-3-yloxy)imidazo[1,2-a]pyrazine (196 mg, 0.73 mmol) and TEA, (152 mg, 1.5 mmol) in DCM (5 mL). The resulting mixture was stirred at RT for 1.5 hrs. LCMS indicated that starting material disappeared, then the mixture was quenched with water (0.5 mL) and concentrated in vacuo. The residue was purified by Prep-HPLC to give the title compound (74.3 mg) as a white solid. LRMS m/z (M+H) 379.2 found, 379.2 required.

Example 5

(2-(2H-1,2,3-triazol-2-yl)phenyl)((2R,5R)-5-(imidazo[1,2-a]pyrazin-8-ylthio)-2-methylpiperidin-1-yl)methanone

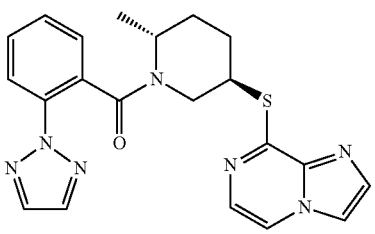 [SMILES: C[C@@H]1CC[C@@H](Sc2nccn3ccnc23)CN1C(=O)c1ccccc1-n1nccn1]

Scheme for the Preparation of Example 5

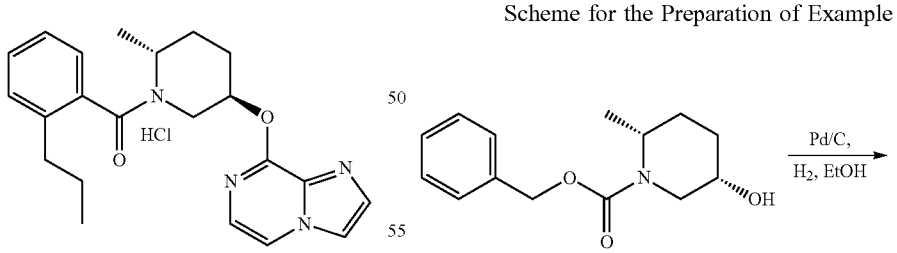

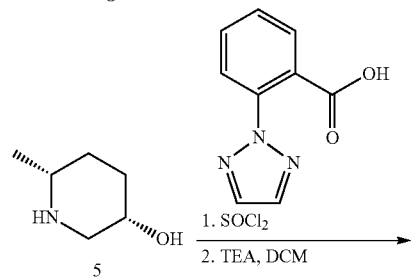

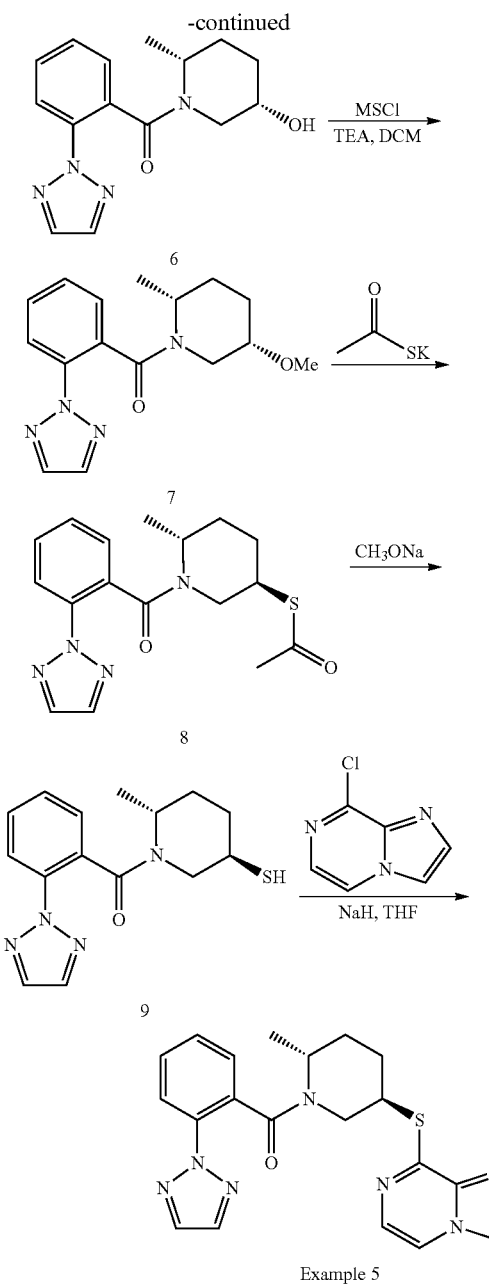

Example 5

Step 1: (3S,6R)-6-methylpiperidin-3-ol (5)

To a solution of (2R,5S)-benzyl 5-hydroxy-2-methylpiperidine-1-carboxylate (5.0 g, 20.1 mmol) in MeOH was added with Pd/C (1.0 g, 10 wt %) at RT. The mixture was stirred at RT for 3 hours under an atmosphere of hydrogen gas. The mixture was filtered and the filtrate was concentrated in vacuo to give the title compound (2.2 g) as colorless oil, which was used directly without purification. LRMS m/z 116.1 (M+H) found, 116.1 required.

Step 2: (2-(2H-1,2,3-triazol-2-yl)phenyl)((2R,5S)-5-hydroxy-2-methylpiperidin-1-yl)methanone (6)

A mixture of 2-(2H-1,2,3-triazol-2-yl)benzoic acid (4.2 g, 22.2 mmol) and $SOCl_2$ (10 mL) in toluene (50 mL) was refluxed for 3 hours. The mixture was concentrated in vacuo. The residue was dissolved in anhydrous DCM (30 mL). This solution was added to a solution of the product from step 1 (2.2 g, 19.1 mmol) and $Et_3N$ (3.9 g, 38.2 mmol) in DCM (100 mL) at 0° C. under $N_2$. The mixture was stirred at 0° C. for 1 hour. The mixture was diluted with water (200 mL) and extracted with DCM (100 mL×3). The organic layer was combined, dried over $Na_2SO_4$, filtered, and concentrated in vacuo. The residue was purified by silica gel gradient chromatography (50% EtOAc in petroleum ether) to give the title compound (4.9 g) as white solid. LRMS m/z (M+H) 287.1 found, 287.1 required.

Step 3: (3S,6R)-1-(2-(2H-1,2,3-triazol-2-yl)benzoyl)-6-methylpiperidin-3-yl methanesulfonate (7)

To a solution of the product from step 2 (600 mg, 2.1 mmol) in DCM (20 mL) was added TEA (424 mg, 4.2 mmol) dropwise at 0° C. under $N_2$ atmosphere. Then methanesulfonyl chloride (355 mg, 3.1 mmol) was added dropwise at 0° C. The resulting solution was stirred at 0° C. for 2 hours. TLC showed the reaction was completed; the mixture was quenched with water (10 mL) and extracted with DCM (20 mL×3). The combined organic phase was washed with brine (10 mL), dried over sodium sulfate, filtered and concentrated in vacuo to give the title compound (764 mg) as colorless oil. LRMS m/z (M+H) 365.1 found, 365.1 required.

Step 4: S-((3R,6R)-1-(2-(2H-1,2,3-triazol-2-yl)benzoyl)-6-methylpiperidin-3-yl) ethanethioate (8)

To a solution of the product from step 3 (130 mg, 0.36 mmol) in DMF (4 mL) was added potassium ethanethioate (80.9 mg, 0.71 mmol) at RT. The mixture was stirred at 80° C. under $N_2$ overnight. Then the mixture was quenched with water (10 mL) and extracted with EtOAc (10 mL×3). The combined organic layer was wished with brine, dried over $Na_2SO_4$, filtered and concentrated in vacuo, and the residue was purified by preparative-TLC (40% EtOAc in petroleum) to give the title compound (90 mg) as yellow oil. LRMS m/z (M+H) 345.2 found, 345.2 required.

Step 5: (2-(2H-1,2,3-triazol-2-yl)phenyl)((2R,5R)-5-mercapto-2-methylpiperidin-1-yl)methanone (9)

To a solution of the product from step 4 (89.4 mg, 0.26 mmol) in MeOH (5 mL) was added sodium methoxide (16.7 mg, 0.31 mmol) at RT. The mixture was stirred at RT under $N_2$ for 1 hour. Then the mixture was diluted with water (5 mL) and extracted with EtOAc (5 mL×3). The combined organic layer was dried over $Na_2SO_4$, filtered and concentrated in vacuo to give the title compound (50 mg) as yellow oil. LRMS m/z (M+H) 303.2 found, 303.2 required.

Step 6: (2-(2H-1,2,3-triazol-2-yl)phenyl)((2R,5R)-5-(imidazo[1,2-a]pyrazin-8-ylthio)-2-methylpiperidin-1-yl)methanone (Example 5)

To a stirred solution of the product from step 5 (51.3 mg, 0.17 mmol) in THF (5 mL) was added NaH (20.4 mg, 0.51 mmol, 60 wt % in oil) at 0° C. The mixture was stirred at 0° C. for 0.5 hour, then 8-chloroimidazo[1,2-a]pyrazine (78.0 mg, 0.51 mmol) was added. The resulting mixture was stirred at RT for 2 hours and then quenched with water (2 mL), extracted with EtOAc (3×5 mL). The combined organic layer was wished with brine, dried over $Na_2SO_4$, filtered and concentrated in vacuo, and the residue was purified by Prep-HPLC to give title compound (28.6 mg) as colorless oil. LRMS m/z (M+H) 420.2 found, 420.2 required.

Example 6

(2-(2H-1,2,3-triazol-2-yl)phenyl)((2R,5R)-2-methyl-5-((2-methylimidazo[1,2-a]pyrazin-8-yl)oxy)piperidin-1-yl)methanone

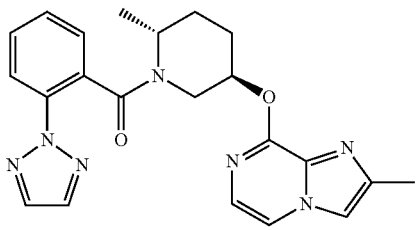 [SMILES: Cc1cn2ccnc(O[C@@H]3CC[C@@H](C)N(C(=O)c4ccccc4-n4nccn4)C3)c2n1]

Scheme for the Preparation of Example 6

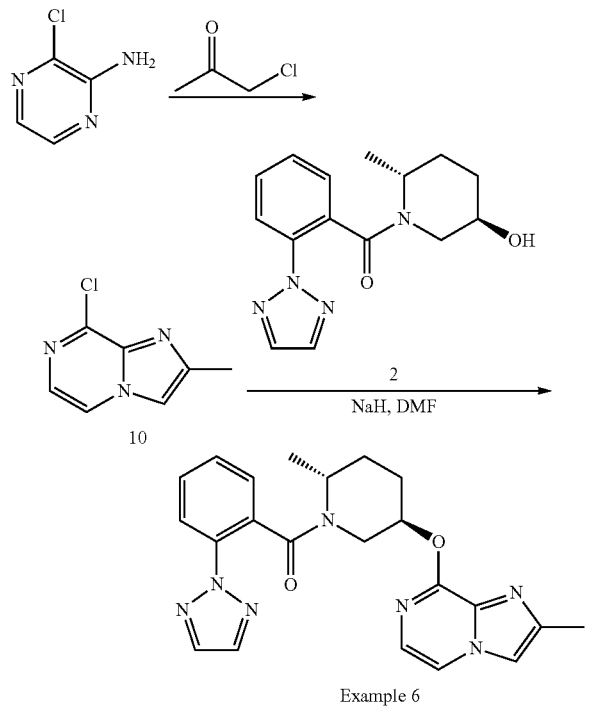

Step 1: 8-chloro-2-methylimidazo[1,2-a]pyrazine hydrobromide (10)

A solution of compound 3-chloropyrazin-2-amine (1.0 g, 7.8 mmol) in 1-chloropropan-2-one (6.5 g, 70.7 mmol) was heated to 90° C. for 16 hours. After it was cooling to RT, ether (10 mL) was added, the solid formed was filtered, washed with ether (10 mL) to give the title compound (1.0 g) as a dark yellow solid. LRMS m/z (M+H) 168.1, 170.1 found, 168.1, 170.1 required.

Step 2: (2-(2H-1,2,3-triazol-2-yl)phenyl)((2R,5R)-2-methyl-5-((2-methylimidazo[1,2-a]pyrazin-8-yl)oxy)piperidin-1-yl)methanone (Example 6)

To a solution of (2-(2H-1,2,3-triazol-2-yl)phenyl)((2R,5R)-5-hydroxy-2-methylpiperidin-1-yl)methanone (109 mg, 0.38 mmol) in DMF (5 mL) was added NaH (22.8 mg, 0.57 mmol, 60 wt % in oil) at RT. The mixture was stirred at RT for 30 minutes, then the product from step 1 (63.7 mg, 0.38 mmol) was added. The mixture was heated to 70° C. for 2.5 hours. After cooling to ET, the mixture was then poured into water (5 mL) and extracted with EtOAc (5 mL×3). The combined organic layer was washed with brine, dried over MgSO₄, filtered and concentrated in vacuo. The residue was purified by Prep-HPLC to afford the title compound (50 mg) as a white solid. LRMS m/z (M+H) 418.1 found, 418.1 required.

Example 7

(2-(2H-1,2,3-triazol-2-yl)thiophen-3-yl)((2R,5R)-2-methyl-5-((2-methylimidazo[1,2-a]pyrazin-8-yl)oxy)piperidin-1-yl)methanone

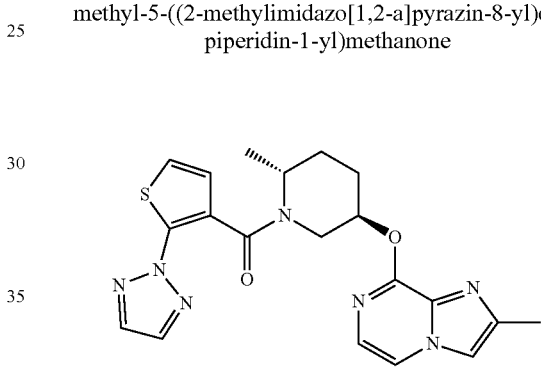

Scheme for the Preparation of Example 7

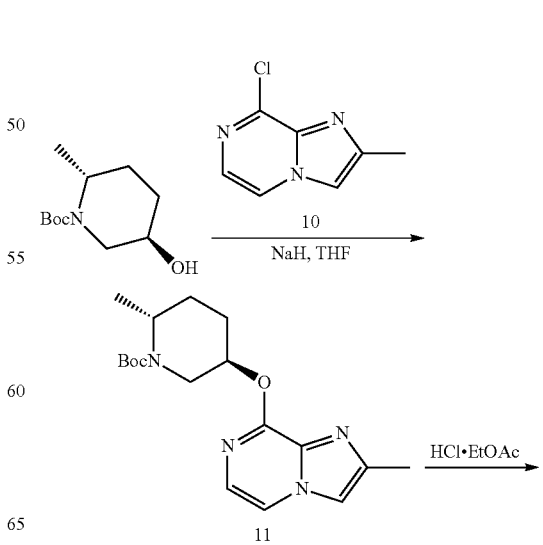

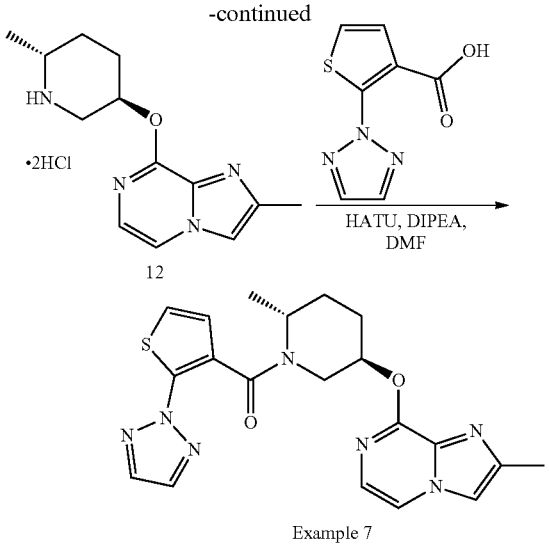

Step 1: (2R,5R)-tert-butyl 2-methyl-5-((2-methyl-imidazo[1,2-a]pyrazin-8-yl)oxy)piperidine-1-carboxylate (11)

To a suspension of NaH (556 mg, 13.9 mmol, 60 wt % in oil) in DMF (10 mL) was added (2S,5R)-tert-butyl 5-hydroxy-2-methylpiperidine-1-carboxylate (1.0 g, 4.7 mmol) under nitrogen at RT. The mixture was stirred at RT for 1 hour, then a solution of 8-chloro-2-methylimidazo[1,2-a]pyrazine (1.5 g, 8.9 mmol) was added. The mixture was stirred at RT for 3 hours, quenched with 20 mL of water and extracted with DCM (20 mL×3). The combined organic layer was dried over anhydrous sodium sulfate, filtered and concentrated in vacuo to give the title compound (0.6 g) as a light yellow solid. LRMS m/z (M+H) 347.1 found, 347.1 required.

Step 2: 2-methyl-8-(((3R,6R)-6-methylpiperidin-3-yl)oxy)imidazo[1,2-a]pyrazine hydrochloride (12)

A solution of the product from step 1 (589 mg, 1.7 mmol) in HCl/EtOAc (20 mL, 4N) was stirred at RT for 1 hour. The mixture was concentrated in vacuo to give the title compound (550 mg) as a pale solid, which was used for the next step without further purification. LRMS m/z (M+H) 247.1 found, 247.1 required.

Step 3: (2-(2H-1,2,3-triazol-2-yl)thiophen-3-yl)((2R,5R)-2-methyl-5-((2-methylimidazo[1,2-a]pyrazin-8-yl)oxy)piperidin-1-yl)methanone (Example 7)

A solution of the product from step 2 (38 mg, 0.12 mmol), 2-(2H-1,2,3-triazol-2-yl) benzoic acid (23 mg, 0.12 mmol), HATU (53 mg, 0.14 mmol) and DIPEA (61 mg, 0.47 mmol) in dry DMF (2 mL) was stirred at RT overnight. The mixture was filtered, and the filtrate was purified by Prep-HPLC to give the title compound (21.8 mg) as a white solid. LRMS m/z (M+H) 424.1 found, 424.1 required.

The following compounds were prepared according to the general procedure provided in Example 7 and the procures herein. The starting materials are either commercially available or may be prepared from commercially available reagents using conventional reactions well known in the art.

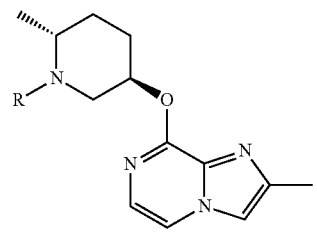

TABLE 2

| Example | R | Chemical Name | LRMS or HRMS (M + H⁺) |
|---|---|---|---|
| 8 | (thiophene with triazole, carbonyl linker) | (4-(2H-1,2,3-triazol-2-yl)thiophen-3-yl)((2R,5R)-2-methyl-5-((2-methylimidazo[1,2-α]pyrazin-8-yl)oxy)piperidin-1-yl)methanone | Calc'd 424.1, found 424.1 |
| 9 | (phenyl with cyclopropanecarbonitrile, carbonyl linker) | 1-(2-((2R,5R)-2-methyl-5-((2-methylimidazo[1,2-α]pyrazin-8-yl)oxy)piperidine-1-carbonyl)phenyl)cyclopropanecarbonitrile | Calc'd 416.1, found 416.1 |

TABLE 2-continued

| Example | R | Chemical Name | LRMS or HRMS (M + H+) |
|---|---|---|---|
| 10 | *(4-fluorophenyl with 2H-1,2,3-triazol-2-yl substituent, carbonyl)* | (4-fluoro-2-(2H-1,2,3-triazol-2-yl)phenyl)((2R,5R)-2-methyl-5-((2-methylimidazo[1,2-a]pyrazin-8-yl)oxy)piperidin-1-yl)methanone | Calc'd 436.1, found 436.1 |
| 11 | *(phenyl with 2H-tetrazol-2-yl substituent, carbonyl)* | (2-(2H-tetrazol-2-yl)phenyl)((2R,5R)-2-methyl-5-((2-methylimidazo[1,2-a]pyrazin-8-yl)oxy)piperidin-1-yl)methanone | Calc'd 419.1, found 419.1 |
| 12 | *(phenyl with ((methylsulfonyl)methyl) substituent, carbonyl)* | ((2R,5R)-2-methyl-5-((2-methylimidazo[1,2-a]pyrazin-8-yl)oxy)piperidin-1-yl)(2-((methylsulfonyl)methyl)phenyl)methanone | Calc'd 443.1, found 443.1 |

Example 13

((2R,5R)-2-methyl-5-((2-methylimidazo[1,2-a]pyrazin-8-yl)oxy)piperidin-1-yl)(4-(pyrimidin-2-yl)thiophen-3-yl)methanone

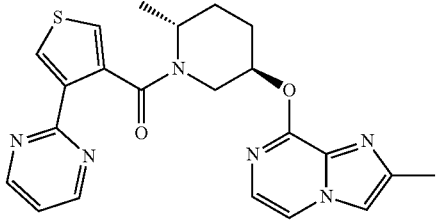 [SMILES: Cc1cn2ccnc(O[C@@H]3CC[C@@H](C)N(C(=O)c4cscc4-c4ncccn4)C3)c2n1]

Scheme for the Preparation of Example 13

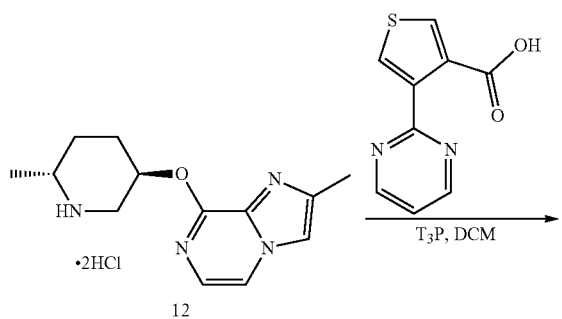

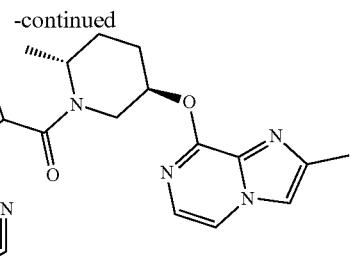

Example 13

Step 1: ((2R,5R)-2-methyl-5-((2-methylimidazo[1,2-a]pyrazin-8-yl)oxy)piperidin-1-yl)(4-(pyrimidin-2-yl)thiophen-3-yl)methanone (Example 13)

To a solution of 2-methyl-8-((3R,6R)-6-methylpiperidin-3-yloxy)imidazo[1,2-a]pyrazine HCl salt (38 mg, 0.12 mmol) and 4-(pyrimidin-2-yl) thiophene-3-carboxylic acid (24 mg, 0.12 mmol) in dry DCM (2 mL) was added T$_3$P (2 mL). The resulting mixture was stirred at 50° C. overnight. After cooling to RT, the mixture was filtered, and the filtrate was concentrated in vacuo. The residue was purified by Prep-HPLC to give the title compound (4.13 mg) as a white solid. LRMS m/z (M+H) 435.1 found, 435.1 required.

The following compounds were prepared according to the general procedure provided in Example 13 and the procedures herein. The starting materials are either commercially available or may be prepared from commercially available reagents using conventional reactions well known in the art.

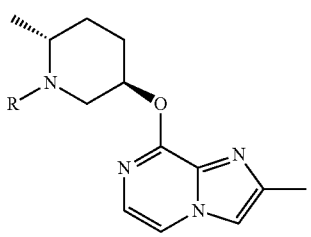

TABLE 3

| Example | R | Chemical Name | LRMS or HRMS (M + H+) |
|---|---|---|---|
| 14 | 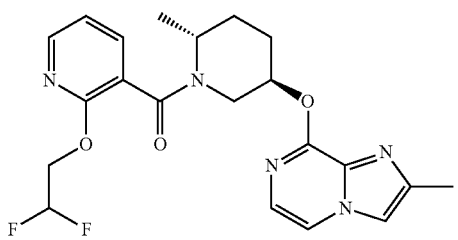 | ((2R,5R)-2-methyl-5-((2-methylimidazo[1,2-α]pyrazin-8-yl)oxy)piperidin-1-yl)(2-(pyrimidin-2-yl)thiophen-3-yl)methanone | Calc'd 435.1, found 435.1 |

Example 15

(2-(2,2-difluoroethoxy)pyridin-3-yl)((2R,5R)-2-methyl-5-((2-methylimidazo[1,2-a]pyrazin-8-yl)oxy)piperidin-1-yl)methanone

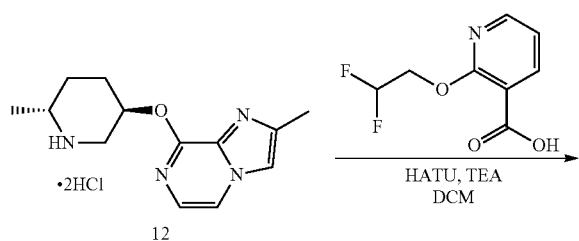

Scheme for the Preparation of Example 15

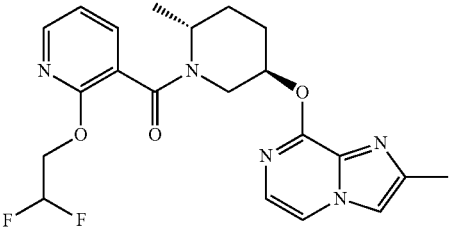

Example 15

Step 1: (2-(2,2-difluoroethoxy)pyridin-3-yl)((2R,5R)-2-methyl-5-((2-methylimidazo[1,2-a]pyrazin-8-yl)oxy)piperidin-1-yl)methanone (Example 15)

A solution of 2-methyl-8-((3R,6R)-6-methylpiperidin-3-yloxy)imidazo[1,2-a]pyrazine (38 mg, 0.12 mmol), 2-(2,2-difluoroethoxy) nicotinic acid (37 mg, 0.18 mmol), HATU (68 mg, 0.18 mmol) and TEA (0.2 mL) in DCM (5 mL) was stirred at RT overnight. The mixture was filtered, and the filtrate was concentrated in vacuo. The residue was purified by Prep-HPLC to give the title compound (25.5 mg) as a white solid. LRMS m/z (M+H) 432.1 found, 432.1 required.

The following compounds were prepared according to the general procedure provided in Example 15 and the procedures herein. The starting materials are either commercially available or may be prepared from commercially available reagents using conventional reactions well known in the art.

TABLE 4

| Example | R | Chemical Name | LRMS or HRMS (M + H+) |
|---|---|---|---|
| 16 | (2-(2,2,2-trifluoroethoxy)pyridin-3-yl structure) | ((2R,5R)-2-methyl-5-((2-methylimidazo[1,2-α]pyrazin-8-yl)oxy)piperidin-1-yl)(2-(2,2,2-trifluoroethoxy)pyridin-3-yl)methanone | Calc'd 450.1, found 450.1 |
| 17 | (2-phenylpyridin-3-yl structure) | ((2R,5R)-2-methyl-5-((2-methylimidazo[1,2-α]pyrazin-8-yl)oxy)piperidin-1-yl)(2-phenylpyridin-3-yl)methanone | Calc'd 428.1, found 428.1 |

TABLE 4-continued

| Example | R | Chemical Name | LRMS or HRMS (M + H⁺) |
|---|---|---|---|
| 18 | 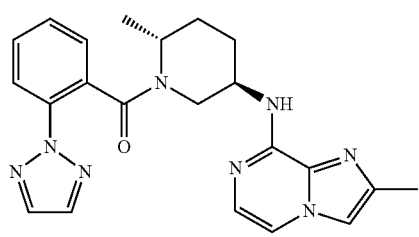 | (2-(1H-pyrazol-1-yl)pyridin-3-yl)((2R,5R)-2-methyl-5-((2-methylimidazo[1,2-α]pyrazin-8-yl)oxy)piperidin-1-yl)methanone | Calc'd 418.1, found 418.1 |

Example 19

(2-(2H-1,2,3-triazol-2-yl)phenyl)((2R,5R)-2-methyl-5-((2-methylimidazo[1,2-a]pyrazin-8-yl)amino)piperidin-1-yl)methanone

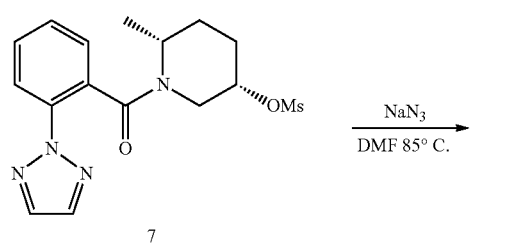

Scheme for the Preparation of Example 19

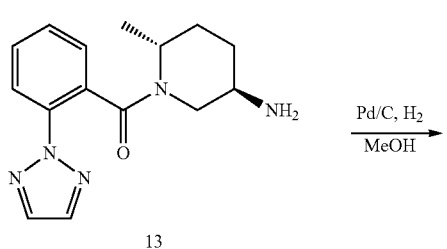

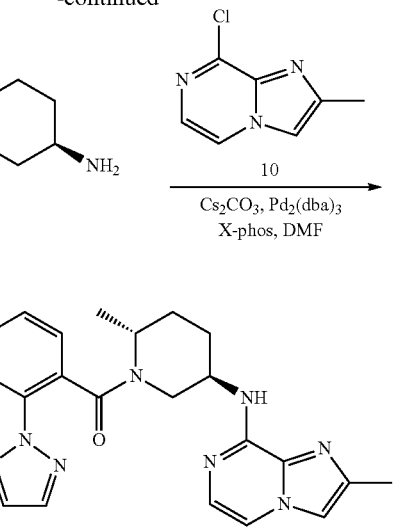

Example 19

Step 1: (2-(2H-1,2,3-triazol-2-yl)phenyl)((2R,5R)-5-azido-2-methylpiperidin-1-yl)methanone (13)

A mixture of (3S,6R)-1-(2-(2H-1,2,3-triazol-2-yl)benzoyl)-6-methylpiperidin-3-yl methanesulfonate (14 g, 38.5 mmol) and NaN₃ (3.7 g, 57.0 mmol) in DMF (100 mL) was heated to 80° C. overnight. After cooling to RT, the mixture was poured into water (80 mL) and extracted with EtOAc (70 mL×3). The combined organic layer was washed with water (70 mL) and brine (50 mL), dried over anhydrous sodium sulfate, filtered and concentrated in vacuo. The residue was purified by chromatography on silica (16% EtOAc in DCM) to give the title compound (10.5 g) as a white solid. LRMS m/z (M+H) 312.2 found, 312.2 required.

Step 2: (2-(2H-1,2,3-triazol-2-yl)phenyl)((2R,5R)-5-amino-2-methylpiperidin-1-yl)methanone (14)

A solution of the product from step 1 (17 g, 54.7 mmol) in MeOH (300 mL) was hydrogenated with Pd/C under 20 Psi of H₂ pressure at RT for 4 hours. After LCMS indicated that starting material disappeared, the reaction mixture was filtered through celite pad and the filtrate was concentrated in vacuo. The residue was purified by chromatography on silica (25% EtOAc in DCM) to give the title compound (12.6 g) as a yellow solid. LRMS m/z (M+H) 286.2 found, 286.2 required.

Step 3: (2-(2H-1,2,3-triazol-2-yl)phenyl)((2R,5R)-2-methyl-5-((2-methylimidazo[1,2-a]pyrazin-8-yl)amino)piperidin-1-yl)methanone (Example 19)

To a mixture of product from step 2 (51.3 mg, 0.18 mmol), 8-chloro-2-methylimidazo[1,2-a]pyrazine (30 mg, 0.18 mmol), Cs₂CO₃ (114 mg, 0.35 mmol), and X-phos (10 mg) in DMF (3 mL) was added Pd₂(dba)₃ (8 mg). The mixture was heated to 100° C. under N₂ protection overnight. LCMS indicated that starting material disappeared, the mixture was filtered, and the filtrate was purified by Prep-HPLC to give the title compound (10.0 mg) as yellow oil. LRMS m/z (M+H) 417.1 found, 417.1 required.

Example 20

(2-(2H-1,2,3-triazol-2-yl)phenyl)((2R,5R)-5-((2-isopropylimidazo[1,2-a]pyrazin-8-yl)oxy)-2-methylpiperidin-1-yl)methanone

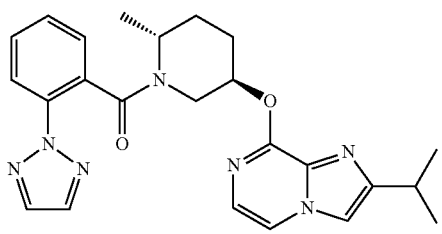 [SMILES: CC(C)c1cn2ccnc(O[C@@H]3CC[C@@H](C)N(C(=O)c4ccccc4-n4nccn4)C3)c2n1]

Scheme for the Preparation of Example 20

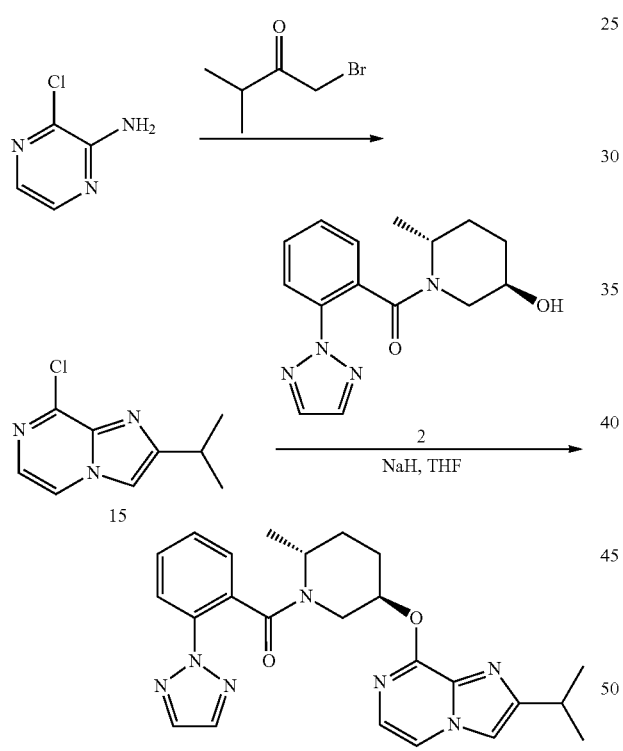

Example 20

Step 1: 8-chloro-2-isopropylimidazo[1,2-a]pyrazine (15)

A solution of 3-chloropyrazin-2-amine (1.0 g, 7.8 mmol) and 1-bromo-3-methylbutan-2-one (1.9 g, 11.5 mmol) in EtOH (5 mL) was refluxed overnight. LCMS indicated that starting material disappeared. The mixture was concentrated, and the residue was purified by Prep-HPLC to give the title compound (40 mg) as a yellow solid. LRMS m/z (M+H) 196.1, 198.1 found, 196.1, 198.1 required.

Step 2: (2-(2H-1,2,3-triazol-2-yl)phenyl)((2R,5R)-5-((2-isopropylimidazo[1,2-a]pyrazin-8-yl)oxy)-2-methylpiperidin-1-yl)methanone (Example 20)

To a solution of (2-(2H-1,2,3-triazol-2-yl)phenyl)((2R,5R)-5-hydroxy-2-methylpiperidin-1-yl)methanone (50 mg, 0.17 mmol) in THF (3 mL) was added NaH (10.4 mg, 0.26 mmol, 60 wt % in oil) at RT. The mixture was refluxed for 2 hour, then the product from step 1 (33 mg, 0.17 mmol) in THF (1 mL) was added. The resulting mixture was refluxed for 0.5 hours. LCMS indicated that starting material disappeared, and the mixture was poured into water (5 mL) and extracted with EtOAc (5 mL×3). The combined organic layer was washed with water (5 mL) and brine (5 mL), dried over anhydrous sodium sulfate, filtered and concentrated in vacuo. The residue was purified by Prep-HPLC to give the title compound (20 mg) as a white solid. LRMS m/z (M+H) 446.1 found, 446.1 required.

Example 21

(2-(2H-1,2,3-triazol-2-yl)phenyl)((2R,5R)-2-methyl-5-((2-(trifluoromethyl)imidazo[1,2-a]pyrazin-8-yl)oxy)piperidin-1-yl)methanone

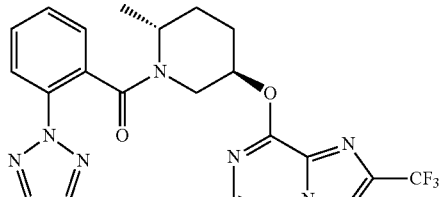

Scheme for the preparation of example 21

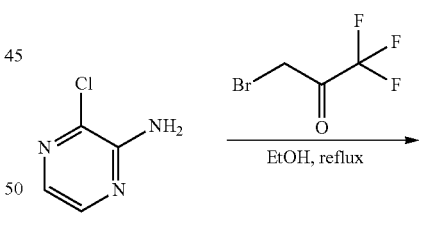

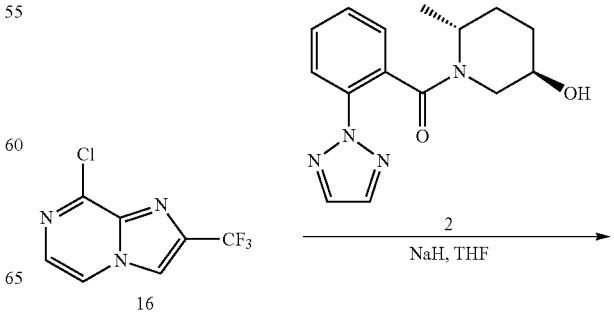

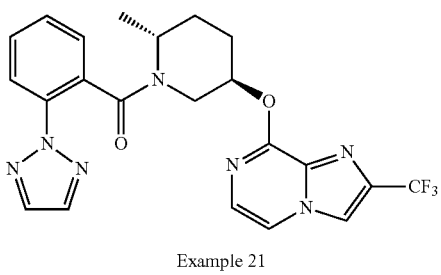

Example 21

Step 1: 8-chloro-2-(trifluoromethyl)imidazo[1,2-a]pyrazine (16)

To a solution of 3-chloropyrazin-2-amine (1.0 g, 7.7 mmol) in andyhrous EtOH was added 3-bromo-1,1,1-trifluoropropan-2-one (1.6 g, 8.5 mmol). The mixture was refluxed overnight. After cooling to RT, the mixture was concentrated in vacuo and purified by Prep-HPLC to afford the title compound (100 mg) as white solid. LRMS m/z (M+H) 222.1, 224.1 found, 222.1, 224.1 required.

Step 2: (2-(2H-1,2,3-triazol-2-yl)phenyl)((2R,5R)-2-methyl-5-((2-(trifluoromethyl)imidazo[1,2-a]pyrazin-8-yl)oxy)piperidin-1-yl)methanone (Example 21)

To a solution of (2-(2H-1,2,3-triazol-2-yl)phenyl)((2R,5R)-5-hydroxy-2-methylpiperidin-1-yl)methanone (84 mg, 0.29 mmol) in THF (5 mL) was added NaH (17 mg, 0.42 mmol, 60 wt % in oil) at RT. The mixture was stirred at RT for 30 minutes, then the product from step 1 (66 mg, 0.3 mmol) was added. The mixture was heated to 60° C. for 3 hours. After cooling to RT, the mixture was then poured into water (5 mL) and extracted with EtOAc (5 mL×3). The combined organic layer was washed with brine, dried over MgSO$_4$, filtered and concentrated in vacuo. The residue was purified by Prep-HPLC to afford the title compound (30 mg) as a white solid.

LRMS m/z (M+H) 472.1 found, 472.1 required.

Example 22

(2-(2H-1,2,3-triazol-2-yl)phenyl)((2R,5R)-2-methyl-5-((2-(trifluoromethyl)imidazo[1,2-a]pyrazin-8-yl)amino)piperidin-1-yl)methanone

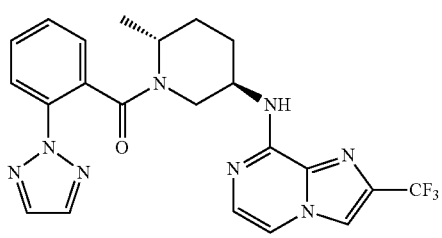 [SMILES: C[C@@H]1CC[C@@H](Nc2nccn3cc(C(F)(F)F)nc23)CN1C(=O)c1ccccc1-n1nccn1]

Scheme for the Preparation of Example 22

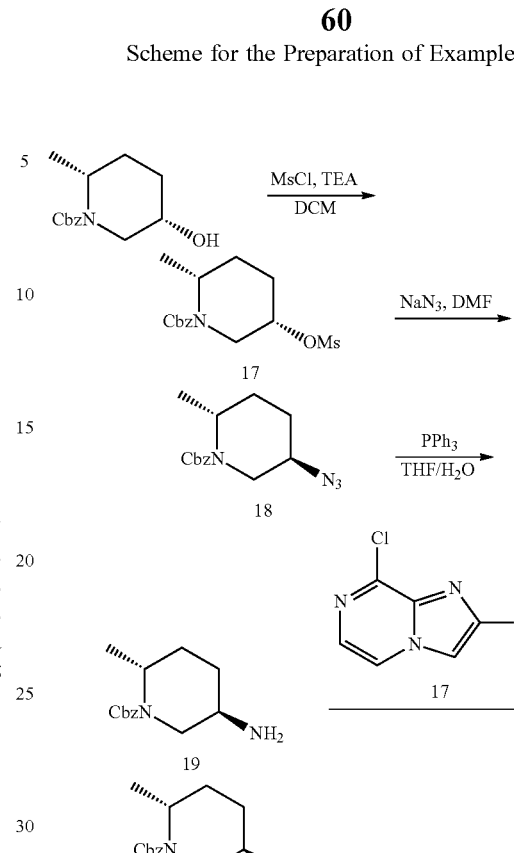

Step 1: (2R,5S)-benzyl 2-methyl-5-((methylsulfonyl)oxy)piperidine-1-carboxylate (17)

To a solution of (2R,5S)-benzyl 5-hydroxy-2-methylpiperidine-1-carboxylate (5.0 g, 20.1 mmol) and TEA (5.1 g, 50.5 mmol) in DCM (60 mL) was added MsCl (3.0 g, 26.3 mmol) at 0° C. The mixture was stirred at 0° C. for 2 hours.

The mixture was poured into water (70 mL), extracted with DCM (50 mL×3). The combined organic layer was washed with water (50 mL) and brine (60 mL), dried over anhydrous sodium sulfate, filtered and concentrated in vacuo to give the title compound (6.5 g) as an orange oil. LRMS m/z (M+H) 328.1 found, 328.1 required.

Step 2: (2R,5R)-benzyl 5-azido-2-methylpiperidine-1-carboxylate (18)

To a solution of the product from step 1 (6.5 g, 20.1 mmol) in DMF (50 mL) was added $NaN_3$ (1.4 g, 21.5 mmol). The mixture was heated to 90° C. overnight. The mixture was cooling to RT, poured into water (60 mL) and extracted with EtOAc (60 mL×3). The combined organic layer was washed with water (50 mL) and brine (60 mL), dried over anhydrous sodium sulfate, filtered and concentrated in vacuo. The residue was purified by chromatography on silica (3% EtOAc in petroleum ether) to give the title compound (5 g) as an orange oil. LRMS m/z (M+H) 275.1 found, 275.1 required.

Step 3: (2R,5R)-benzyl 5-amino-2-methylpiperidine-1-carboxylate (19)

To a solution of the product from step 2 (5.0 g, 18.2 mmol) in $THF/H_2O$ (50 mL/20 mL) was added $PPh_3$ (7.2 g, 27.3 mmol) in portions at 0° C. The mixture was allowed to warm up to RT overnight. TLC (25% EtOAc in petroleum ether) indicated that starting material disappeared. The mixture was concentrated in vacuo. The residue was dissolved in 1N HCl (30 mL) and 30 mL of EtOAc, the mixture was refluxed for 3 hours, and then cooling to RT, poured into water (40 mL), and extracted with EtOAc (40 mL×2). The aqueous phase was basified to pH=8 with $NaHCO_3$ solution, extracted with EtOAc (40 mL×3). The combined organic layer was washed with water (50 mL) and brine (60 mL), dried over anhydrous sodium sulfate, filtered and concentrated in vacuo to give the title compound (1.2 g) as orange oil. LRMS m/z (M+H) 249.1 found, 249.1 required.

Step 4: (2R,5R)-benzyl 2-methyl-5-((2-(trifluoromethyl)imidazo[1,2-a]pyrazin-8-yl)amino)piperidine-1-carboxylate (20)

A solution of the product from step 3 (247 mg, 1.00 mmol) in THF (10 mL) was stirred at RT for 5 minutes, then 8-chloro-2-(trifluoromethyl)imidazo[1,2-a]pyrazine (200 mg, 0.91 mmol) was added. The mixture was heated to 60° C. for 3 hours. After cooling to RT, the mixture was concentrated in vacuo and purified by Prep-HPLC to give the title compound (150 mg) as a white solid. LRMS m/z (M+H) 434.1 found, 434.1 required.

Step 5: N-((3R,6R)-6-methylpiperidin-3-yl)-2-(trifluoromethyl)imidazo[1,2-a]pyrazin-8-amine (21)

To a solution of the product from step 4 (150 mg, 0.35 mmol) in THF (6 mL) was added Pd/C (30 mg) at RT. The mixture was stirred at RT under the 1 atm $H_2$ atmospheres overnight. The mixture was filtered and the filtrate was concentrated in vacuo to give the title compound (100 mg) as yellow oil. LRMS m/z (M+H) 300.1 found, 300.1 required.

Step 6: (2-(2H-1,2,3-triazol-2-yl)phenyl)((2R,5R)-2-methyl-5-((2-(trifluoromethyl)imidazo[1,2-a]pyrazin-8-yl)amino)piperidin-1-yl)methanone (Example 22)

A mixture of the product from step 5 (50 mg, 0.17 mmol), HATU (95 mg, 0.25 mmol), TEA (0.3 mL) and 2-(2H-1,2,3-triazol-2-yl)benzoic acid (34.8 mg, 0.18 mmol) in DMF (2 mL) was stirred at RT for 9 hours under the $N_2$ atmosphere. Then the mixture was poured into water (5 mL×3) and extracted with EtOAc (5 mL×3). The combined organic layer was washed with brine, dried over magnesium sulfate, filtered and concentrated in vacuo. The residue was purified by Prep-HPLC to give the title compound (30 mg) as yellow oil. LRMS m/z (M+H) 471.1 found, 471.1 required.

The following compounds were prepared according to the general procedure provided in Example 22 and the procedures herein. The starting materials are either commercially available or may be prepared from commercially available reagents using conventional reactions well known in the art.

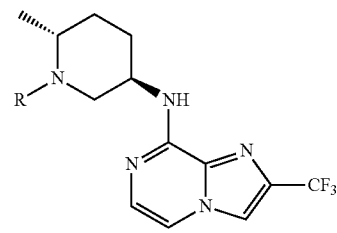

TABLE 5

| Example | R | Chemical Name | LRMS or HRMS (M + H⁺) |
|---|---|---|---|
| 23 | 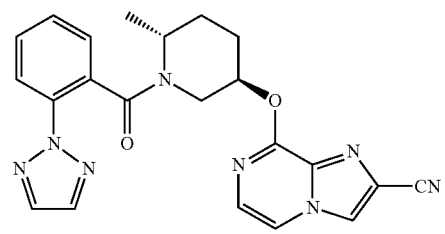 | (2-(2H-1,2,3-triazol-2-yl)thiophen-3-yl)((2R,5R)-2-methyl-5-((2-(trifluoromethyl)imidazo[1,2-α]pyrazin-8-yl)amino)piperidin-1-yl)methanone | Calc'd 477.1, found 477.1 |

Example 24

8-(((3R,6R)-1-(2-(2H-1,2,3-triazol-2-yl)benzoyl)-6-methylpiperidin-3-yl)oxy)imidazo[1,2-a]pyrazine-2-carbonitrile

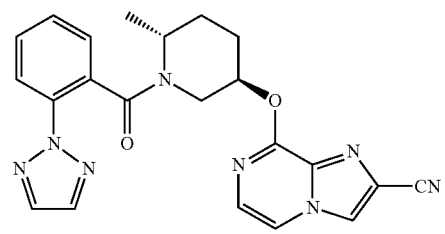 [SMILES: C[C@@H]1CC[C@@H](Oc2nccn3cc(C#N)nc23)CN1C(=O)c1ccccc1-n1nccn1]

63
Scheme for the Preparation of Example 24

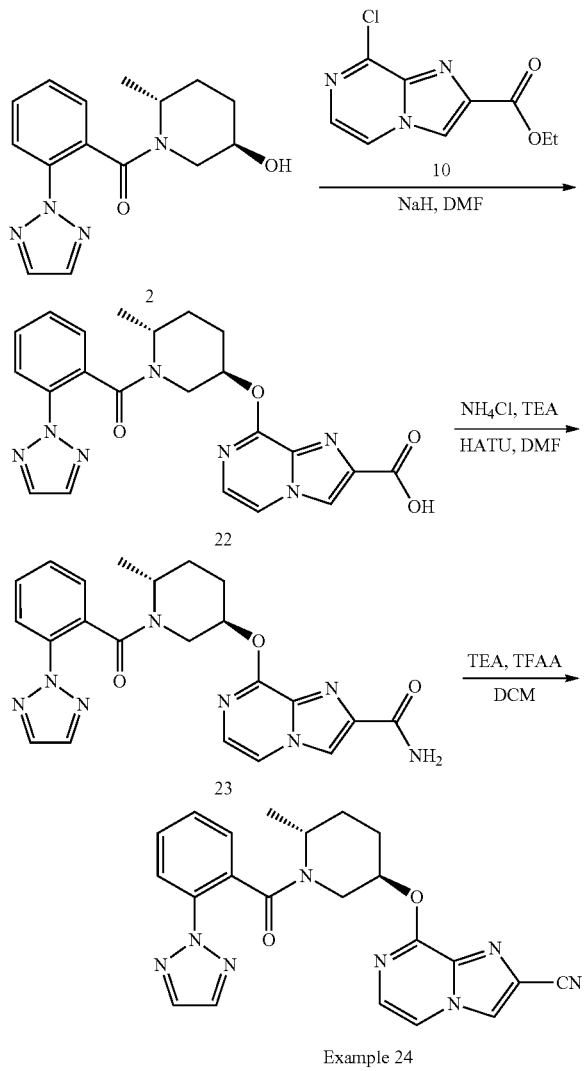

Example 24

Step 1: 8-(((3R,6R)-1-(2-(2H-1,2,3-triazol-2-yl)benzoyl)-6-methylpiperidin-3-yl)oxy)imidazo[1,2-a]pyrazine-2-carboxylic Acid (22)

To a solution of (2-(2H-1,2,3-triazol-2-yl)phenyl)((2R,5R)-5-hydroxy-2-methylpiperidin-1-yl)methanone (100 mg, 0.35 mmol) in DMF (2 mL) was added NaH (20 mg, 0.5 mmol) at RT, then ethyl 8-chloroimidazo[1,2-a]pyrazine-2-carboxylate (63 mg, 0.28 mmol) was added. The mixture was refluxed for 3 hours. LCMS indicated that starting material disappeared, 2 mL of water was added, and then the mixture was stirred at RT for 2 hours. The mixture was poured into water (10 mL) and extracted with EtOAc (10 mL×2). The water phase was adjusted with HCl (4N) to pH=6, extracted with DCM (10 mL×3). The combined organic layer was washed with water (10 mL) and brine (10 mL), dried over anhydrous sodium sulfate, filtered and concentrated in vacuo to give the title compound (60 mg) as yellow oil. LRMS m/z (M+H) 448.1 found, 448.2 required.

64
Step 2: 8-(((3R,6R)-1-(2-(2H-1,2,3-triazol-2-yl)benzoyl)-6-methylpiperidin-3-yl)oxy)imidazo[1,2-a]pyrazine-2-carboxamide (23)

To a solution of the product from step 1 (60 mg, 0.13 mmol) in DMF (2 mL) was added NH$_4$Cl (10 mg, 0.2 mmol), TEA (0.3 mL) and HATU (76 mg, 0.2 mmol) at RT. The mixture was heated to 50° C. overnight. After LCMS indicated that starting material disappeared, the mixture was poured into water (5 mL) and extracted with EtOAc (5 mL×4). The combined organic layer was washed with water (5 mL) and brine (5 mL), dried over anhydrous sodium sulfate, filtered and concentrated in vacuo. The residue was purified by prep.-TLC (petroleum ether:EtOAc=1:3) to give the title compound (46 mg) as a yellow solid. LRMS m/z (M+H) 447.1 found, 447.2 required.

Step 3: 8-(((3R,6R)-1-(2-(2H-1,2,3-triazol-2-yl)benzoyl)-6-methylpiperidin-3-yl)oxy)imidazo[1,2-a]pyrazine-2-carbonitrile (Example 24)

To a solution of the product from step 2 (50 mg, 0.11 mmol) and TEA (20 mg, 0.2 mmol) in DCM (3 mL) was added TFAA (32 mg, 0.15 mmol) at 0° C. The mixture was allowed warm to RT for 5 hours. After LCMS indicated that starting material disappeared, the mixture was concentrated, and the residue was purified by Prep-HPLC to give the title compound (20 mg) as a white solid. LRMS m/z (M+H) 429.1 found, 429.1 required.

Example 25

(2-(2H-1,2,3-triazol-2-yl)phenyl)((2R,5R)-5-((2-(hydroxymethyl)imidazo[1,2-a]pyrazin-8-yl)oxy)-2-methylpiperidin-1-yl)methanone

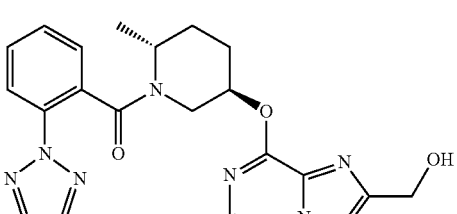

Scheme for the Preparation of Example 25

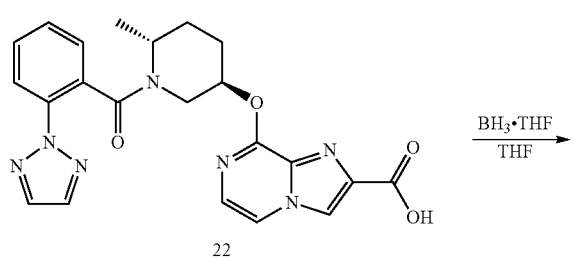

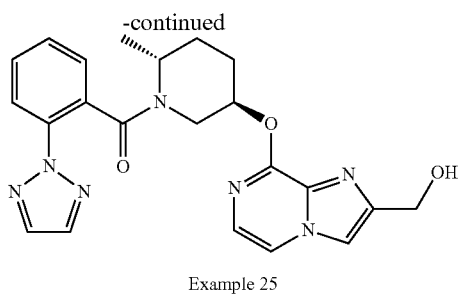

Example 25

(2-(2H-1,2,3-triazol-2-yl)phenyl)((2R,5R)-5-((2-(hydroxymethyl)imidazo[1,2-a]pyrazin-8-yl)oxy)-2-methylpiperidin-1-yl)methanone (Example 25)

To a solution of 8-((3R,6R)-1-(2-(2H-1,2,3-triazol-2-yl)benzoyl)-6-methylpiperidin-3-yloxy)imidazo[1,2-a]pyrazine-2-carboxylic acid (130 mg, 0.29 mmol) in THF (10 mL) was added BH₃.THF (5 mL, 5 mmol) at 0° C. The mixture was allowed to warm up to RT overnight. After LCMS indicated that starting material disappeared, the mixture was concentrated in vacuo. The residue was purified by Prep-HPLC to give the title compound (30 mg) as a white solid. LRMS m/z (M+H) 434.1 found, 434.1 required.

Example 26

(2-(2H-1,2,3-triazol-2-yl)phenyl)((2R,5R)-5-((3-chloroimidazo[1,2-a]pyrazin-8-yl)oxy)-2-methylpiperidin-1-yl)methanone

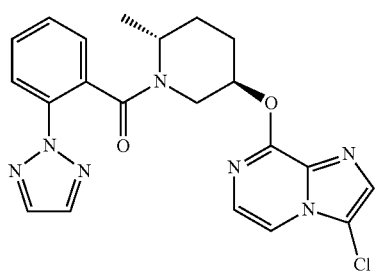 [SMILES: C[C@@H]1CC[C@@H](Oc2nccn3c(Cl)cnc23)CN1C(=O)c1ccccc1-n1nccn1]

Scheme for the Preparation of Example 26

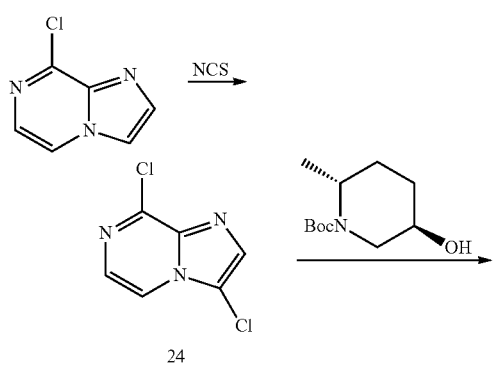

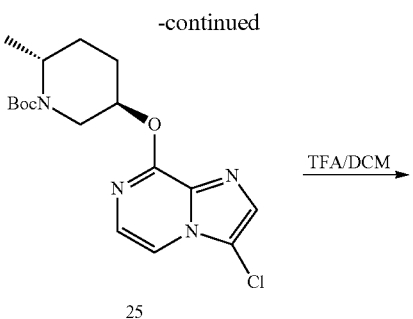

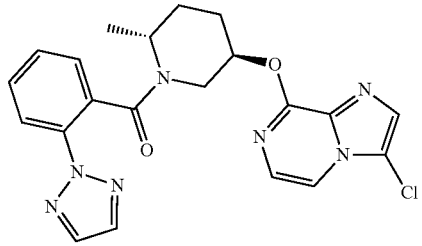

Example 26

Step 1: 3,8-dichloroimidazo[1,2-a]pyrazine (24)

A solution of 8-chloroimidazo[1,2-a]pyrazine (730 mg, 4.8 mmol) and NCS (955 mg, 7.2 mmol) in MeCN/DCE (10 mL/5 mL) was heated to 90° C. overnight. After LCMS indicated that starting material disappeared, the mixture was poured into water (20 mL) and extracted with DCM (20 mL×3). The combined organic layer was washed with water (20 mL) and brine (20 mL), dried over anhydrous sodium sulfate, filtered and concentrated in vacuo. The residue was purified by chromatography on silica (3% EtOAc in petroleum ether) to give the title compound (700 mg) as a yellow solid. LRMS m/z (M+H) 188.1, 190.1 found, 188.1, 190.1 required.

Step 2: (2R,5R)-tert-butyl 5-((3-chloroimidazo[1,2-a]pyrazin-8-yl)oxy)-2-methylpiperidine-1-carboxylate (25)

To a solution of the (2R,5R)-tert-butyl 5-hydroxy-2-methylpiperidine-1-carboxylate (300 mg, 1.4 mmol) in THF (3 mL) was added NaH (67 mg, 1.7 mmol, 60 wt % in oil) at RT. The resulting mixture was refluxed for 2 hour. Then the product from step 1 (320 mg, 1.7 mmol) in THF (3 mL) was added dropwise, the resulting mixture was refluxed for 0.5 hour. After cooling to RT, the mixture was poured into water (10 mL), extracted with EtOAc (10 mL×3). The combined organic layer was washed with water (10 mL) and brine (10 mL), dried over anhydrous Sodium sulfate, filtered and concentrated in vacuo. The residue was purified by chromatography on silica (5% EtOAc in petroleum ether) to give the title compound (300 mg) as orange oil. LRMS m/z (M+H) 367.1, 369.1 found, 367.1, 369.1 required.

Step 3: 3-chloro-8-(((3R,6R)-6-methylpiperidin-3-yl)oxy)imidazo[1,2-a]pyrazine TFA salt (26)

A solution of the product from step 2 (300 mg, 0.82 mmol) in TFA/DCM (2 mL/10 mL) was stirred at RT for 3 hours. LCMS indicated that starting material disappeared; the mixture was concentrated in vacuo to give the title compound (200 mg) as yellow oil. LRMS m/z (M+H) 267.1, 269.1 found, 267.1, 269.1 required.

Step 4: (2-(2H-1,2,3-triazol-2-yl)phenyl)((2R,5R)-5-((3-chloroimidazo[1,2-a]pyrazin-8-yl)oxy)-2-methylpiperidin-1-yl)methanone (Example 26)

A solution of the product from step 3 (72 mg, 0.19 mmol), 2-(2H-1,2,3-triazol-2-yl)benzoic acid (41.6 mg, 0.22 mmol) and HATU (150 mg, 0.39 mmol) in DMF/DIEA (4 mL/0.5 mL) was stirred at RT overnight. After LCMS indicated the reaction completed, the mixture was purified by Prep-HPLC to give the title compound (50 mg) as a white solid. LRMS m/z (M+H) 438.1, 440.1 found, 438.1, 440.1 required.

The following compounds were prepared according to the general procedure provided in Example 26 and the procedures herein. The starting materials are either commercially available or may be prepared from commercially available reagents using conventional reactions well known in the art.

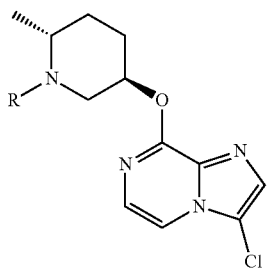

TABLE 6

| Example | R | Chemical Name | LRMS or HRMS (M + H⁺) |
|---|---|---|---|
| 27 | (2-tetrazol-2-yl-phenyl, methyl-carbonyl group) | (2-(2H-tetrazol-2-yl)phenyl)((2R,5R)-5-((3-chloroimidazo[1,2-α]pyrazin-8-yl)oxy)-2-methylpiperidin-1-yl)methanone | Calc'd 439.1, 441.1, found 439.1, 441.1 |
| 28 | (2-(1-cyanocyclopropyl)phenyl, methyl-carbonyl group) | 1-(2-((2R,5R)-5-((3-chloroimidazo[1,2-α]pyrazin-8-yl)oxy)-2-methylpiperidine-1-carbonyl)phenyl)cyclopropanecarbonitrile | Calc'd 436.1, 438.1, found 436.1, 438.1 |
| 29 | (2-(2H-1,2,3-triazol-2-yl)thiophen-3-yl, methyl-carbonyl group) | (2-(2H-1,2,3-triazol-2-yl)thiophen-3-yl)((2R,5R)-5-((3-chloroimidazo[1,2-α]pyrazin-8-yl)oxy)-2-methylpiperidin-1-yl)methanone | Calc'd 444.1, 446.1, found 444.1, 446.1 |

Example 30

(2-(2H-1,2,3-triazol-2-yl)phenyl)((2R,5R)-5-((3-chloroimidazo[1,2-a]pyrazin-8-yl)amino)-2-methylpiperidin-1-yl)methanone

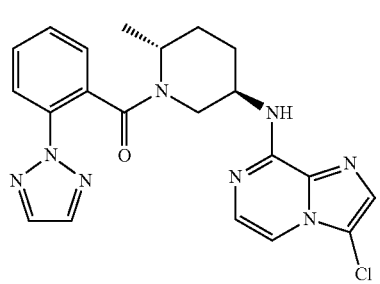

Scheme for the Preparation of Example 30

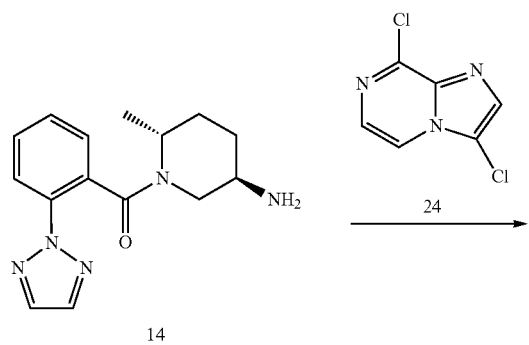

14

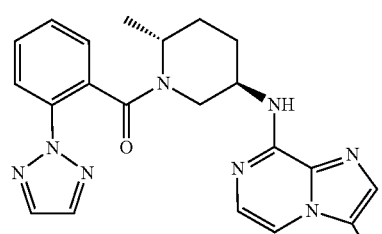

Example 30

(2-(2H-1,2,3-triazol-2-yl)phenyl)((2R,5R)-5-((3-chloroimidazo[1,2-a]pyrazin-8-yl)amino)-2-methyl-piperidin-1-yl)methanone (example 30)

A mixture of compound 14 (example 19, step 2) (50 mg, 0.18 mmol) and compound 24 (example 26, step 1) (40 mg, 0.21 mmol) was heated to 120° C. for 4 hours. LCMS indicated that starting material disappeared; the mixture was purified by Prep-HPLC to give the title compound (30 mg) as a yellow solid. LRMS m/z (M+H) 437.1, 439.1 found, 437.1, 439.1 required.

Example 31

((2R,5R)-5-((3-chloroimidazo[1,2-a]pyrazin-8-yl)amino)-2-methylpiperidin-1-yl)(2-(pyrimidin-2-yl)phenyl)methanone

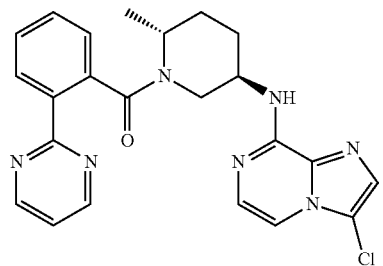 [SMILES: C[C@@H]1CC[C@@H](Nc2nccn3c(Cl)cnc23)CN1C(=O)c1ccccc1-c1ncccn1]

Scheme for the Preparation of Example 31

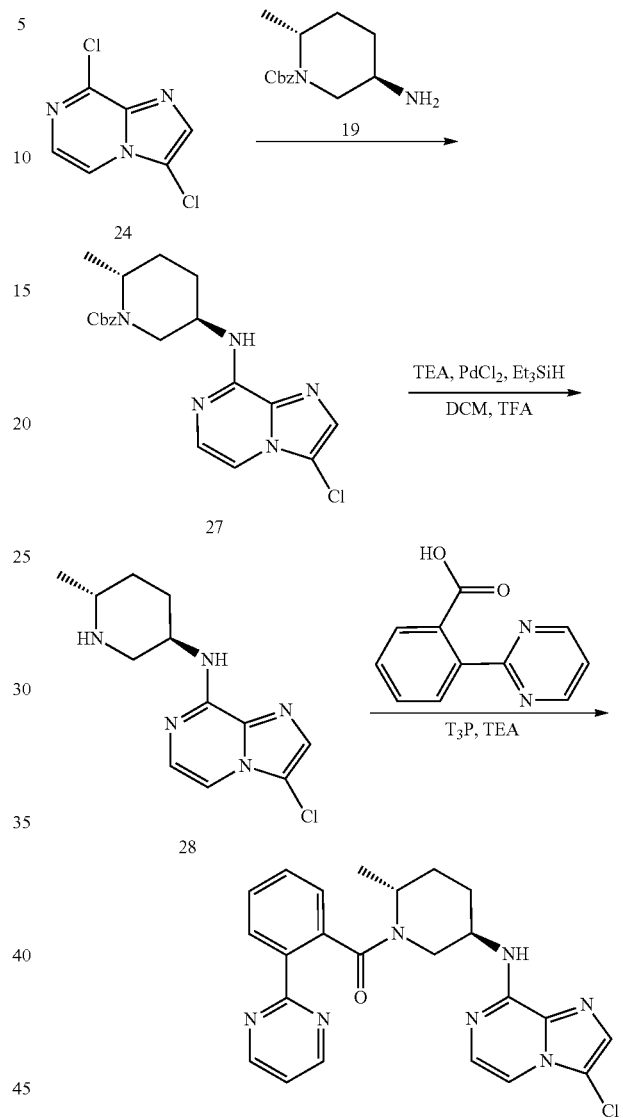

Example 31

Step 1: (2R,5R)-benzyl 5-((3-chloroimidazo[1,2-a]pyrazin-8-yl)amino)-2-methylpiperidine-1-carboxylate (27)

Compound 19 (example 22, step 3) (100 mg, 0.40 mmol) and compound 24 (example 26, step 1) (76 mg, 0.40 mmol) was dissolved in methanol (5 mL). The solvent was removed in vacuo. The residue was heated to 80° C. overnight; LCMS indicated that starting material disappeared. The residue was purified by prep.-TLC (9% MeOH in DCM) to give the title compound (80 mg) as a yellow solid. LRMS m/z (M+H) 400.1, 402.1 found, 400.1, 402.1 required.

Step 2: 3-chloro-N-((3R,6R)-6-methylpiperidin-3-yl)imidazo[1,2-a]pyrazin-8-amine (28)

To a mixture of the product from step 1 (130 mg, 0.32 mmol), TEA (33 mg, 0.32 mmol) and PdCl$_2$ (10 mg) in DCM (2 mL) was added Et₃SiH (74 mg, 0.64 mmol) dropwise. The mixture was stirred at RT for 2 hours, then 0.4 mL of TFA was added. The resulting mixture was stirred for an additional 0.5 hour. After LCMS indicated that starting material disappeared, the mixture was filtered through celite pad. The filtrate was poured into water (10 mL), basified to pH=8 with NaHCO₃ solution, extracted with DCM (10 mL×3). The combined organic layer was washed with water (10 mL) and brine (10 mL), dried over anhydrous sodium sulfate, filtered and concentrated in vacuo. The residue was purified by prep.-TLC (DCM:methanol=10:1) to give the title compound (34 mg) as a yellow residue. LRMS m/z (M+H) 266.1, 268.1 found, 266.1, 268.1 required.

Step 3: ((2R,5R)-5-((3-chloroimidazo[1,2-a]pyrazin-8-yl)amino)-2-methylpiperidin-1-yl)(2-(pyrimidin-2-yl)phenyl)methanone (Example 31)

To a solution of the product from step 2 (30 mg, 0.11 mmol) and 2-(pyrimidin-2-yl)benzoic acid (22 mg, 0.11 mmol) and TEA (0.5 mL) in DCM (5 mL) was added T₃P (0.1 mL) at RT. The resulting mixture was heated to 50° C. overnight. After LCMS indicated that starting material disappeared, the mixture was concentrated in vacuo, and the residue was purified by Prep-HPLC to give the title compound (10 mg) as a brown solid. LRMS m/z (M+H) 448.1, 450.1 found, 448.1, 450.1 required.

Example 32

(2-(2H-1,2,3-triazol-2-yl)phenyl)((2R,5R)-5-((3-fluoroimidazo[1,2-a]pyrazin-8-yl)oxy)-2-methylpiperidin-1-yl)methanone

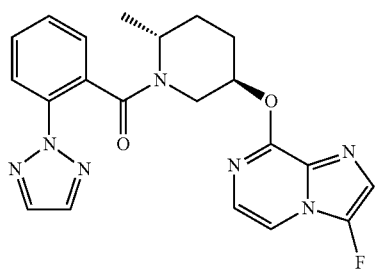 [SMILES: C[C@@H]1CC[C@@H](Oc2nccn3c(F)cnc23)CN1C(=O)c1ccccc1-n1nccn1]

Scheme for the Preparation of Example 32

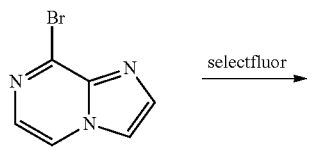

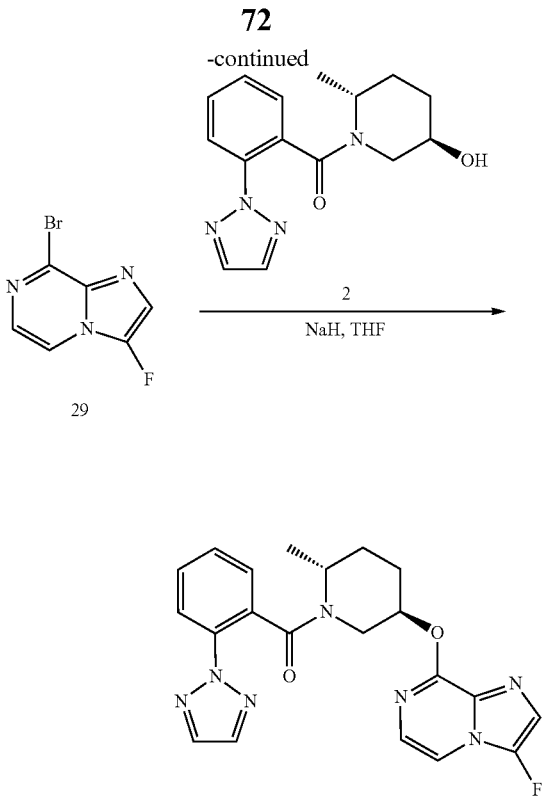

Step 1: 8-bromo-3-fluoroimidazo[1,2-a]pyrazine (29)

A mixture of 8-bromoimidazo[1,2-a]pyrazine (100 mg, 0.51 mmol) and selectfluor (214 mg, 0.61 mmol) in MeCN (5 mL) was heated to 70° C. for 1 hour. After LCMS, it was indicated that starting material disappeared. The mixture was then concentrated, and the residue was purified by Prep-HPLC to give the title compound (40 mg) as a yellow solid. LRMS m/z (M+H) 216.1, 218.1 found, 216.1, 218.1 required.

Step 2: (2-(2H-1,2,3-triazol-2-yl)phenyl)((2R,5R)-5-((3-fluoroimidazo[1,2-a]pyrazin-8-yl)oxy)-2-methylpiperidin-1-yl)methanone (Example 32)

To a solution of compound 2 (example 1, step 2) (50 mg, 0.17 mmol) in THF (3 mL) was added NaH (10 mg, 0.26 mmol, 60 wt % in oil) at RT. The resulting mixture was refluxed for 2 hours. The product from step 1 (38 mg, 0.17 mmol) in THF (1 mL) was added dropwise, the resulting mixture was refluxed for 0.5 hours. After LCMS indicated that starting material disappeared, the mixture was poured into water (5 mL), extracted with EtOAc (5 mL×3). The combined organic layer was washed with water (5 mL) and brine (5 mL), dried over anhydrous sodium sulfate, filtered and concentrated in vacuo. The residue was purified by Prep-HPLC to give the title compound (25 mg) as yellow oil. LRMS m/z (M+H) 422.1 found, 422.1 required.

Example 33

(2-(2H-1,2,3-triazol-2-yl)phenyl)((2R,5R)-5-((3-bromoimidazo[1,2-a]pyrazin-8-yl)oxy)-2-methylpiperidin-1-yl)methanone

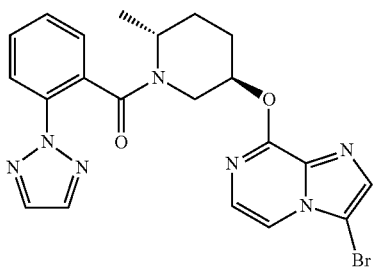

Scheme for the Preparation of Example 33

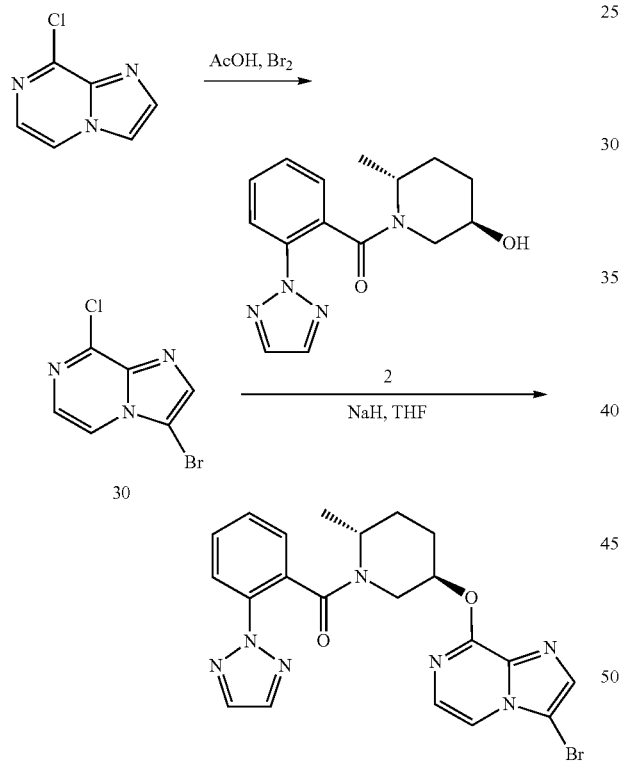

Example 33

Step 1: 3-bromo-8-chloroimidazo[1,2-a]pyrazine (30)

To a mixture of 8-chloroimidazo[1,2-a]pyrazine (500 mg, 3.3 mmol) in AcOH (5 mL) was added $Br_2$ (800 mg, 5.0 mmol) at RT. The resulting mixture was stirred at RT for 2 days, then poured into water (20 mL) and extracted with EtOAc (15 mL×3). The combined organic layer was washed with aqueous sodium bicarbonate solution and brine, dried over $MgSO_4$, filtered and concentrated in vacuo. The residue was purified by chromatography on silica (9-16% EtOAc in petroleum ether) to give the title compound (300 mg) as a yellow solid. LRMS m/z (M+H) 232.2, 234.1 found, 231.2, 234.1 required.

Step 2: (2-(2H-1,2,3-triazol-2-yl)phenyl)((2R,5R)-5-((3-bromoimidazo[1,2-a]pyrazin-8-yl)oxy)-2-methylpiperidin-1-yl)methanone (Example 33)

To a solution of compound 2 (example 1, step 2) (80 mg, 0.28 mmol) in THF (5 mL) was added NaH (22 mg, 0.56 mmol, 60 wt % in oil) at RT. The mixture was stirred at RT for 30 minutes, then the product from step 1 (81 mg, 0.35 mmol) was added. The mixture was heated to 60° C. for 3 hours. After cooling to RT, the mixture was poured into water (5 mL) and extracted with EtOAc (5 mL×3). The combined organic layer was washed with brine, dried over $MgSO_4$, filtered and concentrated in vacuo. The residue was purified by Prep-HPLC to afford the title compound (70 mg) as a white solid. LRMS m/z (M+H) 482.1, 484.1 found, 482.1, 484.1

Example 34

(2-(2H-1,2,3-triazol-2-yl)phenyl)((2R,5R)-2-methyl-5-((3-methylimidazo[1,2-a]pyrazin-8-yl)oxy)piperidin-1-yl)methanone Scheme for the Preparation of Example 41

75

-continued

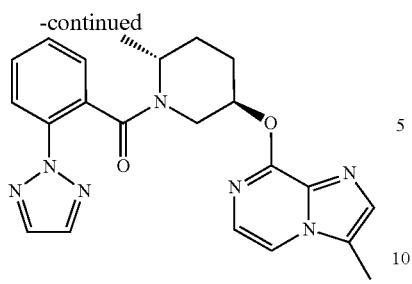

Example 34

(2-(2H-1,2,3-triazol-2-yl) phenyl) ((2R,5R)-5-(4-(2-hydroxypropan-2-yl)thiazol-2-yl)-2-methylpiperidin-1-yl)methanone (Example 34)

To a degassed solution of Example 33 (64 mg, 0.13 mmol) in toluene (5 mL) was added Pd(dppf)Cl$_2$ (10 mg, 0.013 mmol) at RT, followed by AlMe$_3$ (0.1 mL, 0.3 mmol). The mixture was heated to 80° C. for 3 hours, then cooling to RT, poured into water (5 mL) and extracted with EtOAc (5 mL×3). The combined organic layer was washed with brine, dried over MgSO$_4$, filtered and concentrated in vacuo. The residue was purified by Prep-HPLC to afford the title compound (20 mg) as a white solid. LRMS m/z (M+H) 418.2 found, 418.2 required.

Example 35

8-(((3R,6R)-1-(2-(2H-1,2,3-triazol-2-yl)benzoyl)-6-methylpiperidin-3-yl)oxy)imidazo[1,2-a]pyrazine-3-carbonitrile

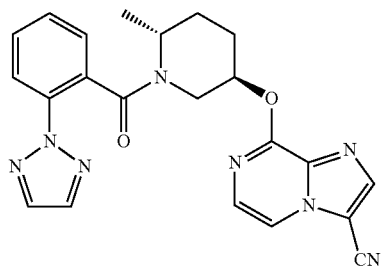 [SMILES: C[C@@H]1CC[C@@H](Oc2nccn3c(C#N)cnc23)CN1C(=O)c1ccccc1-n1nccn1]

Scheme for the Preparation of Example 35

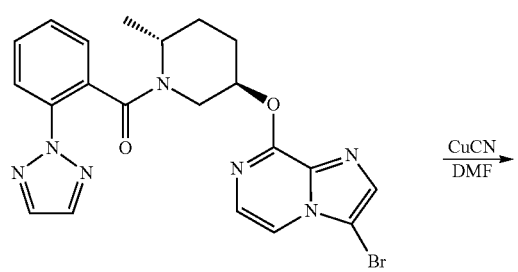

Example 33

76

-continued

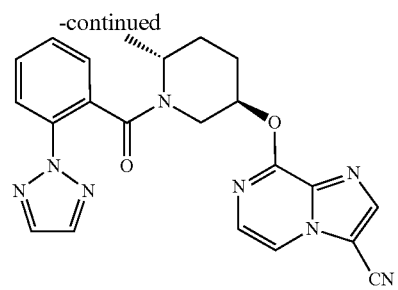

Example 35

8-(((3R,6R)-1-(2-(2H-1,2,3-triazol-2-yl)benzoyl)-6-methylpiperidin-3-yl)oxy)imidazo[1,2-a]pyrazine-3-carbonitrile (Example 35)

A solution of Example 33 (40 mg, 0.082 mmol) and CuCN (8.9 mg, 0.10 mmol) in DMF (3 mL) was treated with microwave at 100° C. for 20 minutes. LCMS indicated that starting material disappeared, the mixture was filtered, and the filtrate was purified by Prep-HPLC to give the title compound (8 mg) as a yellow solid. LRMS m/z (M+H) 429.2 found, 429.2 required.

Example 36

(2-(2H-1,2,3-triazol-2-yl)phenyl)((2R,5R)-2-methyl-5-((3-vinylimidazo[1,2-a]pyrazin-8-yl)oxy)piperidin-1-yl)methanone

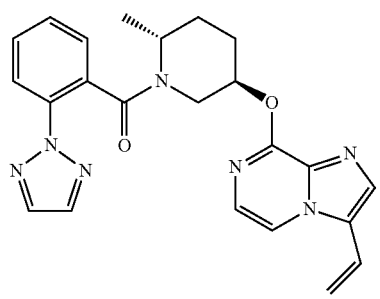 [SMILES: C=Cc1cnc2c(O[C@@H]3CC[C@@H](C)N(C(=O)c4ccccc4-n4nccn4)C3)nccn12]

Scheme for the Preparation of Example 36

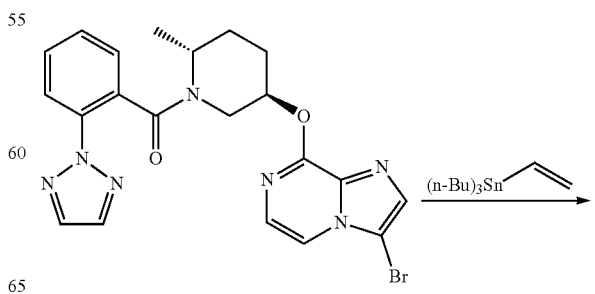

Example 33

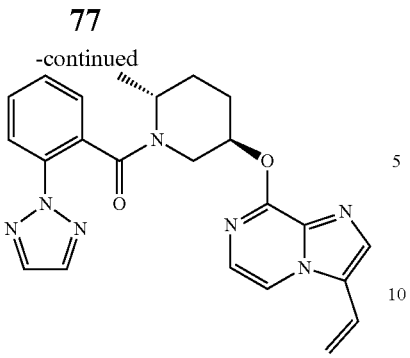

Example 36

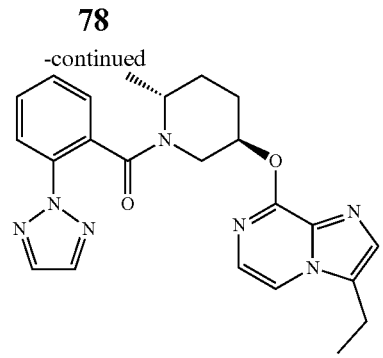

Example 37

(2-(2H-1,2,3-triazol-2-yl)phenyl)((2R,5R)-2-methyl-5-((3-vinylimidazo[1,2-a]pyrazin-8-yl)oxy)piperidin-1-yl)methanone (Example 36)

A solution of Example 33 (150 mg, 0.31 mmol), tributyl (vinyl)stannane (143 mg, 0.45 mmol) and Pd(PPh$_3$)$_2$Cl$_2$ (50 mg) in toluene (5 mL) was refluxed for 3 hours. LCMS indicated that starting material disappeared, the mixture was filtered, and the filtrate was purified by Prep-TLC (66% EtOAc in petroleum ether) to give the title compound (90 mg) as a yellow solid.

LRMS m/z (M+H) 430.1 found, 430.1 required.

Example 37

(2-(2H-1,2,3-triazol-2-yl)phenyl)((2R,5R)-5-((3-ethylimidazo[1,2-a]pyrazin-8-yl)oxy)-2-methylpiperidin-1-yl)methanone (2-(2H-1,2,3-triazol-2-yl)phenyl)((2R,5R)-5-((3-ethylimidazo[1,2-a]pyrazin-8-yl)oxy)-2-methylpiperidin-1-yl)methanone (Example 37)

A mixture of Example 36 (40 mg, 0.09 mmol) in methanol (10 mL) was hydrogened with Pd/C (10 mg) under 1 atm. of H$_2$ pressure at RT overnight. LCMS indicated that starting material disappeared, the mixture filtered and concentrated in vacuo. The residue was purified by Prep-HPLC to give the title compound (19.2 mg) as a yellow residue. LRMS m/z (M+H) 432.1 found, 432.1 required.

Example 38

(2-(2H-1,2,3-triazol-2-yl)phenyl)((2R,5R)-5-((3-(difluoromethyl)imidazo[1,2-a]pyrazin-8-yl)oxy)-2-methylpiperidin-1-yl)methanone

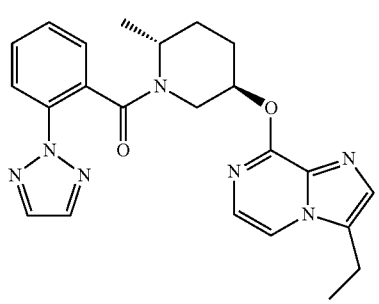 [SMILES: CCc1cnc2c(O[C@@H]3CC[C@@H](C)N(C(=O)c4ccccc4-n4nccn4)C3)nccn12]

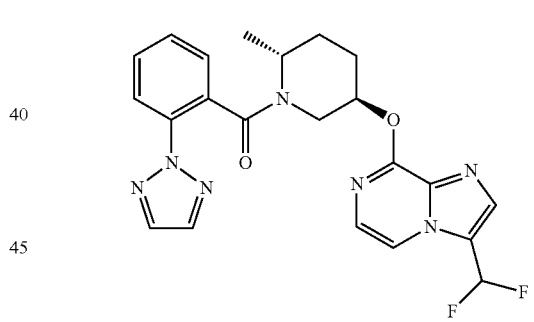

Scheme for the Preparation of Example 37

Scheme for the Preparation of Example 38

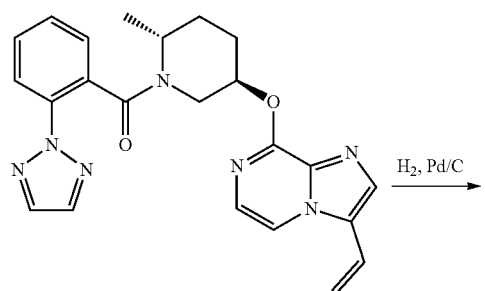

Example 36

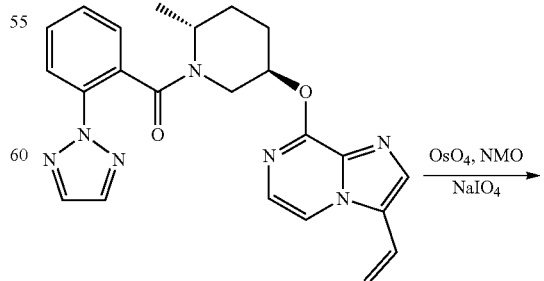

Example 36

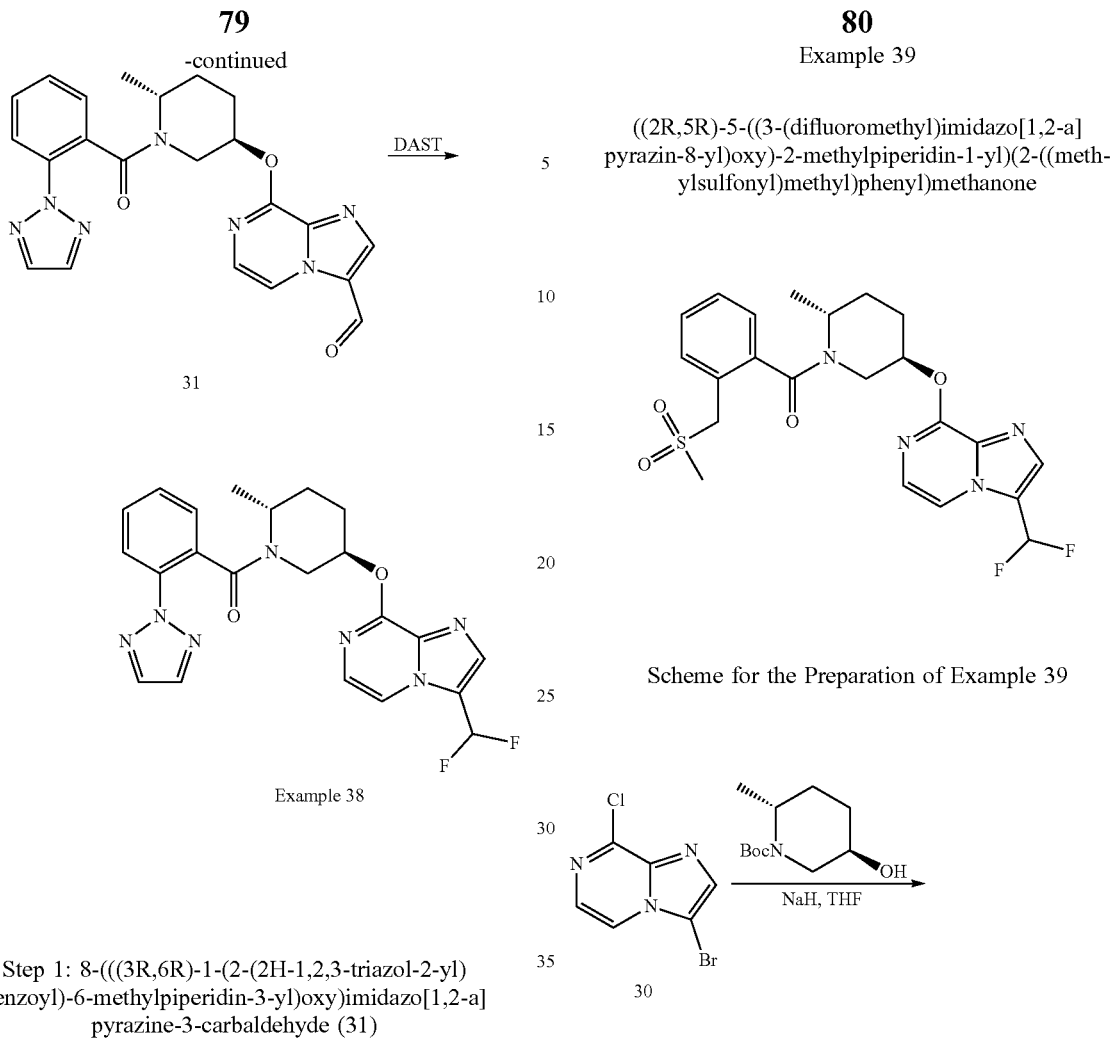

Example 38

Step 1: 8-(((3R,6R)-1-(2-(2H-1,2,3-triazol-2-yl)benzoyl)-6-methylpiperidin-3-yl)oxy)imidazo[1,2-a]pyrazine-3-carbaldehyde (31)

To a mixture of Example 36 (50 mg, 0.12 mmol), NMO (14 mg, 0.12 mmol) in THF/$H_2O$ (10/10 mL) was added $OsO_4$ (30 mg, 0.12 mmol) in 0.5 mL of water. The mixture was stirred at RT overnight. Then $NaIO_4$ (50 mg, 0.24 mmol) was added and the mixture was stirred for another 5 hours. LCMS indicated that starting material disappeared, the mixture was filtered, and the filtrate was extracted with EtOAc (10 mL×3). The combined organic layer was washed with water (10 mL) and brine (10 mL), dried over anhydrous sodium sulfate, filtered and concentrated in vacuo to give the title compound (40 mg) as yellow oil. LRMS m/z (M+H) 432.1 found, 432.1 required.

Step 2: (2-(2H-1,2,3-triazol-2-yl)phenyl)((2R,5R)-5-((3-(difluoromethyl)imidazo[1,2-a]pyrazin-8-yl)oxy)-2-methylpiperidin-1-yl)methanone (Example 38)

To a solution of the product from step 1 (50 mg, 0.12 mmol) in DCM (5 mL) was added DAST (56 mg, 0.34 mmol) at 0° C. The mixture was stirred at RT for 3 hours. LCMS indicated that starting material disappeared. The mixture was quenched with aqueous $NaHCO_3$ solution (0.5 mL), filtered and concentrated in vacuo. The residue was purified by Prep-HPLC to give the title compound (26.1 mg) as yellow oil. LRMS m/z (M+H) 454.1 found, 454.1 required.

Example 39

((2R,5R)-5-((3-(difluoromethyl)imidazo[1,2-a]pyrazin-8-yl)oxy)-2-methylpiperidin-1-yl)(2-((methylsulfonyl)methyl)phenyl)methanone Scheme for the Preparation of Example 39

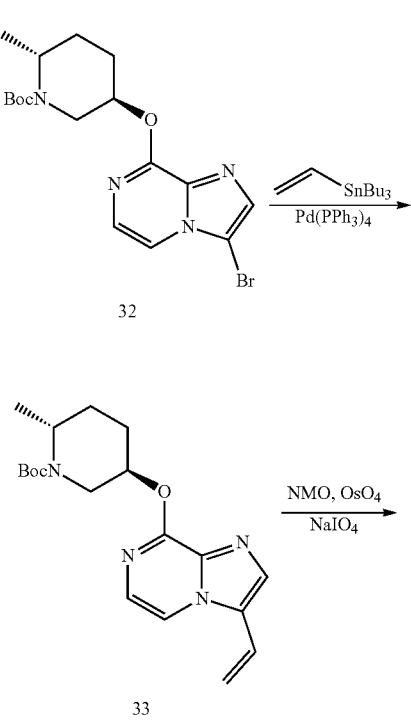

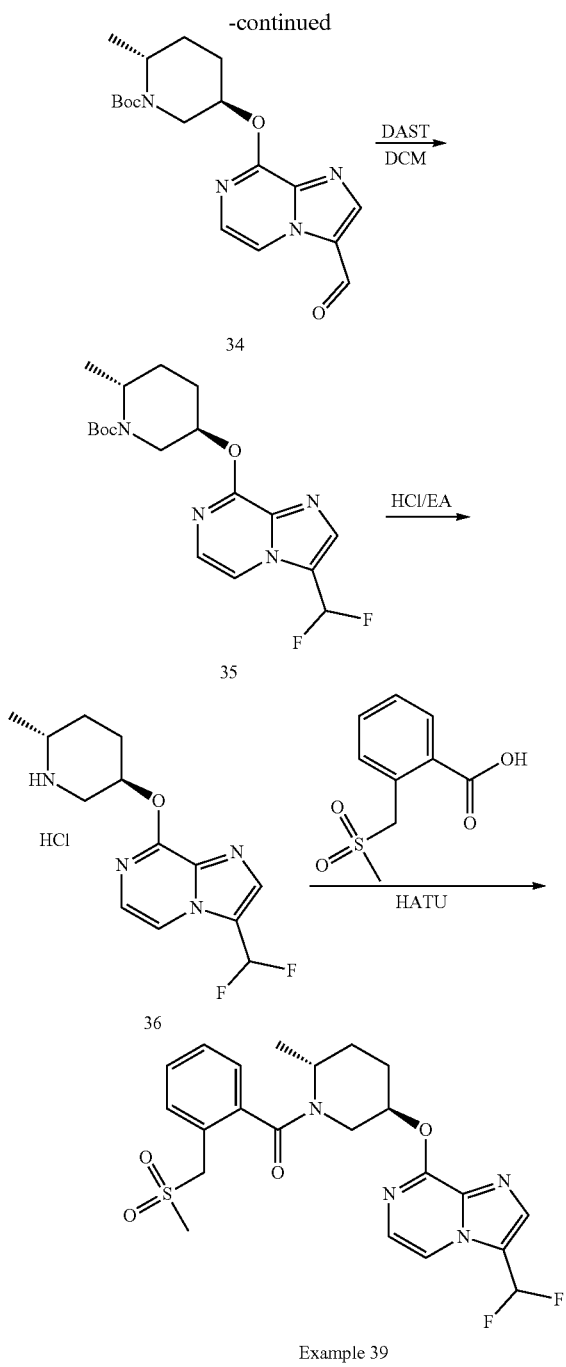

Example 39

Step 1: (2R,5R)-tert-butyl 5-((3-bromoimidazo[1,2-a]pyrazin-8-yl)oxy)-2-methylpiperidine-1-carboxylate (32)

To a solution of (2R,5R)-tert-butyl 5-hydroxy-2-methylpiperidine-1-carboxylate (500 mg, 2.3 mmol) in THF (10 mL) was added NaH (120 mg, 3.0 mmol, 60 wt % in oil) at RT. The mixture was refluxed for 1 hour, then compound 30 (example 33, step 1) (540 mg, 2.3 mmol) was added. The resulting mixture was refluxed for an additional 30 minutes. After LCMS indicated that starting material disappeared, the mixture was cooling to RT, poured into water (10 mL), extracted with EtOAc (10 mL×3). The combined organic layer was washed with water (10 mL) and brine (10 mL), dried over anhydrous sodium sulfate, filtered and concentrated in vacuo. The residue was purified by chromatography on silica (10% EtOAc in petroleum ether) to give the title compound (700 mg) as a light yellow oil. LRMS m/z (M+H) 411.1, 413.1 found, 411.1, 413.1 required.

Step 2: (2R,5R)-tert-butyl 2-methyl-5-((3-vinylimidazo[1,2-a]pyrazin-8-yl)oxy)piperidine-1-carboxylate (33)

To a mixture of the product from step 1 (500 mg, 1.22 mmol) and Pd(PPh$_3$)$_4$ (70 mg, 0.06 mmol) in toluene (5 mL) was added tributyl(vinyl)stannane (462 mg, 1.45 mmol) at RT. The mixture was refluxed for 2 hour. TLC (50% EtOAc in petroleum ether) indicated that starting material disappeared. The mixture was cooling to RT, filtered through celite pad. The filtrate was concentrated in vacuo. The residue was purified by chromatography on silica (5% EtOAc in petroleum ether) to give the title compound (330 mg) as an orange oil. LRMS m/z (M+H) 359.1 found, 359.1 required.

Step 3: (2R,5R)-tert-butyl 5-((3-formylimidazo[1,2-a]pyrazin-8-yl)oxy)-2-methylpiperidine-1-carboxylate (34)

To a solution of the product from step 2 (330 mg, 0.92 mmol) and NMO (161 mg, 1.4 mmol) in THF/H$_2$O (5 mL) was added OsO$_4$ (25 mg, 0.09 mmol in 0.5 mL of water) at RT. The mixture was stirred at RT overnight. Then NaIO$_4$ (385 mg, 1.8 mmol) was added, the mixture was stirred for another 2 hours, TLC (petroleum ether:EtOAc=1:1) indicated that starting material disappeared. The mixture was diluted with water (10 mL), extracted with EtOAc (20 mL×3). The combined organic layer was washed with water (20 mL) and brine (20 mL), dried over anhydrous sodium sulfate, filtered and concentrated in vacuo. The residue was purified by chromatography on silica (5% EtOAc in petroleum ether) to give the title compound (280 mg) as yellow oil. LRMS m/z (M+H) 361.1 found, 361.1 required.

Step 4: (2R,5R)-tert-butyl 5-((3-(difluoromethyl)imidazo[1,2-a]pyrazin-8-yl)oxy)-2-methylpiperidine-1-carboxylate (35)

To a solution of the product from step 3 (280 mg, 0.78 mmol) in DCM (3 mL) was added DAST (0.7 mL) at RT. The mixture was heated to 50° C. overnight. After cooling to RT, the mixture was quenched with sat. aqueous NaHCO$_3$ solution (10 mL), diluted with water (20 mL) and extracted with DCM (20 mL×3). The combined organic layer was washed with water (20 mL) and brine (20 mL), dried over anhydrous sodium sulfate, filtered and concentrated in vacuo. The residue was purified by chromatography on silica (5% EtOAc in petroleum ether) to give the title compound (250 mg) as a white solid. LRMS m/z (M+H) 383.1 found, 383.1 required.

Step 5: 3-(difluoromethyl)-8-(((3R,6R)-6-methylpiperidin-3-yl)oxy)imidazo[1,2-a]pyrazine hydrochloride (36)

A solution of the product from step 4 (250 mg, 0.65 mmol) in HCl/EtOAc (5 mL, 2 N) was stirred at RT for 50 minutes. TLC (petroleum ether:EtOAc=1:1) indicated that starting material disappeared; the mixture was concentrated

83 in vacuo to give the title compound (35 mg) as a white solid. LRMS m/z (M+H) 283.1 found, 283.1 required.

Step 6: ((2R,5R)-5-((3-(difluoromethyl)imidazo[1,2-a]pyrazin-8-yl)oxy)-2-methylpiperidin-1-yl)(2-((methylsulfonyl)methyl)phenyl)methanone (Example 39)

To a solution of the product from step 5 (20 mg, 0.06 mmol) and 2-((methylsulfonyl)methyl)benzoic acid (12.8 mg, 0.06 mmol) and TEA (0.5 mL) in DMF (3 mL) was added HATU (50 mg, 0.13 mmol) at RT. The mixture was stirred at RT for 16 hours. LCMS indicated that starting material disappeared; the mixture was purified by Prep-HPLC to give the title compound (23.7 mg) as a white solid. LRMS m/z (M+H) 479.1 found, 479.1 required.

The following compounds were prepared according to the general procedure provided in Example 39 and the procedures herein. The starting materials are either commercially available or may be prepared from commercially available reagents using conventional reactions well known in the art.

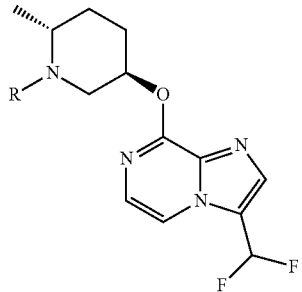

TABLE 7

| Example | R | Chemical Name | LRMS or HRMS (M + H⁺) |
|---|---|---|---|
| 40 | (thiophene with 2H-1,2,3-triazol-2-yl substituent) | (2-(2H-1,2,3-triazol-2-yl)thiophen-3-yl)((2R,5R)-5-((3-(difluoromethyl)imidazo[1,2-α]pyrazin-8-yl)oxy)-2-methylpiperidin-1-yl)methanone | Calc'd 460.1, found 460.1 |
| 41 | (thiophene with 2H-1,2,3-triazol-2-yl substituent) | (4-(2H-1,2,3-triazol-2-yl)thiophen-3-yl)((2R,5R)-5-((3-(difluoromethyl)imidazo[1,2-α]pyrazin-8-yl)oxy)-2-methylpiperidin-1-yl)methanone | Calc'd 460.1, found 460.1 |
| 42 | (phenyl with 1-cyanocyclopropyl substituent) | 1-(2-((2R,5R)-5-((3-(difluoromethyl)imidazo[1,2-α]pyrazin-8-yl)oxy)-2-methylpiperidine-1-carbonyl)phenyl)cyclopropanecarbonitrile | Calc'd 452.2, found 452.2 |
| 43 | (4-fluorophenyl with 2H-1,2,3-triazol-2-yl substituent) | ((2R,5R)-5-((3-(difluoromethyl)imidazo[1,2-α]pyrazin-8-yl)oxy)-2-methylpiperidin-1-yl)(4-fluoro-2-(2H-1,2,3-triazol-2-yl)phenyl)methanone | Calc'd 472.2, found 472.2 |
| 44 | (phenyl with 2H-tetrazol-2-yl substituent) | (2-(2H-tetrazol-2-yl)phenyl)((2R,5R)-5-((3-(difluoromethyl)imidazo[1,2-α]pyrazin-8-yl)oxy)-2-methylpiperidin-1-yl)methanone | Calc'd 455.2, found 455.2 |

TABLE 7-continued

| Example | R | Chemical Name | LRMS or HRMS (M + H⁺) |
|---|---|---|---|
| 45 | (2-methoxymethyl-phenyl ketone) | ((2R,5R)-5-((3-(difluoromethyl)imidazo[1,2-α]pyrazin-8-yl)oxy)-2-methylpiperidin-1-yl)(2-(methoxymethyl)phenyl)methanone | Calc'd 431.1, found 431.1 |
| 46 | (3-(1H-pyrazol-1-yl)pyrazin-2-yl ketone) | (3-(1H-pyrazol-1-yl)pyrazin-2-yl)((2R,5R)-5-((3-(difluoromethyl)imidazo[1,2-α]pyrazin-8-yl)oxy)-2-methylpiperidin-1-yl)methanone | Calc'd 455.2, found 455.2 |
| 47 | (3-(pyridin-2-yl)pyrazin-2-yl ketone) | ((2R,5R)-5-((3-(difluoromethyl)imidazo[1,2-α]pyrazin-8-yl)oxy)-2-methylpiperidin-1-yl)(3-(pyridin-2-yl)pyrazin-2-yl)methanone | Calc'd 466.2, found 466.2 |
| 48 | (methyl pyrazine-2-carboxylate ketone) | methyl 2-((2R,5R)-5-((3-(difluoromethyl)imidazo[1,2-α]pyrazin-8-yl)oxy)-2-methylpiperidine-1-carbonyl)benzoate | Calc'd 445.2, found 445.2 |
| 49 | (3-phenylpyridin-2-yl ketone) | ((2R,5R)-5-((3-(difluoromethyl)imidazo[1,2-α]pyrazin-8-yl)oxy)-2-methylpiperidin-1-yl)(3-phenylpyridin-2-yl)methanone | Calc'd 464.1, found 464.1 |
| 50 | (2-(2,2,2-trifluoroethoxy)pyridin-3-yl ketone) | ((2R,5R)-5-((3-(difluoromethyl)imidazo[1,2-α]pyrazin-8-yl)oxy)-2-methylpiperidin-1-yl)(2-(2,2,2-trifluoroethoxy)pyridin-3-yl)methanone | Calc'd 486.1, found 486.1 |
| 51 | (2-(2,2-difluoroethoxy)pyridin-3-yl ketone) | (2-(2,2-difluoroethoxy)pyridin-3-yl)((2R,5R)-5-((3-(difluoromethyl)imidazo[1,2-α]pyrazin-8-yl)oxy)-2-methylpiperidin-1-yl)methanone | Calc'd 468.1, found 468.1 |

TABLE 7-continued

| Example | R | Chemical Name | LRMS or HRMS (M + H+) |
|---|---|---|---|
| 52 | 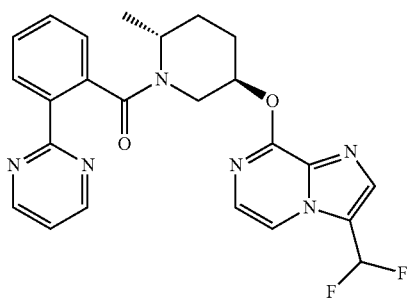 | (2-(1H-pyrazol-1-yl)pyridin-3-yl)((2R,5R)-5-((3-(difluoromethyl)imidazo[1,2-α]pyrazin-8-yl)oxy)-2-methylpiperidin-1-yl)methanone | Calc'd 454.1, found 454.1 |
| 53 | 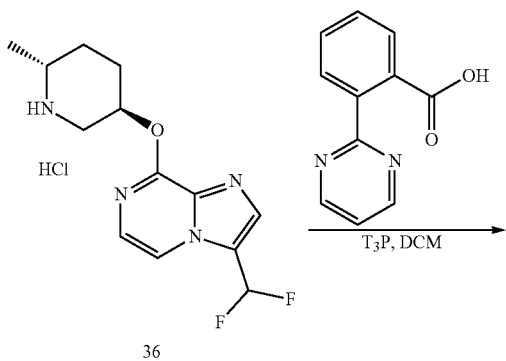 | ((2R,5R)-5-((3-(difluoromethyl)imidazo[1,2-α]pyrazin-8-yl)oxy)-2-methylpiperidin-1-yl)(2-(pyrazin-2-yl)phenyl)methanone | Calc'd 465.1, found 465.1 |

Example 54

((2R,5R)-5-((3-(difluoromethyl)imidazo[1,2-a]pyrazin-8-yl)oxy)-2-methylpiperidin-1-yl)(2-(pyrimidin-2-yl)phenyl)methanone Scheme for the Preparation of Example 54

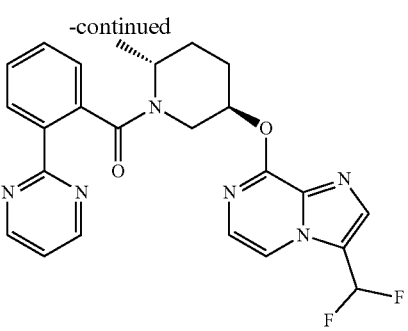

Example 54

Step 1: 42R,5R)-5-((3-(difluoromethyl)imidazo[1,2-a]pyrazin-8-yl)oxy)-2-methylpiperidin-1-yl)(2-(pyrimidin-2-yl)phenyl)methanone (Example 54)

To a solution of compound 36 (example 39, step 1) (20 mg, 0.06 mmol) and 2-(pyrimidin-2-yl)benzoic acid (12 mg, 0.06 mmol) and TEA (0.5 mL) in DCM (5 mL) was added $T_3P$ (50 mg, 0.12 mmol) at RT. The mixture was heated to 50° C. overnight. LCMS indicated that starting material disappeared, the mixture was concentrated in vacuo, and the residue was purified by Prep-HPLC to give the title compound (22.3 mg) as a white solid. LRMS m/z (M+H) 465.1 found, 465.1 required.

The following compounds were prepared according to the general procedure provided in Example 54 and the procedures herein. The starting materials are either commercially available or may be prepared from commercially available reagents using conventional reactions well known in the art.

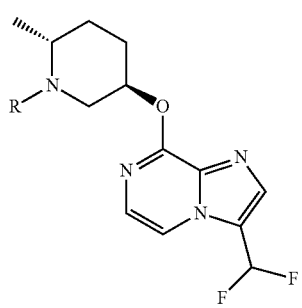

TABLE 8

| Example | R | Chemical Name | LRMS or HRMS (M + H⁺) |
|---|---|---|---|
| 55 | (thiophene with pyrimidin-2-yl and C(=O) linker) | ((2R,5R)-5-((3-(difluoromethyl)imidazo[1,2-α]pyrazin-8-yl)oxy)-2-methylpiperidin-1-yl)(4-(pyrimidin-2-yl)thiophen-3-yl)methanone | Calc'd 471.1, found 471.1 |
| 56 | (thiophene with pyrimidin-2-yl and C(=O) linker) | ((2R,5R)-5-((3-(difluoromethyl)imidazo[1,2-α]pyrazin-8-yl)oxy)-2-methylpiperidin-1-yl)(2-(pyrimidin-2-yl)thiophen-3-yl)methanone | Calc'd 471.1, found 471.1 |

Example 57

(2-(2H-1,2,3-triazol-2-yl)phenyl)((2R,5R)-2-methyl-5-(trifluoromethyl)imidazo[1,2-a]pyrazin-8-yl)oxy)piperidin-1-yl)methanone

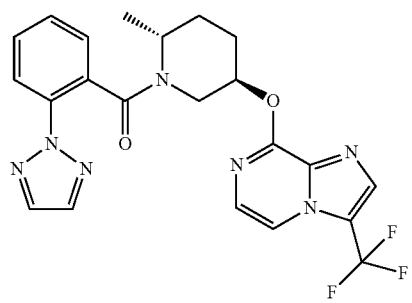 [SMILES: C[C@@H]1CC[C@@H](Oc2nccn3c(C(F)(F)F)cnc23)CN1C(=O)c1ccccc1-n1nccn1]

Scheme for the Preparation of Example 57

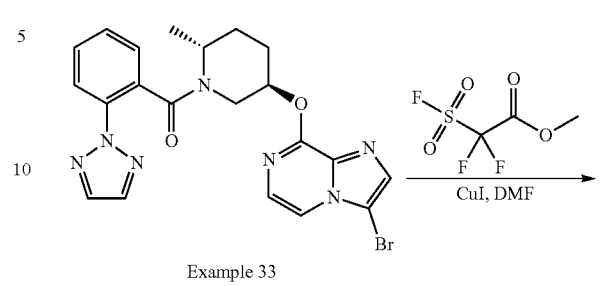

Step 1: (2-(2H-1,2,3-triazol-2-yl)phenyl)((2R,5R)-2-methyl-5-((3-(trifluoromethyl)imidazo[1,2-a]pyrazin-8-yl)oxy)piperidin-1-yl)methanone (Example 57)

A solution of Example 33 (40 mg, 0.082 mmol), methyl 2,2-difluoro-2-(fluorosulfonyl)acetate (23 mg, 0.12 mmol), and CuI (5 mg, 0.026 mmol) in DMF (3 mL) was treated with microwave at 100° C. for 30 minutes. LCMS indicated that starting material disappeared, the mixture was filtered, and the filtrate was purified by Prep-HPLC to give the title compound (20 mg) as a yellow solid. LRMS m/z (M+H) 472.1 found, 472.1 required.

Example 58

(2-(2H-1,2,3-triazol-2-yl)thiophen-3-yl)((2R,5R)-2-methyl-5-((3-(trifluoromethyl)imidazo[1,2-a]pyrazin-8-yl)oxy)piperidin-1-yl)methanone

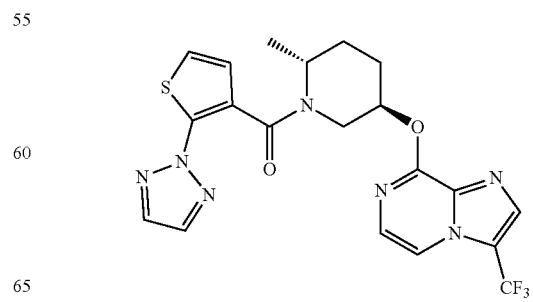

Scheme for the Preparation of Example 58

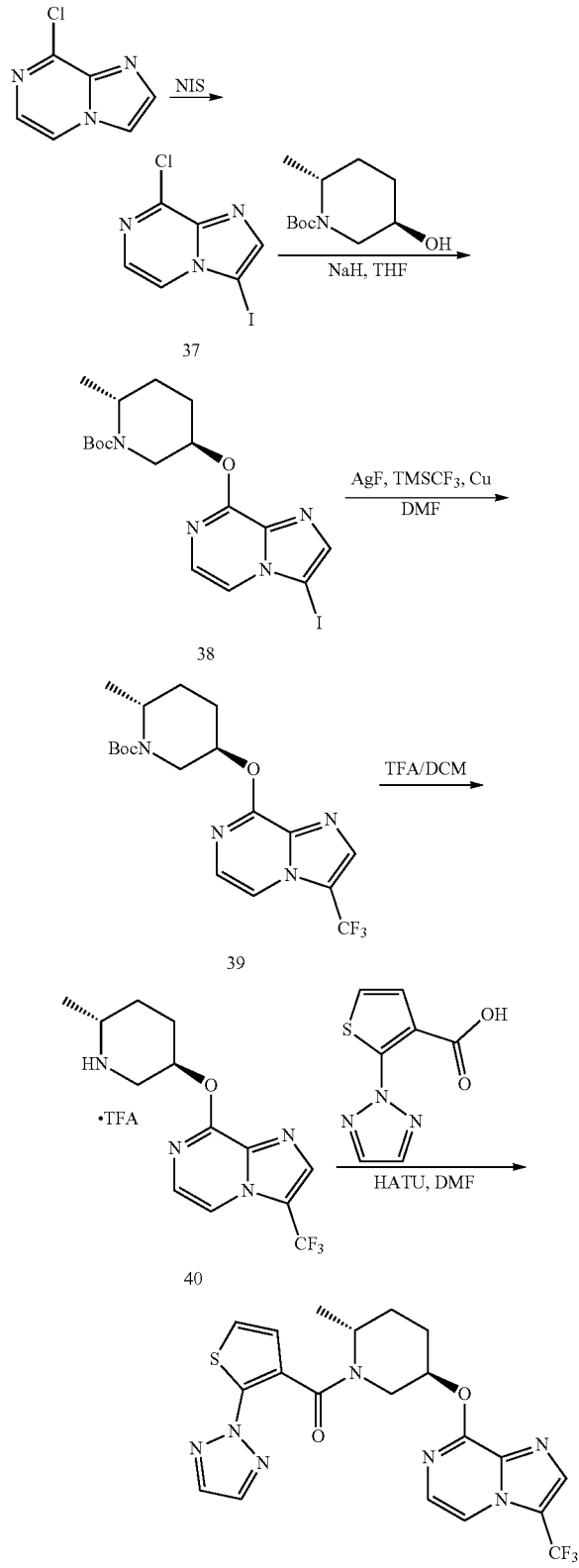

Example 58

Step 1: 8-chloro-3-iodoimidazo[1,2-a]pyrazine (37)

To a solution of 8-chloroimidazo[1,2-a]pyrazine (200 mg, 1.3 mmol) in MeCN/DCE (3 mL/1.5 mL) was added NIS (293 mg, 1.3 mmol) at RT. The mixture was refluxed overnight. TLC (50% EtOAc in petroleum ether) indicated that starting material disappeared, the mixture was poured into water (10 mL), extracted with EtOAc (10 mL×3). The combined organic layer was washed with water (10 mL) and brine (10 mL), dried over anhydrous sodium sulfate, filtered and concentrated in vacuo to give the title compound (200 mg) as a brown solid. LRMS m/z (M+H) 279.1, 281.1 found, 279.1, 281.1 required.

Step 2: (2R,5R)-tert-butyl 5-((3-iodoimidazo[1,2-a]pyrazin-8-yl)oxy)-2-methylpiperidine-1-carboxylate (38)

To a solution of (2R,5R)-tert-butyl 5-hydroxy-2-methylpiperidine-1-carboxylate (400 mg, 1.86 mmol) in THF (10 mL) was added NaH (84 mg, 2.1 mmol, 60 wt % in oil) at RT. The mixture was refluxed for 1 hour, then the product from step 1 (502 mg, 1.8 mmol) was added, the mixture was refluxed for additional 30 minutes. LCMS indicated that starting material disappeared. The mixture was cooling to RT, poured into water (20 mL), extracted with EtOAc (20 mL×3). The combined organic layer was washed with water (20 mL) and brine (20 mL), dried over anhydrous sodium sulfate, filtered and concentrated in vacuo. The residue was purified by chromatography on silica (5% EtOAc in petroleum ether) to give the title compound (450 mg) as yellow oily residue. LRMS m/z (M+H) 459.2 found, 459.2 required.

Step 3: (2R,5R)-tert-butyl 2-methyl-5-((3-(trifluoromethyl)imidazo[1,2-a]pyrazin-8-yl)oxy)piperidine-1-carboxylate (39)

To a degassed mixture of AgF (73 mg, 0.58 mmol) in DMF (2 mL) was added TMSCF$_3$ (91 mg, 0.64 mmol) at RT under N$_2$ protection. The mixture was stirred at this temperature for 20 minutes. Then Cu (50 mg, 0.8 mmol) was added, the resulting mixture was stirred for 4 hours, and the product from step 2 (240 mg, 0.52 mmol) was added. The mixture was heated to 100° C. overnight. TLC (50% EtOAc in petroleum ether) indicated that starting material disappeared. The mixture was filtered, the filtrate was poured into water (10 mL), extracted with EtOAc (10 mL×3). The combined organic layer was washed with water (10 mL) and brine (10 mL), dried over anhydrous sodium sulfate, filtered and concentrated in vacuo. The residue was purified by prep.TLC (50% EtOAc in petroleum ether) to give the title compound (100 mg) as yellow oily residue. LRMS m/z (M+H) 401.1 found, 401.1 required.

Step 4: 8-(((3R,6R)-6-methylpiperidin-3-yl)oxy)-3-(trifluoromethyl)imidazo[1,2-a]pyrazine TFA Salt (40)

To a solution of the product from step 3 (100 mg, 0.25 mmol) in DCM (2 mL) was added TFA (0.5 mL) at RT. The mixture was stirred for 20 minutes. LCMS indicated that starting material disappeared. The mixture was concentrated in vacuo to give the title compound (75 mg) as yellow oil. LRMS m/z (M+H) 301.1 found, 301.1 required.

Step 5: (2-(2H-1,2,3-triazol-2-yl)thiophen-3-yl)((2R,5R)-2-methyl-5-((3-(trifluoromethyl)imidazo[1,2-a]pyrazin-8-yl)oxy)piperidin-1-yl)methanone (Example 58)

To a solution of the product from step 4 (37 mg, 0.093 mmol), 2-(2H-1,2,3-triazol-2-yl)thiophene-3-carboxylic acid (23.4 mg, 0.12 mmol) and TEA (0.5 mL) in DMF (3 mL) was added HATU (70 mg, 0.18 mmol) at RT. The mixture was stirred at RT for 16 hours. LCMS indicated that starting material disappeared and the mixture was filtered. The filtrate was purified by Prep-HPLC to give the title compound (24 mg) as a brown solid. LRMS m/z (M+H) 478.1 found, 478.1 required.

The following compounds were prepared according to the general procedure provided in Example 58 and the procedures herein. The starting materials are either commercially available or may be prepared from commercially available reagents using conventional reactions well known in the art.

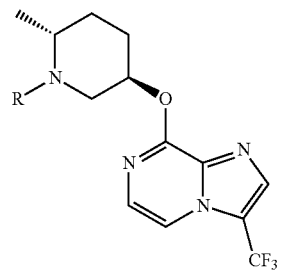

TABLE 9

| Example | R | Chemical Name | LRMS or HRMS (M + H+) |
|---|---|---|---|
| 59 | (2-cyanocyclopropyl)phenyl-C(=O)- group | 1-(2-((2R,5R)-2-methyl-5-((3-(trifluoromethyl)imidazo[1,2-α]pyrazin-8-yl)oxy)piperidine-1-carbonyl)phenyl)cyclopropanecarbonitrile | Calc'd 470.1, found 470.1 |
| 60 | (2-(2H-tetrazol-2-yl)phenyl)-C(=O)- group | (2-(2H-tetrazol-2-yl)phenyl)((2R,5R)-2-methyl-5-((3-(trifluoromethyl)imidazo[1,2-α]pyrazin-8-yl)oxy)piperidin-1-yl)methanone | Calc'd 473.1, found 473.1 |
| 61 | (2-((methylsulfonyl)methyl)phenyl)-C(=O)- group | ((2R,5R)-2-methyl-5-((3-(trifluoromethyl)imidazo[1,2-α]pyrazin-8-yl)oxy)piperidin-1-yl)(2-((methylsulfonyl)methyl)phenyl)methanone | Calc'd 497.1, found 497.1 |
| 62 | (3-phenylpyridin-2-yl)-C(=O)- group | ((2R,5R)-2-methyl-5-((3-(trifluoromethyl)imidazo[1,2-α]pyrazin-8-yl)oxy)piperidin-1-yl)(3-phenylpyridin-2-yl)methanone | Calc'd 482.1, found 482.1 |
| 63 | (2-(2,2,2-trifluoroethoxy)pyridin-3-yl)-C(=O)- group | ((2R,5R)-2-methyl-5-((3-(trifluoromethyl)imidazo[1,2-α]pyrazin-8-yl)oxy)piperidin-1-yl)(2-(2,2,2-trifluoroethoxy)pyridin-3-yl)methanone | Calc'd 504.1, found 504.1 |

TABLE 9-continued

| Example | R | Chemical Name | LRMS or HRMS (M + H+) |
|---|---|---|---|
| 64 | 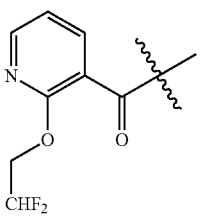 [SMILES: *C(=O)c1cccnc1OCC(F)F] | (2-(2,2-difluoroethoxy)pyridin-3-yl)((2R,5R)-2-methyl-5-((3-(trifluoromethyl)imidazo[1,2-α]pyrazin-8-yl)oxy)piperidin-1-yl)methanone | Calc'd 486.1, found 486.1 |
| 65 | 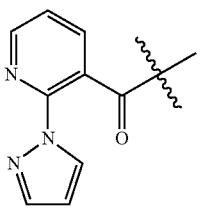 [SMILES: *C(=O)c1cccnc1-n1cccn1] | (2-(1H-pyrazol-1-yl)pyridin-3-yl)((2R,5R)-2-methyl-5-((3-(trifluoromethyl)imidazo[1,2-α]pyrazin-8-yl)oxy)piperidin-1-yl)methanone | Calc'd 472.1, found 472.1 |

Example 66

((2R,5R)-2-methyl-5-((3-(trifluoromethyl)imidazo[1,2-a]pyrazin-8-yl)oxy)piperidin-1-yl)(2-(pyrimidin-2-yl)phenyl)methanone

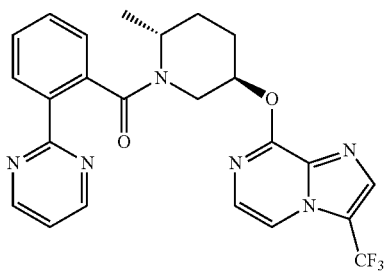 [SMILES: C[C@@H]1CC[C@@H](Oc2nccn3c(C(F)(F)F)cnc23)CN1C(=O)c1ccccc1-c1ncccn1]

Scheme for the Preparation of Example 66

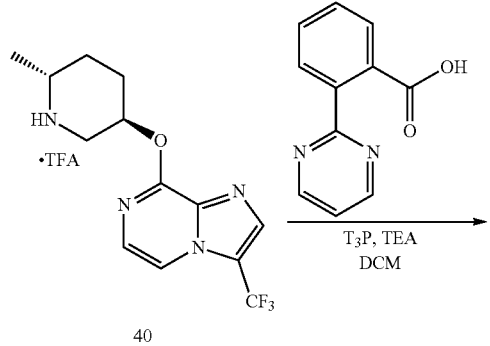

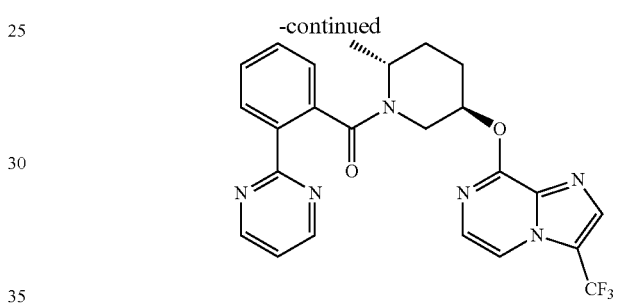

Example 66

Step 1: (2-(2H-1,2,3-triazol-2-yl)phenyl)((2R,5R)-5-(imidazo[1,2-a]pyrazin-8-yloxy)-2-methylpiperidin-1-yl)methanone (Example 66)

To a solution of compound 40 (example 58, step 4) (37 mg, 0.093 mmol), 2-(pyrimidin-2-yl)benzoic acid (30 mg, 0.15 mmol) and TEA (0.5 mL) in DCM (3 mL) was added T₃P (0.5 mL) at RT. The mixture was refluxed for 30 hours. LCMS indicated that starting material disappeared; the mixture was quenched with water (5 mL) and concentrated in vacuo. The residue was purified by Prep-HPLC to give the title compound (3.54 mg) as a brown solid.
LRMS m/z (M+H) 483.1 found, 483.1 required.

Example 67

(2-(2H-1,2,3-triazol-2-yl)phenyl)((2R,5R)-5-((3-(2,2-difluoro-1-hydroxyethyl)imidazo[1,2-a]pyrazin-8-yl)oxy)-2-methylpiperidin-1-yl)methanone

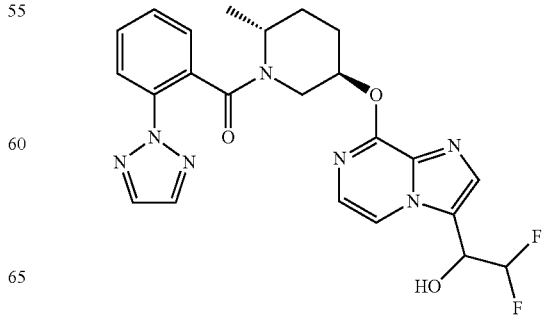

Scheme for the Preparation of Example 67

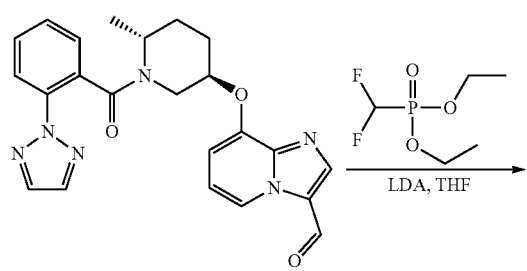

31

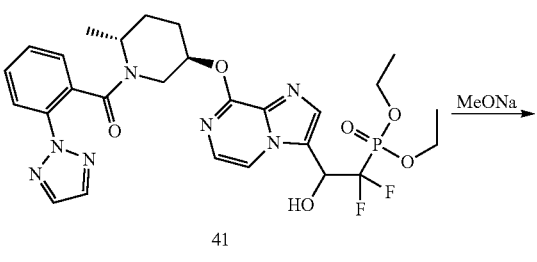

41

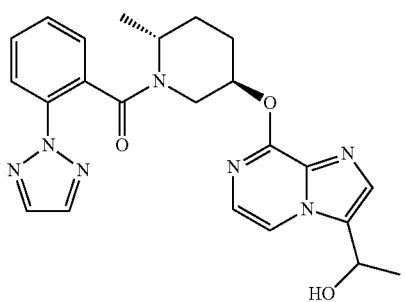 [SMILES: CC(O)c1cnc2c(O[C@@H]3CC[C@@H](C)N(C(=O)c4ccccc4-n4nccn4)C3)nccn12]

Example 67

Step 1: (2-(2H-1,2,3-triazol-2-yl)phenyl)((2R,5R)-5-((3-(2,2-difluoro-1-hydroxyethyl)imidazo[1,2-a]pyrazin-8-yl)oxy)-2-methylpiperidin-1-yl)methanone (Example 67)

To a mixture of diethyl (difluoromethyl)phosphonate (52 mg, 0.27 mmol) in THF (2 mL) was added LDA (0.15 mL, 0.30 mmol) at −78° C. dropwise. The mixture was stirred at −78° C. for 1 hour. Then compound 31 (example 38, step 1) (40 mg, 0.09 mmol) in THF (2 mL) was added dropwise. The mixture was stirred at −78° C. for 3 hours. The mixture was quenched with water (5 mL), extracted with EtOAc (5 mL×3). The combined organic layer was washed with water (5 mL) and brine (5 mL), dried over anhydrous sodium sulfate, filtered and concentrated in vacuo. The residue was dissolved in methanol (5 mL), and NaOMe (16 mg, 0.3 mmol) was added. The mixture was refluxed overnight, LCMS indicated the reaction was finished; the mixture was purified by Prep-HPLC to give the title compound (1.82 mg) as yellow oil. LRMS m/z (M+H) 484.1 found, 484.1 required.

Example 68

(2-(2H-1,2,3-triazol-2-yl)phenyl)((2R,5R)-5-((3-(1-hydroxyethyl)imidazo[1,2-a]pyrazin-8-yl)oxy)-2-methylpiperidin-1-yl)methanone

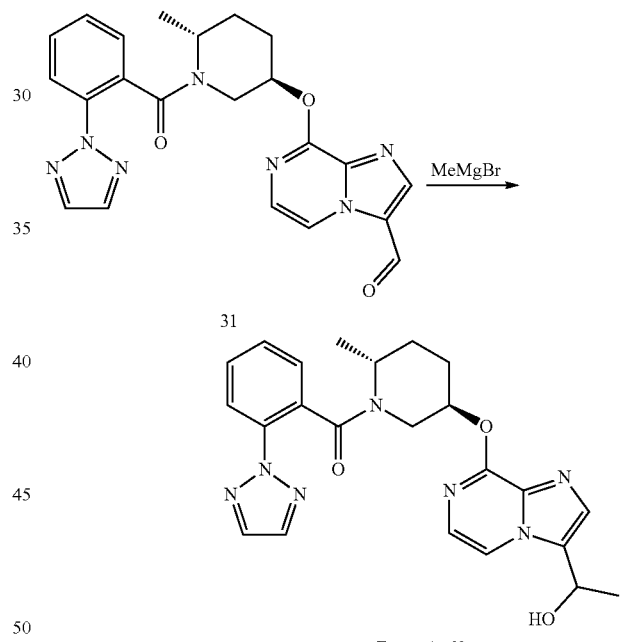

Scheme for the Preparation of Example 68

Step 1: (2-(2H-1,2,3-triazol-2-yl)phenyl)((2R,5R)-5-((3-(1-hydroxyethyl)imidazo[1,2-a]pyrazin-8-yl)oxy)-2-methylpiperidin-1-yl)methanone (Example 68)

To a solution of compound 31 (example 38, step 1) (70 mg, 0.16 mmol) in THF (5 mL) was added MeMgBr (0.16 mL, 0.48 mmol) at RT. The mixture was stirred at this temperature for 3 hours. The mixture was quenched with aqueous NH₄Cl solution (5 mL), extracted with EtOAc (10 mL×3). The combined organic layer was washed with water (10 mL) and brine (10 mL), dried over anhydrous sodium sulfate, filtered and concentrated in vacuo. The residue was purified by Prep-TLC (9% MeOH in DCM) to give the title compound (300 mg) as a yellow residue. LRMS m/z (M+H) 448.1 found, 448.1 required.

Example 69

(2-(2H-1,2,3-triazol-2-yl)phenyl)((2R,5R)-2-methyl-5-(pyrazolo[1,5-a]pyrazin-4-yloxy)piperidin-1-yl)methanone

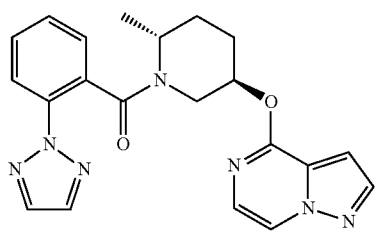 [SMILES: C[C@@H]1CC[C@@H](Oc2nccn3nccc23)CN1C(=O)c1ccccc1-n1nccn1]

Scheme for the Preparation of Example 69

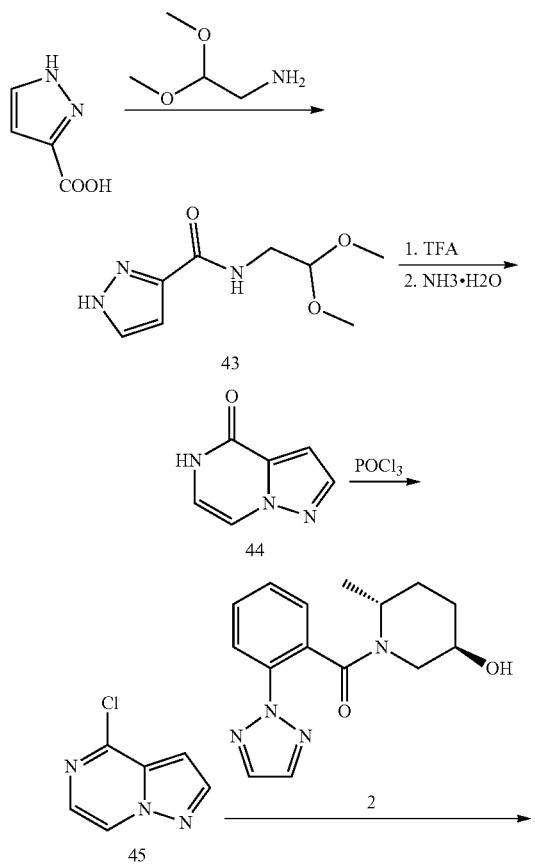

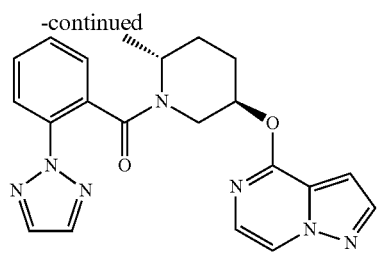

Example 69

Step 1:
N-(2,2-dimethoxyethyl)-1H-pyrazole-3-carboxamide (43)

To a solution of 1H-pyrazole-3-carboxylic acid (1.12 g, 10.0 mmol) in DMF (10 mL) was added HATU (5.93 g, 15.0 mmol), DIPEA (2.60 g, 20.0 mmol) and aminoacetaldehyde dimethyl acetal (1.05 g, 10.0 mmol). The mixture was stirred at RT overnight, diluted with water (20 mL) and extracted with DCM (20 mL×3). The combined organic layer was washed with brine, dried over magnesium sulfate, filtered, and concentrated in vacuo. The residue was purified by chromatography on silica (5% MeOH in DCM) to give the title compound (400 mg) as yellow oil. LRMS m/z (M+H) 200.1 found, 200.1 required.

Step 2: pyrazolo[1,5-a]pyrazin-4(5H)-one (44)

A mixture of the product from step 1 (300 mg, 1.51 mmol) in DCM (3 mL) and trifluoroacetic acid (3 mL) was stirred at RT for 16 hours, and then concentrated in vacuo. The residue was suspended in polyphosphoric acid (2 mL) and heated to 145° C. for 4.5 hours. The mixture was treated with ice water, and the pH was adjusted to 10 by addition of concentrated ammonium hydroxide solution. The mixture was extracted with DCM (20 mL×3). The combined organic layer was washed with brine, dried over magnesium sulfate, filtered, and concentrated in vacuo. The residue was purified by Prep-TLC (50% EtOAc in petroleum ether) to give the title compound (150 mg) as brown oil. LRMS m/z (M+H) 136.1 found, 136.1 required.

Step 3: 4-chloropyrazolo[1,5-a]pyrazine (45)

To a mixture of the product from step 2 (150 mg, 1.1 mmol) in phosphorus oxychloride (5 mL) was added N,N-diethylaniline (493 mg, 3.3 mmol). The mixture was heated at 100° C. for 16 hours. After cooling to RT, the mixture was diluted with water (20 mL) and extracted with DCM (20 mL×3). The combined organic layer was washed with brine, dried over magnesium sulfate, filtered, and concentrated in vacuo. The residue was purified by Prep-TLC (50% EtOAc in petroleum ether) to give the title compound (60 mg) as a white solid. LRMS m/z (M+H) 154.1, 156.2 found, 154.1, 156.2 required.

Step 4: (2-(2H-1,2,3-triazol-2-yl)phenyl)((2R,5R)-2-methyl-5-(pyrazolo[1,5-a]pyrazin-4-yloxy)piperidin-1-yl)methanone (Example 69)

To a solution of compound 2 (example 1, step 2) (50 mg, 0.18 mmol) in THF (3 mL) was added NaH (21 mg, 0.53 mmol, 60 wt % in oil) at 0° C. The mixture was stirred at 0° C. for 0.5 h. then the product from step 3 (27 mg, 0.175 mmol) was added at 0° C. The mixture was stirred at RT for 2 hours and concentrated in vacuo and purified by Prep-HPLC to give the title compound (43.9 mg) as a white solid. LRMS m/z (M+H) 404.1 found, 404.1 required.

Example 70

(2-(2H-1,2,3-triazol-2-yl)thiophen-3-yl)((2R,5R)-2-methyl-5-(pyrazolo[1,5-a]pyrazin-4-yloxy)piperidin-1-yl)methanone

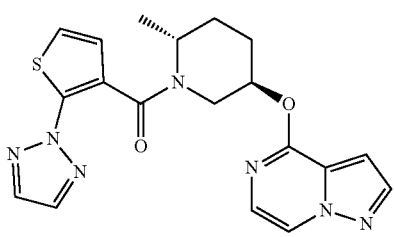 [SMILES: C[C@@H]1CC[C@@H](Oc2nccn3nccc23)CN1C(=O)c1ccsc1-n1nccn1]

Scheme for the Preparation of Example 70

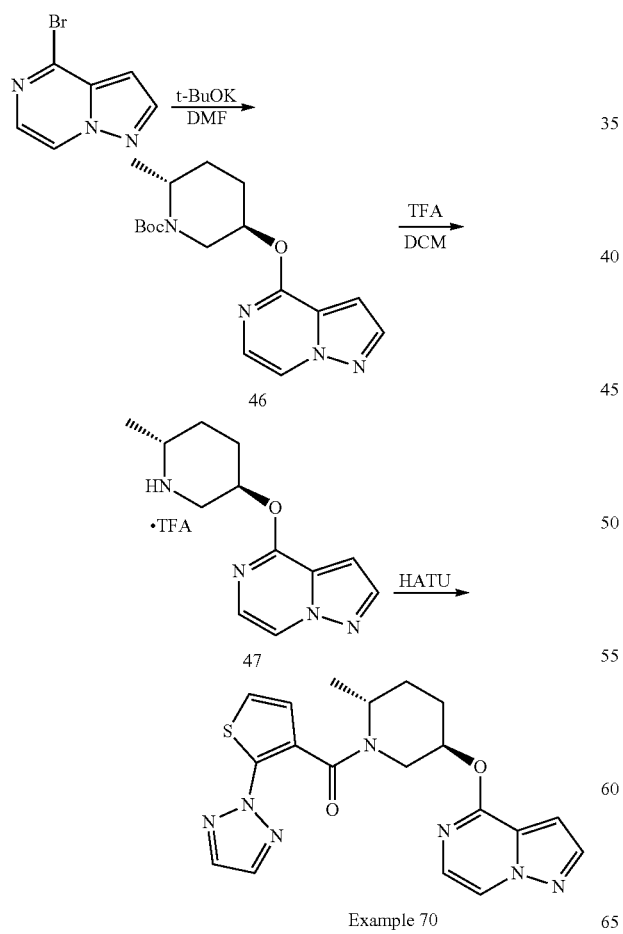

Step 1: (2R,5R)-tert-butyl 2-methyl-5-(pyrazolo[1,5-a]pyrazin-4-yloxy)piperidine-1-carboxylate (46)

To a solution of (2R,5R)-tert-butyl 5-hydroxy-2-methyl-piperidine-1-carboxylate (500 mg, 2.33 mmol) in DMF (2 mL) was added t-BuOK (713 mg, 6.89 mmol). After the mixture was stirred at RT for 20 min, 4-bromopyrazolo[1,5-a]pyrazine (450 mg, 2.28 mmol) was added. The resulting mixture was stirred at RT for 2 hours, poured into water (20 mL), extracted with EtOAc (20 mL×3). The combined organic layer was washed with brine, dried over magnesium sulfate, filtered, and concentrated in vacuo. The residue was purified by Prep-TLC (50% EtOAc in petroleum ether) to give the title compound (450 mg) as a yellow solid. LRMS m/z (M+H) 333.2 found, 333.2 required.

Step 2: 4-(((3R,6R)-6-methylpiperidin-3-yl)oxy)pyrazolo[1,5-a]pyrazine TFA Salt (47)

To a solution of the product from step 1 (470 mg, 1.42 mmol) in DCM (10 mL) was added trifluoroacetic acid (2 mL) at 0° C. The resulting mixture was stirred for 2 hours and concentrated in vacuo to give the title compound (300 mg) as a white solid. LRMS m/z (M+H) 233.2 found, 233.2 required.

Step 3: (2-(2H-1,2,3-triazol-2-yl)thiophen-3-yl)((2R, 5R)-2-methyl-5-(pyrazolo[1,5-a]pyrazin-4-yloxy)piperidin-1-yl)methanone (Example 70)

A solution of the product from step 2 (30 mg, 0.091 mmol), 2-(2H-1,2,3-triazol-2-yl)thiophene-3-carboxylic acid (50 mg, 0.26 mmol) and HATU (150 mg, 0.79 mmol) in DMF/DIEA (4 mL/0.5 mL) was stirred at RT overnight. LCMS indicated that starting material disappeared; the mixture was purified by Prep-HPLC to give the title compound (42.1 mg) as a white solid. LRMS m/z (M+H) 410.1 found, 410.1 required.

The following compounds were prepared according to the general procedure provided in Example 70 and the procedures herein. The starting materials are either commercially available or may be prepared from commercially available reagents using conventional reactions well known in the art.

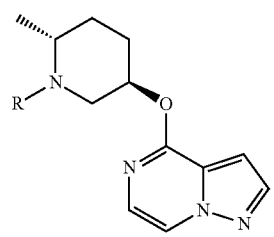

TABLE 10

| Example | R | Chemical Name | LRMS or HRMS (M + H+) |
|---|---|---|---|
| 71 | | (4-(2H-1,2,3-triazol-2-yl)thiophen-3-yl)((2R,5R)-2-methyl-5-(pyrazolo[1,5-α]pyrazin-4-yloxy)piperidin-1-yl)methanone | Calc'd 409.9, found 409.9 |
| 72 | | 1-(2-((2R,5R)-2-methyl-5-(pyrazolo[1,5-α]pyrazin-4-yloxy)piperidine-1-carbonyl)phenyl)cyclopropanecarbonitrile | Calc'd 402.0, found 402.0 |
| 73 | | (4-fluoro-2-(2H-1,2,3-triazol-2-yl)phenyl)((2R,5R)-2-methyl-5-(pyrazolo[1,5-α]pyrazin-4-yloxy)piperidin-1-yl)methanone | Calc'd 422.0, found 422.0 |
| 74 | | ((2R,5R)-2-methyl-5-(pyrazolo[1,5-α]pyrazin-4-yloxy)piperidin-1-yl)(4-(pyrimidin-2-yl)thiophen-3-yl)methanone | Calc'd 420.9, found 420.9 |
| 75 | | ((2R,5R)-2-methyl-5-(pyrazolo[1,5-α]pyrazin-4-yloxy)piperidin-1-yl)(2-(pyrimidin-2-yl)thiophen-3-yl)methanone | Calc'd 421.1, found 421.1 |
| 76 | | (2-(2H-tetrazol-2-yl)phenyl)((2R,5R)-2-methyl-5-(pyrazolo[1,5-α]pyrazin-4-yloxy)piperidin-1-yl)methanone | Calc'd 405.0, found 405.0 |
| 77 | | ((2R,5R)-5-(imidazo[1,2-α]pyrazin-8-yloxy)-2-methylpiperidin-1-yl)(2-((methylsulfonyl)methyl)phenyl)methanone | Calc'd 429.1, found 429.1 |

TABLE 10-continued

| Example | R | Chemical Name | LRMS or HRMS (M + H+) |
|---|---|---|---|
| 78 | 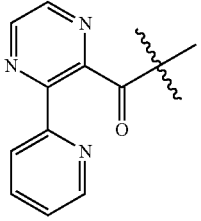 [SMILES: *C(=O)c1nccnc1-c1ccccn1] | ((2R,5R)-2-methyl-5-(pyrazolo[1,5-α]pyrazin-4-yloxy)piperidin-1-yl)(3-(pyridin-2-yl)pyrazin-2-yl)methanone | Calc'd 416.1, found 416.1 |
| 79 | 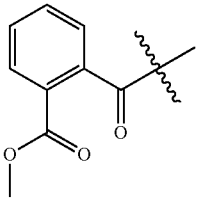 [SMILES: *C(=O)c1ccccc1C(=O)OC] | methyl 2-((2R,5R)-2-methyl-5-(pyrazolo[1,5-α]pyrazin-4-yloxy)piperidine-1-carbonyl)benzoate | Calc'd 395.1, found 395.1 |
| 80 | 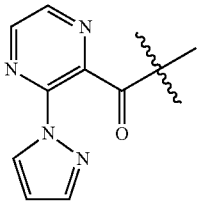 [SMILES: *C(=O)c1nccnc1-n1cccn1] | (3-(1H-pyrazol-1-yl)pyrazin-2-yl)((2R,5R)-2-methyl-5-(pyrazolo[1,5-α]pyrazin-4-yloxy)piperidin-1-yl)methanone | Calc'd 405.1, found 405.1 |
| 81 | 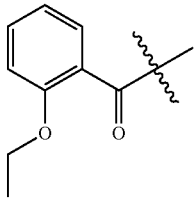 [SMILES: *C(=O)c1ccccc1OCC] | (2-ethoxyphenyl)((2R,5R)-2-methyl-5-(pyrazolo[1,5-α]pyrazin-4-yloxy)piperidin-1-yl)methanone | Calc'd 381.1, found 381.1 |
| 82 | 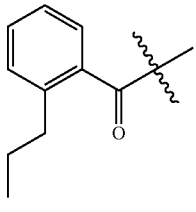 [SMILES: *C(=O)c1ccccc1CCC] | ((2R,5R)-2-methyl-5-(pyrazolo[1,5-α]pyrazin-4-yloxy)piperidin-1-yl)(2-propylphenyl)methanone | Calc'd 379.1, found 379.1 |
| 83 | 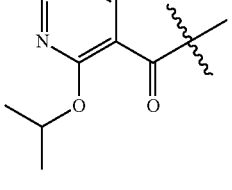 | (2-isopropoxypyridin-3-yl)((2R,5R)-2-methyl-5-(pyrazolo[1,5-α]pyrazin-4-yloxy)piperidin-1-yl)methanone | Calc'd 396.1, found 396.1 |
| 84 | 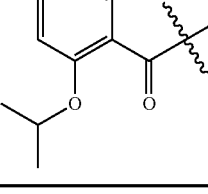 | (2-isopropoxyphenyl)((2R,5R)-2-methyl-5-(pyrazolo[1,5-α]pyrazin-4-yloxy)piperidin-1-yl)methanone | Calc'd 395.1, found 395.1 |

Example 85

((2R,5R)-2-methyl-5-(pyrazolo[1,5-a]pyrazin-4-yloxy)piperidin-1-yl)(2-(pyrimidin-2-yl)phenyl)methanone

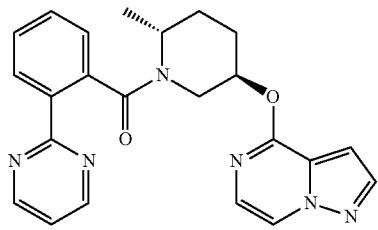 [SMILES: C[C@@H]1CC[C@@H](Oc2nccn3nccc23)CN1C(=O)c1ccccc1-c1ncccn1]

Scheme for the Preparation of Example 85

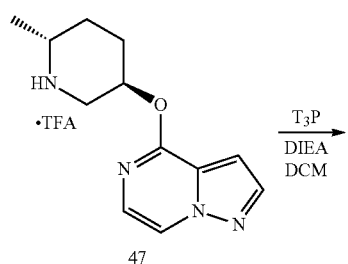

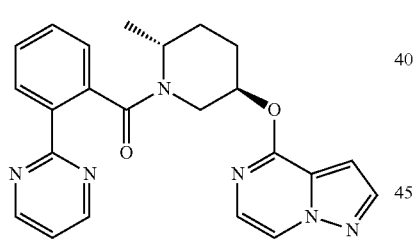

Example 85

Step 1: (2-(2H-1,2,3-triazol-2-yl)thiophen-3-yl)((2R,5R)-2-methyl-5-(pyrazolo[1,5-a]pyrazin-4-yloxy)piperidin-1-yl)methanone (Example 85)

To a solution of compound 47 (example 70, step 2) (30 mg, 0.091 mmol), 2-(pyrimidin-2-yl)benzoic acid (52 mg, 0.26 mmol) and DIEA (50 mg, 0.39 mmol) in DCM (2 mL) was added T$_3$P (1.5 mL) at 0° C. The resulting mixture was stirred at 50° C. overnight. After cooling to RT, the mixture was concentrated in vacuo and the residue was purified by Prep-HPLC to give the title compound (3.10 mg) as a white solid. LRMS m/z (M+H) 415.1 found, 415.1 required.

Example 86

(2-(2H-1,2,3-triazol-2-yl)phenyl)((2R,5R)-2-methyl-5-(pyrazolo[1,5-a]pyrazin-4-ylamino)piperidin-1-yl)methanone

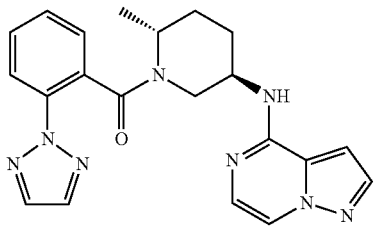

Scheme for the Preparation of Example 86

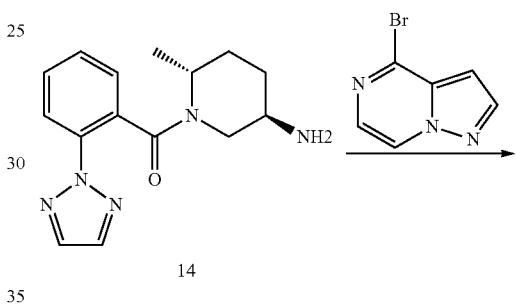

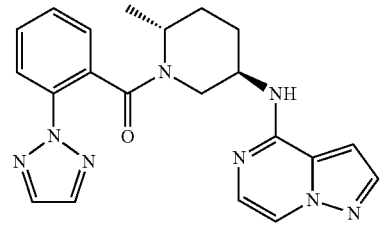 [SMILES: C[C@@H]1CC[C@@H](Nc2nccn3nccc23)CN1C(=O)c1ccccc1-n1nccn1]

Example 86

Step 1: (2-(2H-1,2,3-triazol-2-yl)phenyl)((2R,5R)-2-methyl-5-(pyrazolo[1,5-a]pyrazin-4-ylamino)piperidin-1-yl)methanone (Example 86)

To a solution of compound 14 (example 19, step 2) (50 mg, 0.17 mmol) in DMF (3 mL) was added 4-bromopyrazolo[1,5-a]pyrazine (35 mg, 0.174 mmol), Cs$_2$CO$_3$ (170 mg, 0.52 mmol) and Pd(dppf)Cl$_2$ (10 mg) at RT. The reaction mixture was stirred at 80° C. under N$_2$ overnight. After cooling to RT, the mixture was concentrated in vacuo and purified by Prep-HPLC to give the title compound (12.9 mg) as a yellow solid. LRMS m/z (M+H) 403.1 found, 403.1 required.

Example 87

(2-(2H-1,2,3-triazol-2-yl)phenyl)((2R,5R)-2-methyl-5-(pyrazolo[1,5-a]pyrazin-4-ylthio)piperidin-1-yl)methanone

Example 88

(2-(2H-1,2,3-triazol-2-yl)phenyl)((2R,5R)-5-((3-bromopyrazolo[1,5-a]pyrazin-4-yl)oxy)-2-methylpiperidin-1-yl)methanone

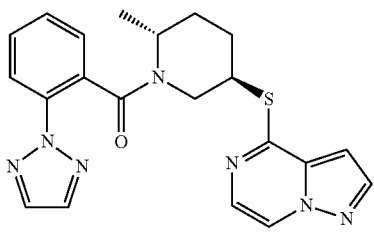 [SMILES: C[C@@H]1CC[C@@H](Sc2nccn3nccc23)CN1C(=O)c1ccccc1-n1nccn1]

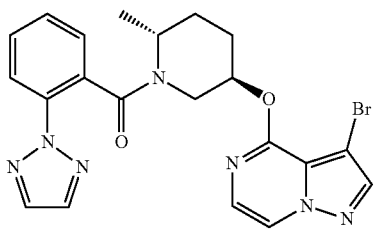 [SMILES: C[C@@H]1CC[C@@H](Oc2nccn3ncc(Br)c23)CN1C(=O)c1ccccc1-n1nccn1]

Scheme for the Preparation of Example 87

Scheme for the Preparation of Example 88

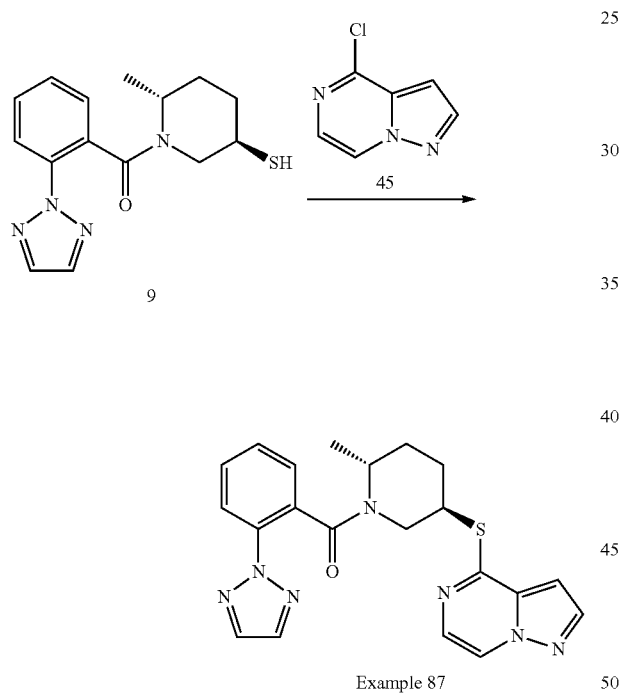

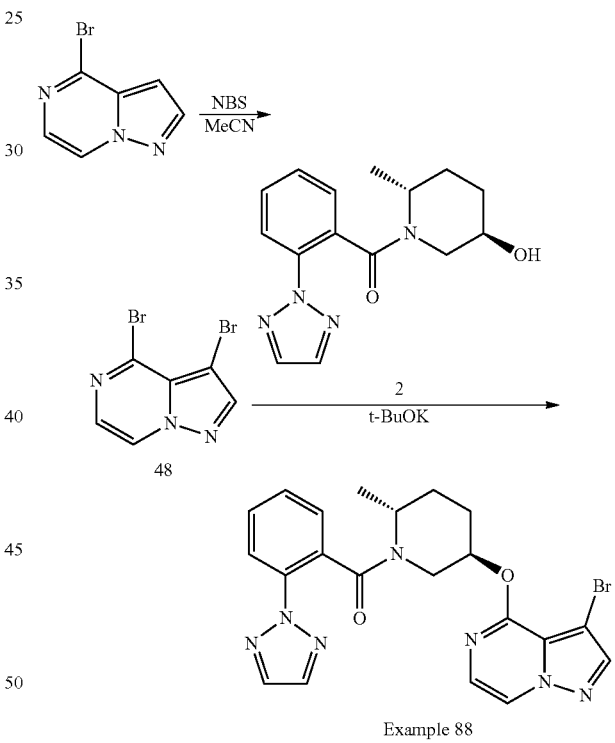

(2-(2H-1,2,3-triazol-2-yl)phenyl)((2R,5R)-2-methyl-5-(pyrazolo[1,5-a]pyrazin-4-ylamino)piperidin-1-yl)methanone (Example 87)

To a solution of compound 9 (example 5, step 5) (50 mg, 0.17 mmol) in DMF (3 mL) were added compound 45 (example 69, step 3) (35 mg, 0.17 mmol), Cs$_2$CO$_3$ (170 mg, 0.52 mmol) and Pd(dppf)Cl$_2$ (10 mg) at RT. The reacting mixture was stirred at 80° C. under N$_2$ overnight. After cooling to RT, the mixture was concentrated in vacuo and purified by Prep-HPLC to give the title compound (12.9 mg) as a yellow solid. LRMS m/z (M+H) 403.1 found, 403.1 required.

Step 1: 3,4-dibromopyrazolo[1,5-a]pyrazine (48)

To a solution of 4-bromopyrazolo[1,5-a]pyrazine (50 mg, 0.25 mmol) in acetonitrile (2 mL) was added NBS (45 mg, 0.25 mL) at RT. The resulting mixture was stirred at 50° C. for 1 hour. After cooling to RT, the mixture was concentrated in vacuo. The residue was purified by Prep-TLC (25% EtOAc in petroleum ether) to give the title compound (60 mg) as a white solid.

LRMS m/z (M+H) 276.1, 278.1, 280.1 found, 276.1, 278.1, 280.1 required.

Step 2: (2-(2H-1,2,3-triazol-2-yl)phenyl)((2R,5R)-5-((3-bromopyrazolo[1,5-a]pyrazin-4-yl)oxy)-2-methylpiperidin-1-yl)methanone (Example 88)

To a solution of compound 2 (example 1, step 2) (50 mg, 0.18 mmol) in DMF (3 mL) was added t-BuOK (39 mg, 0.35 mmol) at 0° C. The mixture was stirred at 0° C. for 0.5 hour, then the product from step 1 (49 mg, 0.18 mmol) was added at 0° C. The resulting mixture was stirred at RT for another 2 hours. The mixture was concentrated in vacuo and purified by Prep-HPLC to give the title compound (13.3 mg) as a white solid. LRMS m/z (M+H) 482.1, 484.1 found, 482.1, 484.1 required.

Example 89

(2-(2H-1,2,3-triazol-2-yl)phenyl)((2R,5R)-2-methyl-5-((3-methylpyrazolo[1,5-a]pyrazin-4-yl)oxy)piperidin-1-yl)methanone

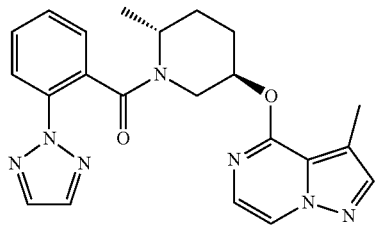 [SMILES: Cc1cnn2ccnc(O[C@@H]3CC[C@@H](C)N(C(=O)c4ccccc4-n4nccn4)C3)c12]

Scheme for the Preparation of Example 89

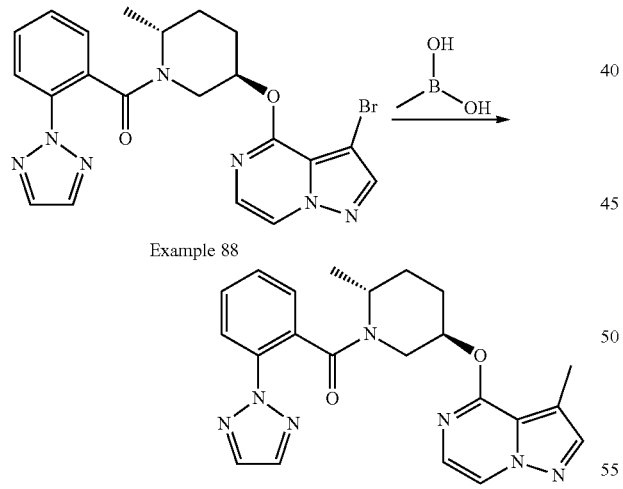

Example 89

(2-(2H-1,2,3-triazol-2-yl)phenyl)((2R,5R)-2-methyl-5-((3-methylpyrazolo[1,5-a]pyrazin-4-yl)oxy)piperidin-1-yl)methanone (Example 89)

A mixture of Example 88 (30 mg, 0.06 mmol), methylboronic acid (5.6 mg, 0.09 mmol), Na$_2$CO$_3$ (16.5 mg, 0.16 mmol), and Pd(dppf)Cl$_2$ (2.3 mg, 0.003 mmol) in DME:H$_2$O (3:1) (2 mL) was heated to 95° C. under N$_2$ protection overnight. LCMS indicated that starting material disappeared, the mixture was filtered, and the filtrate was purified by Prep-HPLC to give the title compound (9.0 mg) as a white solid. LRMS m/z (M+H) 418.1 found, 418.1 required.

Example 90

(2-(2H-1,2,3-triazol-2-yl)phenyl)((2R,5R)-2-methyl-5-(pyrazolo[1,5-a]pyridin-4-yloxy)piperidin-1-yl)methanone

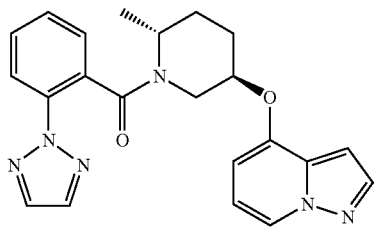 [SMILES: C[C@@H]1CC[C@@H](Oc2cccn3nccc23)CN1C(=O)c1ccccc1-n1nccn1]

Scheme for the Preparation of Example 90

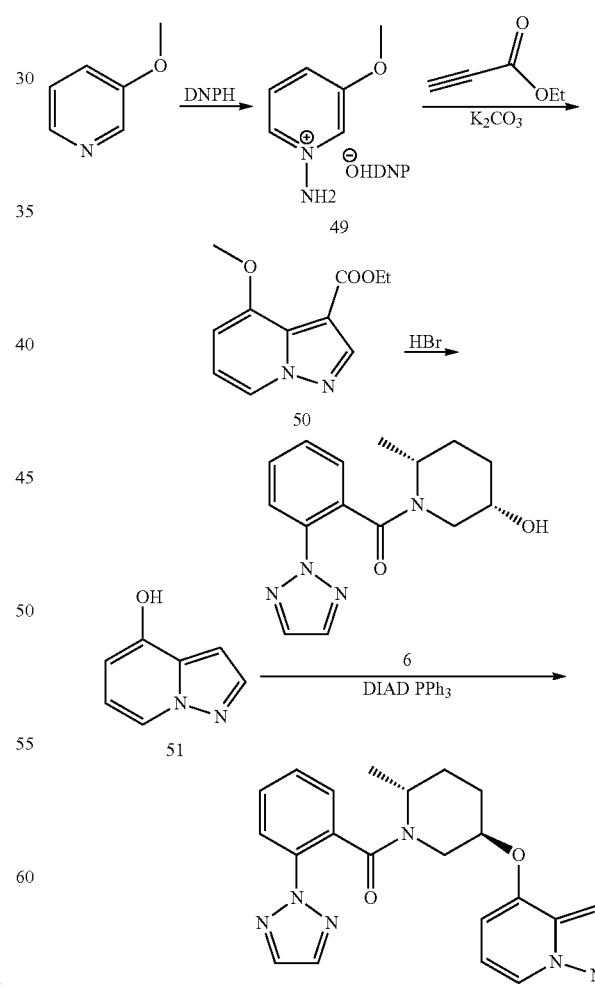

Example 90

Step 1: (2,4-dinitrophenoxy)(3-methoxypyridin-1-ium-1-yl)amide (49)

A mixture of 3-methoxypyridine (500 mg, 4.6 mmol) and O-(2,4-dinitrophenyl)hydroxyl-amine (915 mg, 4.6 mmol) in MeCN (20 mL) was stirred at 40° C. for 16 hours. After cooling to RT, the mixture was concentrated in vacuo to give the title compound (1.50 g) as yellow oil.

Step 2: ethyl 4-methoxypyrazolo[1,5-a]pyridine-3-carboxylate (50)

To a solution of the product from step 1 (1.50 g, 4.9 mmol) in DMF (20 mL) was added $K_2CO_3$ (1.4 g, 9.8 mmol). The mixture was stirred at 0° C. for 10 minutes, then ethyl propiolate (480 mg, 4.9 mmol) was added. The mixture was stirred at RT for 16 hours, diluted with water and extracted with EtOAc (50 mL×3). The combined organic layer was dried over sodium sulfate, filtered and concentrated in vacuo. The residue was purified by Prep-HPLC to give the title compound (850 mg) as yellow oil. LRMS m/z (M+H) 221.1 found, 221.1 required.

Step 3: pyrazolo[1,5-a]pyridin-4-ol (51)

A mixture of the product from step 2 (500 mg, 2.26 mmol) in 40% HBr (20 mL) was stirred at 120° C. for 16 hours. After cooling to RT, the mixture was concentrated in vacuo to give a residue, which was neutralized with saturated $NaHCO_3$ aqueous solution to pH~7, extracted with the mixed solvent (DCM:i-Propanol=4:1) (500 mL×3). The organic layer was combined, dried over $MgSO_4$, filtered and concentrated in vacuo. The residue was purified by silica chromatography (10% methanol in DCM) to give the title compound (290.0 mg) as yellow oil. LRMS m/z (M+H) 135.1 found, 135.1 required.

Step 4: (2-(2H-1,2,3-triazol-2-yl)phenyl)((2R,5R)-2-methyl-5-(pyrazolo[1,5-a]pyridin-4-yloxy) piperidin-1-yl)methanone (Example 90)

To a solution of compound 6 (example 5, step 2) (106 mg, 0.37 mmol), the product from step 3 (50 mg, 0.37 mmol) and $PPh_3$ (194 mg, 0.74 mmol) in THF (3 mL) was added DIAD (149 mg, 0.74 mmol) at 0° C. under $N_2$. The mixture was stirred at RT for 3 hours. The mixture was purified by Prep-HPLC to give the title compound (3.9 mg) as yellow oil. LRMS m/z (M+H) 403.2 found, 403.2 required.

Example 91

(2-(2H-1,2,3-triazol-2-yl)phenyl)((2R,5R)-2-methyl-5-(oxazolo[5,4-b]pyridin-7-yloxy)piperidin-1-yl)methanone

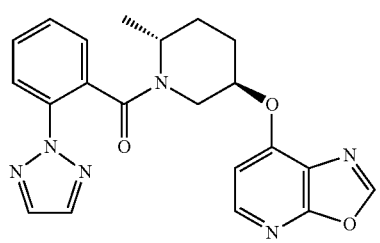 [SMILES: C[C@@H]1CC[C@@H](Oc2ccnc3ocnc23)CN1C(=O)c1ccccc1-n1nccn1]

Scheme for the Preparation of Example 91

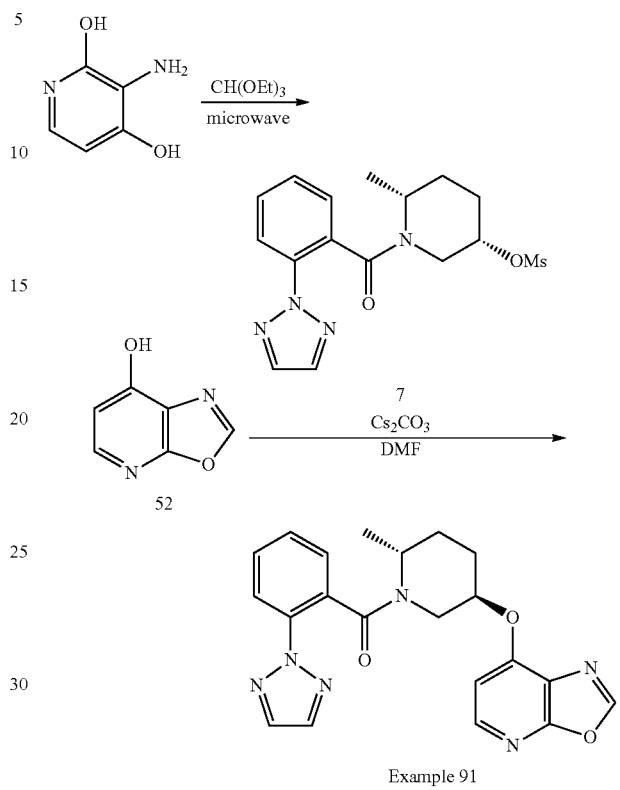

Example 91

Step 1: oxazolo[5,4-b]pyridin-7-ol (52)

A solution of 3-aminopyridine-2,4-diol (200 mg, 1.59 mmol) and triethoxymethane (3 mL) was stirred at 150° C. for 0.5 hour under microwave. After cooling to RT, the mixture was quenched with saturated aqueous sodium bicarbonate and extracted with EtOAc (30 mL×3). The combined organic layer was washed with brine, dried over magnesium sulfate, filtered, and the filtrate was concentrated in vacuo. The residue was purified by silica gel gradient chromatography (50% EtOAc in petroleum ether) to give the title compound (120 mg) as a pale yellow solid. LRMS m/z (M+H) 137.1 found, 137.0 required.

Step 2: (2-(2H-1,2,3-triazol-2-yl)phenyl)((2R,5R)-2-methyl-5-(oxazolo[5,4-b]pyridin-7-yloxy)piperidin-1-yl)methanone (Example 91)

To a solution of the product from step 1 (100 mg, 0.27 mmol) in DMF (2 mL) was added compound 7 (example 5, step 3) (45 mg, 0.33 mmol) and $Cs_2CO_3$ (176 mg, 0.54 mmol). The resulting mixture was stirred at 80° C. for 12 hours. After cooling to RT, the mixture was quenched with water (10 mL) and extracted with EtOAc (15 mL×3). The combined organic layer was dried over $MgSO_4$, filtered and concentrated in vacuo. The residue was purified by prep-HPLC to give the title compound (16 mg) as a yellow solid. LRMS m/z (M+H) 405.1 found, 405.2 required.

Example 92

(2-(2H-tetrazol-2-yl)phenyl)((2R,5R)-2-methyl-5-(oxazolo [5,4-b]pyridin-7-yloxy)piperidin-1-yl) methanone

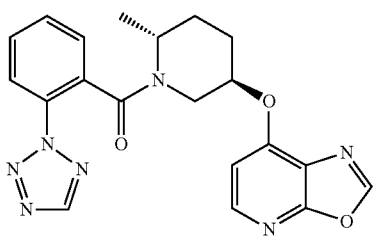 [SMILES: C[C@@H]1CC[C@@H](Oc2ccnc3ocnc23)CN1C(=O)c1ccccc1-n1ncnn1]

Scheme for the Preparation of Example 92

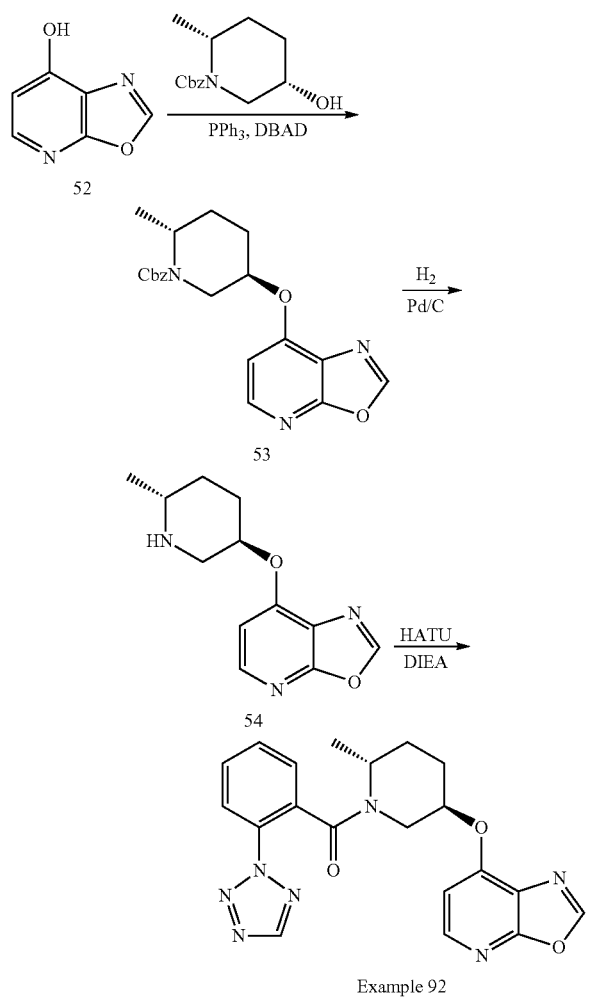

Step 1: (2R,5R)-benzyl 2-methyl-5-(oxazolo[5,4-b] pyridin-7-yloxy)piperidine-1-carboxylate (53)

To a solution of compound 52 (example 91, step 1) (1.6 g, 11.6 mmol) in THF (20 mL) was added Ph₃P (4.7 g, 17.4 mmol), DBAD (4 g, 17.4 mmol) and (2R,5S)-benzyl 5-hydroxy-2-methylpiperidine-1-carboxylate (3.5 g, 14.0 mmol). The resulting mixture was stirred at 50° C. for 12 hours. After cooling to RT, the mixture was poured into water and extracted with EtOAc (50 mL×3). The combined organic layer was washed with brine, dried over MgSO₄, filtered and concentrated in vacuo. The residue was purified by flash column chromatography (10%-20% EtOAc in petroleum ether) to give the title compound (2 g) as a yellow solid. LRMS m/z (M+H) 368.1 found, 368.2 required.

Step 2: 7-(((3R,6R)-6-methylpiperidin-3-yl)oxy) oxazolo[5,4-b]pyridine (54)

A mixture of the product from step 1 (1.5 g, 4.1 mmol) and Pd/C (600 mg) in methanol (25 mL) was stirred at RT under 50 Psi H₂ for 5 hours. Then the mixture was filtered and the filtrate was concentrated in vacuo to give the title compound (758 mg) as white solid, which was used in the next step without further purification. LRMS m/z (M+H) 234.2 found, 234.1 required.

Step 3: (2-(2H-tetrazol-2-yl)phenyl)((2R,5R)-2-methyl-5-(oxazolo[5,4-b]pyridin-7-yloxy)piperidin-1-yl)methanone (Example 92)

A solution of the product from step 2 (50 mg, 0.21 mmol), 2-(2H-tetrazol-2-yl)benzoic acid (49 mg, 0.25 mmol), DIPEA (108 mg, 0.84 mmol) and HATU (95 mg, 0.25 mmol) in DMF (1 mL) was stirred at RT overnight. The mixture was diluted with water (100 mL) and extracted with EtOAc (100 mL×3). The combined organic layer was washed with brine, dried over Na₂SO₄, filtered and concentrated in vacuo. The residue was purified by chromatography on silica (50% EtOAc in petroleum ether) to give the title compound (10 mg) as a white solid.

LRMS m/z (M+H) 406.2 found, 406.2 required.

The following compounds were prepared according to the general procedure of Example 92 and the procedures herein. The starting materials are either commercially available or may be prepared from commercially available reagents using conventional reactions well known in the art.

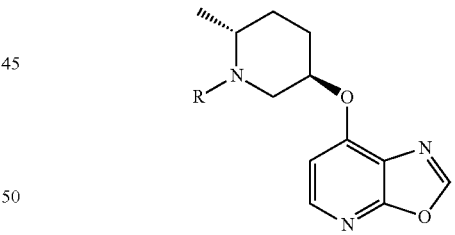

TABLE 11

| Example | R | Chemical Name | LRMS or HRMS (M + H⁺) |
|---|---|---|---|
| 93 | (methyl benzoate with carbonyl linker) | methyl 2-((2R,5R)-2-methyl-5-(oxazolo[5,4-b]pyridin-7-yloxy)piperidine-1-carbonyl)benzoate | Calc'd 396.2, found 396.1 |

TABLE 11-continued

| Example | R | Chemical Name | LRMS or HRMS (M + H+) |
|---|---|---|---|
| 94 | (structure: 2-ethoxyphenyl ketone) | (2-ethoxyphenyl)((2R,5R)-2-methyl-5-(oxazolo[5,4-b]pyridin-7-yloxy)piperidin-1-yl)methanone | Calc'd 382.2, found 382.1 |

Example 95

(2-(2H-1,2,3-triazol-2-yl)phenyl)((2R,5R)-2-methyl-5-((1-methyl-1H-pyrazolo[4,3-c]pyridin-4-yl)oxy)piperidin-1-yl)methanone Scheme for the Preparation of Example 95

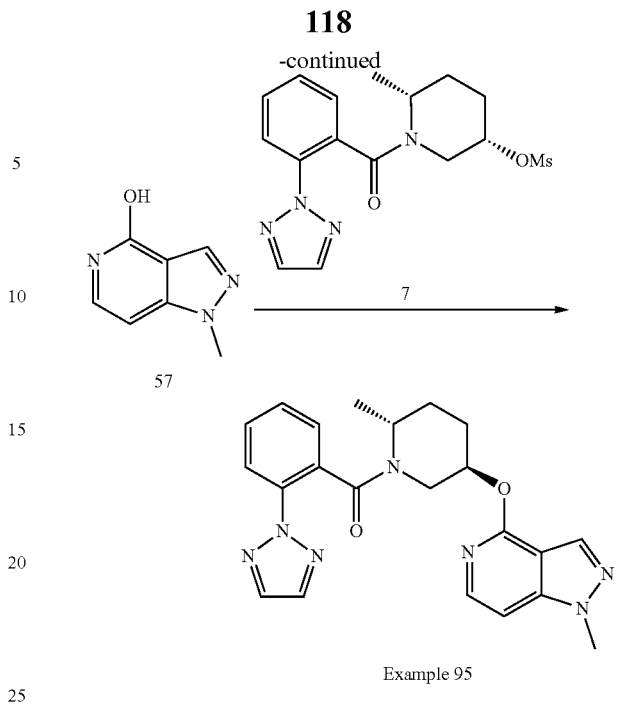

Step 1: 4-chloro-1-methyl-1H-pyrazolo[4,3-c]pyridine (55) and 4-chloro-2-methyl-2H-pyrazolo[4,3-c]pyridine (56)

To a solution of 4-chloro-1H-pyrazolo[4,3-c]pyridine (100 mg, 0.65 mmol) in DMF (3 mL) was added NaH (78 mg, 1.95 mmol, 60 wt % in oil) at 0° C. under $N_2$. The mixture was stirred at 0° C. for 40 minutes. MeI (277 mg, 1.95 mmol) was added at 25° C. The mixture was stirred for another 2 hours. The mixture was quenched with saturated $NH_4Cl$ aqueous solution and extracted with EtOAc (20 mL×3). The combined organic layer was dried over magnesium sulfate, filtered and concentrated in vacuo. The residue was purified by Prep-HPLC to give the title compound 56 (50.2 mg) as yellow oil, 57 (30 mg) as yellow oil. LRMS m/z (M+H) 168.1, 170.1 found, 168.0, 170.1 required.

Step 2: 1-methyl-1H-pyrazolo[4,3-c]pyridin-4-ol (57)

A mixture of 55 (the product form step 1) (300 mg, 1.80 mmol), $NH_4OAc$ (3.20 g) in HOAc (4 mL) was stirred at 120° C. for 16 hours. After cooling to RT, the mixture was adjusted pH-7 with saturated $NaHCO_3$ aqueous solution and extracted with EtOAc (20 mL×3), DCM (20 ml×3), DCM:i-Propanol=4:1 (30 mL×3), respectively. The combined organic layer was dried over magnesium sulfate, filtered and concentrated in vacuo to give the title compound (500 mg) as yellow solid. LRMS m/z (M+H) 150.1 found, 150.1 required.

Step 3: (2-(2H-1,2,3-triazol-2-yl)phenyl)((2R,5R)-2-methyl-5-((1-methyl-1H-pyrazolo[4,3-c]pyridin-4-yl)oxy)piperidin-1-yl)methanone (Example 95)

A mixture of the product from step 2 (50 mg, 0.33 mmol), compound 7 (example 5, step 3) (120 mg, 0.33 mmol) and $Cs_2CO_3$ (323 mg, 0.99 mmol) in DMF (3 mL) was stirred at 80° C. for 16 hours. After cooling to RT, the mixture was filtered and purified by Prep-HPLC to give the title compound (15.7 mg) as yellow oil. LRMS m/z (M+H) 418.1 found, 418.2 required.

Example 96

(2-(2H-1,2,3-triazol-2-yl)phenyl)((2R,5R)-2-methyl-5-((1-methyl-1H-pyrazolo[4,3-c]pyridin-4-yl)amino)piperidin-1-yl)methanone

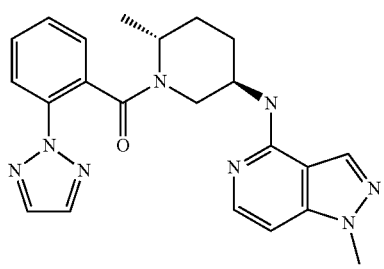 [SMILES: C[C@@H]1CC[C@@H](Nc2nccc3c2cnn3C)CN1C(=O)c1ccccc1-n1nccn1]

Scheme for the Preparation of Example 96

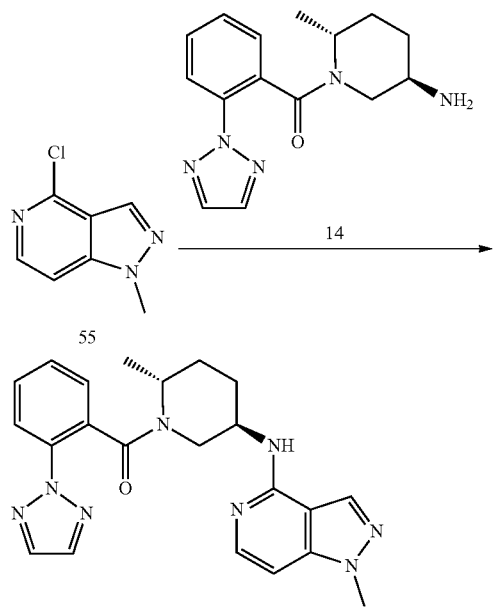

Example 96

Step 1: (2-(2H-1,2,3-triazol-2-yl)phenyl)((2R,5R)-2-methyl-5-((1-methyl-1H-pyrazolo[4,3-c]pyridin-4-yl)amino)piperidin-1-yl)methanone (Example 96)

A mixture of compound 55 (example 95, step 1) (11.8 mg, 0.07 mmol) and (2-(2H-1,2,3-triazol-2-yl)phenyl)((2R,5R)-5-amino-2-methylpiperidin-1-yl)methanone (20.3 mg, 0.07 mmol) was stirred at 120° C. for 16 hours. After cooling to RT, the mixture was purified by Prep-HPLC to give the title compound (10.1 mg) as yellow oil. LRMS m/z (M+H) 417.2 found, 417.2 required.

The following compound was prepared according to the general procedure of last step provided in Example 96. The starting materials are either commercially available or may be prepared from commercially available reagents using conventional reactions well known in the art.

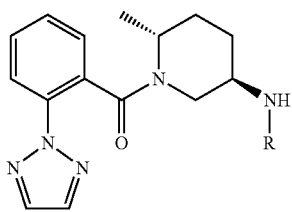

TABLE 12

| Example | R | Chemical Name | LRMS or (M + H⁺) |
|---------|---|---------------|------------------|
| 97 | (structure) | (2-(2H-1,2,3-triazol-2-yl)phenyl)((2R,5R)-2-methyl-5-((2-methyl-2H-pyrazolo[4,3-c]pyridin-4-yl)amino)piperidin-1-yl)methanone | Calc'd 417.2, found 417.2 |

Example 98

(2-(2H-1,2,3-triazol-2-yl)phenyl)((2R,5R)-2-methyl-5-((1-methyl-1H-imidazo[4,5-c]pyridin-4-yl)oxy)piperidin-1-yl)methanone

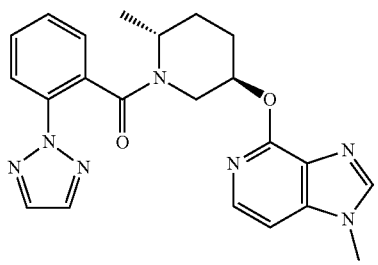 [SMILES: C[C@@H]1CC[C@@H](Oc2nccc3c2ncn3C)CN1C(=O)c1ccccc1-n1nccn1]

Scheme for the Preparation of Example 98

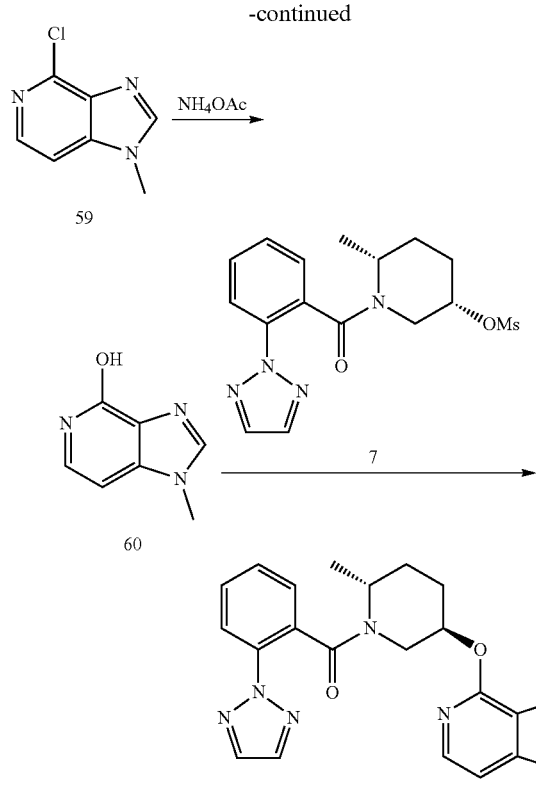

Example 96

Step 1: 4-chloro-3-methyl-3H-imidazo[4,5-c]pyridine (58) and 4-chloro-1-methyl-1H-imidazo[4,5-c]pyridine (59)

To a solution of 4-chloro-3H-imidazo[4,5-c]pyridine (100 mg, 0.65 mmol) in DMF (3 mL) was added NaH (78 mg, 1.95 mmol, 60 wt % in oil) at 0° C. under N₂. The mixture was stirred at 0° C. for 40 minutes. MeI (277 mg, 1.95 mmol) was added at 0° C. And the mixture was stirred for another 2 hours at RT. The mixture was quenched with saturated NH₄Cl aqueous solution, extracted with EtOAc (20 mL×3). The combined organic layer was dried over magnesium sulfate, filtered and concentrated in vacuo. The residue was purified by Prep-HPLC to give the title compound 58 (40.3 mg) as yellow oil, compound 59 (41.0 mg) as yellow oil. LRMS m/z (M+H) 168.2, 170.2 found, 168.0, 170.2 required.

Step 2: 1-methyl-1H-imidazo[4,5-c]pyridin-4-ol (60)

A mixture of compound 59 (the product form step 1) (300 mg, 1.80 mmol) and NH₄OAc (3.20 g) in acetic acid (4 mL) was stirred at 120° C. for 16 hours. After cooling to RT, the mixture was adjusted to pH 7 with saturated NaHCO₃ aqueous solution and extracted with EtOAc (20 mL×3), DCM (20 mL×3), DCM: i-Propanol=4:1 (30 mL×3), respectively. The combined organic layer was dried over magnesium sulfate, filtered and concentrated in vacuo to give the title compound (500 mg) as yellow solid. LRMS m/z (M+H) 150.1 found, 150.1 required.

Step 3: (2-(2H-1,2,3-triazol-2-yl)phenyl)((2R,5R)-2-methyl-5-((1-methyl-1H-imidazo[4,5-c]pyridin-4-yl)oxy)piperidin-1-yl)methanone (Example 98)

A mixture of the product from step 2 (50 mg, 0.33 mmol), compound 7 (example 5, step 3) (120 mg, 0.33 mmol), Cs₂CO₃ (323 mg, 0.99 mmol) in DMF (3 mL) was stirred at 80° C. for 16 hours. After cooling to RT, the mixture was filtered and the filtrate was purified by Prep-HPLC to give the title compound (15.7 mg) as yellow oil. LRMS m/z (M+H) 418.1 found, 418.2 required.

Example 99

(2-(2H-1,2,3-triazol-2-yl)phenyl)((2R,5R)-2-methyl-5-((3-methyl-3H-imidazo[4,5-c]pyridin-4-yl)oxy)piperidin-1-yl)methanone

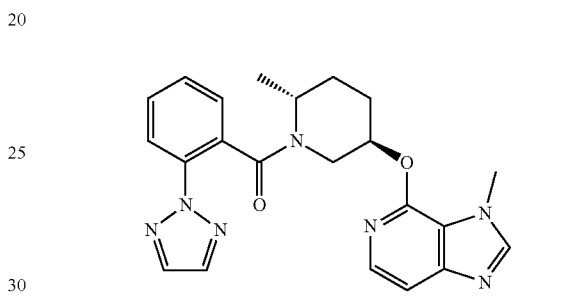

Scheme for the Preparation of Example 99

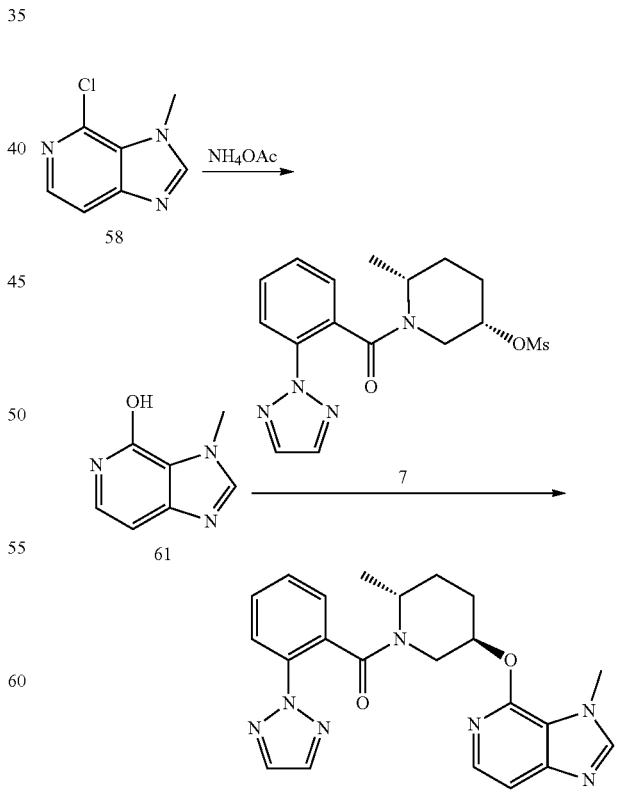

Example 99

123

Step 1: 3-methyl-3H-imidazo[4,5-c]pyridin-4-ol (61)

A mixture of compound 58 (example 98, step 1) (180 mg, 1.07 mmol) and NH₄OAc (6.0 g) in acetic acid (4 mL) was stirred at 120° C. for 16 hours. After cooling to RT, the mixture was adjusted to pH=~7 with saturated NaHCO₃ aqueous solution and extracted with EtOAc (20 mL×3), DCM (20 mL×3), DCM: i-Propanol=4:1 (30 mL×3) for three times. The combined organic layer was dried over magnesium sulfate, filtered and concentrated in vacuo to give the title compound (350 mg) as yellow solid.

LRMS m/z (M+H) 150.1 found, 150.1 required.

Step 2: (2-(2H-1,2,3-triazol-2-yl)phenyl)((2R,5R)-2-methyl-5-((3-methyl-3H-imidazo[4,5-c]pyridin-4-yl)oxy)piperidin-1-yl)methanone (Example 99)

A mixture of the product from step 1 (50 mg, 0.33 mmol), compound 7 (example 5, step 3) (120 mg, 0.33 mmol), Cs₂CO₃ (323 mg, 0.99 mmol) in DMF (3 mL) was stirred at 80° C. for 16 hours. After cooling to RT, the mixture was filtered and the filtrate was purified by Prep-HPLC to give the title compound (32.8 mg) as yellow oil. LRMS m/z (M+H) 418.1 found, 418.2 required.

Example 100

(2-(2H-1,2,3-triazol-2-yl)phenyl)((2R,5R)-2-methyl-5-((3-methyl-3H-imidazo[4,5-c]pyridin-4-yl)amino)piperidin-1-yl)methanone

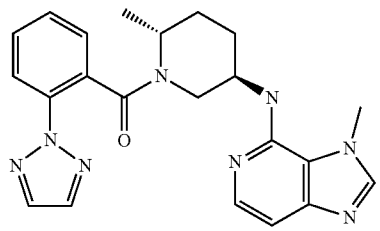 [SMILES: C[C@@H]1CC[C@@H](Oc2nccc3ncn(C)c23)CN1C(=O)c1ccccc1-n1nccn1]

Scheme for the Preparation of Example 100

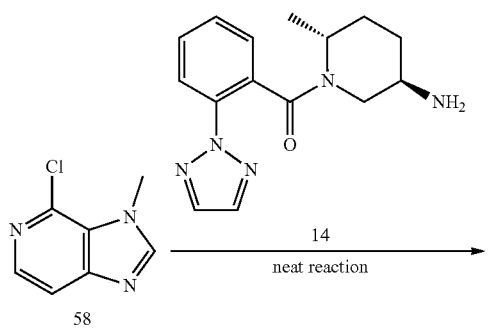

124

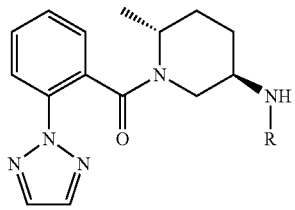

Example 100

Step 1: (2-(2H-1,2,3-triazol-2-yl)phenyl)((2R,5R)-2-methyl-5-((3-methyl-3H-imidazo[4,5-c]pyridin-4-yl)amino)piperidin-1-yl)methanone (Example 100)

A mixture of compound 59 (example 98, step 1) (40 mg, 0.24 mmol) and compound 14 (example 19, step 2) (60 mg, 0.24 mmol) was stirred at 120° C. for 16 hours. After cooling to RT, the mixture was purified by Prep-HPLC to give the title compound (4 mg) as yellow oil.

LRMS m/z (M+H) 417.2 found, 417.2 required.

The following compound was prepared according to the general procedure of last step provided in Example 100. The starting materials are either commercially available or may be prepared from commercially available reagents using conventional reactions well known in the art.

TABLE 13

| Example | R | Chemical Name | LRMS or (M + H⁺) |
|---|---|---|---|
| 101 | | (2-(2H-1,2,3-triazol-2-yl)phenyl)((2R,5R)-2-methyl-5-((1-methyl-1H-imidazo[4,5-c]pyridin-4-yl)amino)piperidin-1-yl)methanone | Calc'd 417.2, found 417.2 |

Example 102

(2-(2H-1,2,3-triazol-2-yl)phenyl)((2R,5R)-5-(imidazo[1,5-a]pyrazin-8-yloxy)-2-methylpiperidin-1-yl)methanone

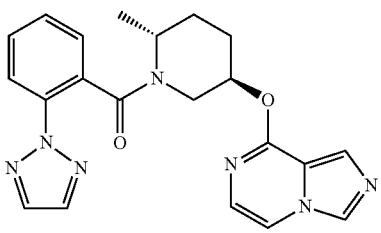 [SMILES: C[C@@H]1CC[C@@H](Oc2nccn3cncc23)CN1C(=O)c1ccccc1-n1nccn1]

Scheme for the Preparation of Example 102

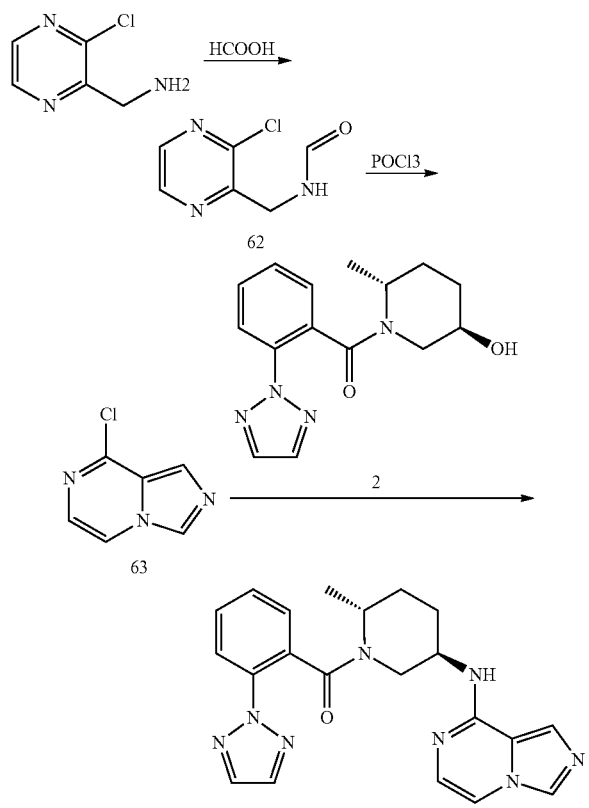

Step 1: N-((3-chloropyrazin-2-yl)methyl)formamide (62)

To a solution of (3-chloropyrazin-2-yl)methanamine (1.0 g, 5.55 mmol) in DCM (15 mL) was added EDCI (1.59 g, 8.33 mmol), HOBT (1.12 g, 8.33 mmol), DIEA (2.1 g, 16.7 mmol) and formic acid (510 mg, 11.1 mmol). The mixture was stirred at RT for 10 min, and then DMF (2 mL) was added. The mixture was stirred at RT for 12 hours, poured into water (10 mL) and then extracted with DCM (10 mL×3). The combined organic layer was dried over magnesium sulfate, filtered and concentrated in vacuo to give the title compound (600 mg) as yellow oil.

LRMS m/z (M+H) 172.1 found, 172.1 required.

Step 2: 8-chloroimidazo[1,5-a]pyrazine (63)

To a solution of the product from step 1 (200 mg, 1.17 mmol) in MeCN (5 mL) was added DMF (0.5 mL) and POCl₃ (0.5 mL). The mixture was stirred at 60° C. for 30 min. After cooling to RT, the mixture was concentrated in vacuo to remove POCl₃. The residue was poured into water (5 mL) and stirred for 20 min, and then extracted with EtOAc (5 mL×5). The combined organic layer was dried over magnesium sulfate, filtered, and concentrated in vacuo to provide the title compound (40 mg) as a yellow solid.

LRMS m/z (M+H) 154.1 found, 154.1 required.

Step 3: (2-(2H-1,2,3-triazol-2-yl)phenyl)((2R,5R)-5-(imidazo[1,5-a]pyrazin-8-yloxy)-2-methylpiperidin-1-yl)methanone (Example 102)

To a solution of compound 2 (example 1, step 2) (40 mg, 0.14 mmol) in DMF (3 mL) was added NaH (17 mg, 0.42 mmol, 60 wt % in oil) at 0° C. After the mixture was stirred at 0° C. for 0.5 hour, the product from step 2 (22 mg, 0.140 mmol) was added at 0° C. The resulting mixture was stirred at RT for another 2 hours, quenched by water (0.5 mL) and concentrated in vacuo. The residue was purified by Prep-HPLC to give the title compound (35.8 mg) as a white solid.

LRMS m/z (M+H) 404.1 found, 404.1 required.

Example 103

(2-(2H-1,2,3-triazol-2-yl)phenyl)((2R,5R)-2-methyl-5-((3-methylimidazo[1,5-a]pyrazin-8-yl)oxy)piperidin-1-yl)methanone

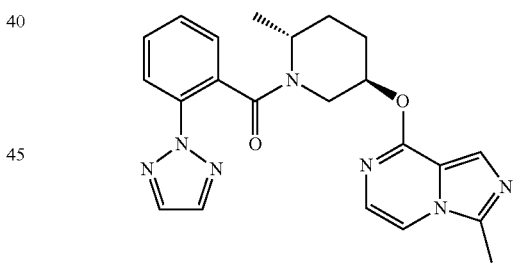

Scheme for the Preparation of Example 103

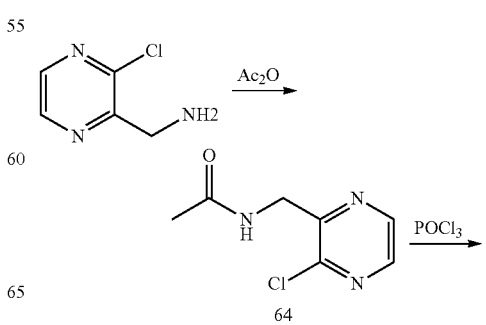

127

-continued

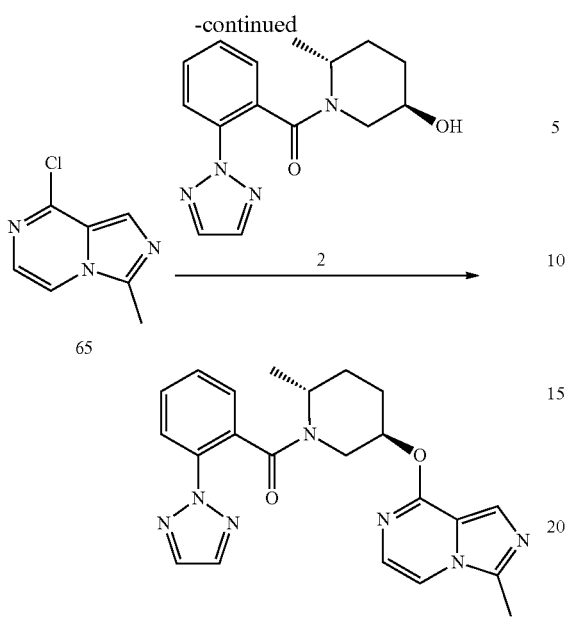

Example 103

Step 1: N-((3-chloropyrazin-2-yl)methyl)acetamide (64)

To a solution of (3-chloropyrazin-2-yl)methanamine (500 mg, 2.78 mmol) in DCM (10 mL) was added DMAP (50 mg, 0.41 mmol), DIEA (1.79 g, 13.9 mmol) and acetic anhydride (850 mg, 8.33 mmol). The mixture was stirred at RT for 12 hours, poured into water (10 mL) and extracted with DCM (10 mL×3). The combined organic layer was dried over magnesium sulfate, filtered and concentrated in vacuo to give the title compound (400 mg) as yellow oil.
LRMS m/z (M+H) 186.1 found, 186.1 required.

Step 2: 8-chloro-3-methylimidazo[1,5-a]pyrazine (65)

To a solution of the product from step 1 (200 mg, 1.08 mmol) in MeCN (3 mL) was added DMF (3 mL) and POCl$_3$ (0.5 mL). The mixture was stirred at 60° C. for 30 min. After cooling to RT, the mixture was concentrated in vacuo to remove the excess of POCl$_3$. The residue was poured into water (5 mL) and stirred for 20 min, and then extracted with EtOAc (5 mL×5). The combined organic layer was dried over magnesium sulfate, filtered, and concentrated in vacuo to provide the title compound (70 mg) as a yellow solid.
LRMS m/z (M+H) 168.1 found, 168.1 required.

Step 3: (2-(2H-1,2,3-triazol-2-yl)phenyl)((2R,5R)-2-methyl-5-((3-methylimidazo[1,5-a]pyrazin-8-yl)oxy)piperidin-1-yl)methanone (Example 103)

To a solution of compound 2 (example 1, step 2) (50 mg, 0.18 mmol) in DMF (3 mL) was added NaH (21 mg, 0.53 mmol, 60 wt % in oil) at 0° C. The mixture was stirred at 0° C. for 0.5 hour, then the product from step 2 (29 mg, 0.18 mmol) was added at 0° C. The residue was stirred at RT for another 2 hours. The mixture was quenched by water (0.5 mL) and concentrated in vacuo. The residue was purified by Prep-HPLC to give the title compound (42.8 mg) as a white solid. LRMS m/z (M+H) 418.1 found, 418.1 required.

128

Example 104

(2-(2H-1,2,3-triazol-2-yl)phenyl)((2R,5R)-2-methyl-5-((2-methyl-[1,2,4]triazolo[1,5-c]pyrimidin-5-yl)oxy)piperidin-1-yl)methanone

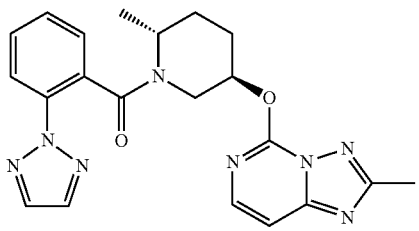 [SMILES: Cc1nc2ccnc(O[C@@H]3CC[C@@H](C)N(C(=O)c4ccccc4-n4nccn4)C3)n2n1]

Scheme for the Preparation of Example 104

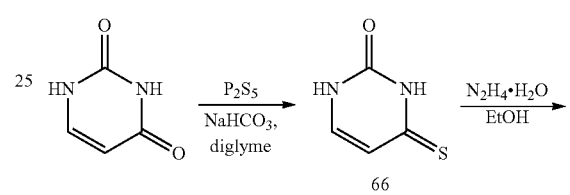

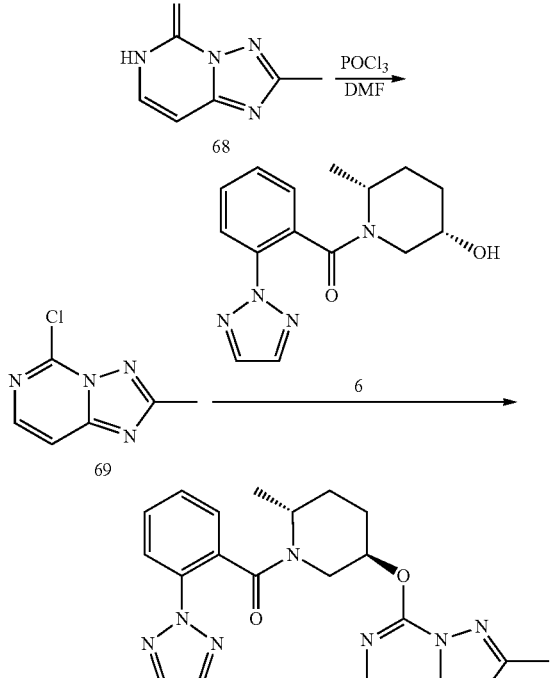

Example 104

Step 1: 4-thioxo-3,4-dihydropyrimidin-2(1H)-one (66)

To a solution of compound pyrimidine-2,4(1H,3H)-dione (10 g, 89.3 mmol) in diglyme (50 mL) were added $P_2S_5$ (19.8 g, 89.3 mmol) and $NaHCO_3$ (30 g, 357.2 mmol). The mixture was stirred at 110° C. overnight. After to cooling to RT, the mixture was poured into cold water. The precipitated solid was collected by filtration, washed with cold water, air-dried and re-crystallized with water to provide the title compound (10.1 g) as yellow solid. LRMS m/z (M+H) 129.1 found, 129.0 required.

Step 2: 4-hydrazinylpyrimidin-2(1H)-one (67)

To a solution of the product from step 1 (10.1 g, 78.9 mmol) in EtOH (100 mL) was added $N_2H_4.H_2O$ (20 mL). The mixture was refluxed for 1 hour. After cooling to RT, the mixture was filtered. The precipitated solid was washed with EtOH to give the title compound (5.0 g) as brownish gray solid. LRMS m/z (M+H) 127.1 found, 127.1 required.

Step 3: 2-methyl-[1,2,4]triazolo[1,5-c]pyrimidin-5(6H)-one (68)

A solution of the product from step 2 (2.0 g, 15.8 mmol) in triethyl orthoacetate (30 mL) was refluxed overnight. After cooling to RT, the mixture was concentrated in vacuo to give the title compound (2.10 g) as brownish gray solid. LRMS m/z (M+H) 151.1 found, 151.1 required.

Step 4: 5-chloro-2-methyl-[1,2,4]triazolo[1,5-c]pyrimidine (69)

To a solution of the product from step 3 (300 mg, 1.98 mmol) in $POCl_3$ (8 mL) was added DMF (0.1 mL). The mixture was stirred at 110° C. overnight. After cooling to RT, excess of $POCl_3$ was removed and the residue was poured into water. Then the mixture was extracted with EtOAc (30 mL×5). The combined organic layer was dried over magnesium sulfate, filtered, and concentrated in vacuo to provide the title compound (200 mg) as yellow solid. LRMS m/z (M+H) 169.0 found, 169.0 required.

Step 5: (2-(2H-1,2,3-triazol-2-yl)phenyl)((2R,5R)-2-methyl-5-((2-methyl-[1,2,4]triazolo[1,5-c]pyrimidin-5-yl)oxy)piperidin-1-yl)methanone (Example 104)

To a solution of the product from step 4 (63.4 mg, 0.42 mmol), compound 6 (example 5, step 2) (60 mg, 0.21 mmol) and $Ph_3P$ (112.5 mg, 0.42 mmol) in THF (2 mL) was added a solution of DBAD (73.0 mg, 0.42 mmol) in THF (0.5 mL) dropwise at 0° C. under $N_2$ protection. The resulting mixture was stirred at RT overnight. Then the mixture was concentrated in vacuo to give the residue which was purified by Prep-HPLC to provide the title compound (21.1 mg) as white solid. LRMS m/z (M+H) 419.2 found, 419.2 required.

Example 105

(2-(2H-1,2,3-triazol-2-yl)phenyl)((2R,5R)-2-methyl-5-((2-methyl-[1,2,4]triazolo[1,5-c]pyrimidin-5-yl)amino)piperidin-1-yl)methanone

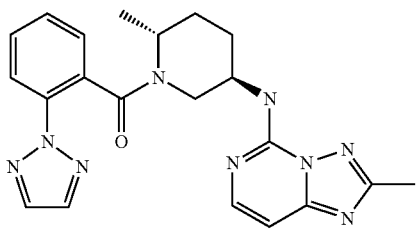 [SMILES: Cc1nc2ccnc(N[C@@H]3CC[C@@H](C)N(C(=O)c4ccccc4-n4nccn4)C3)n2n1]

Scheme for the Preparation of Example 105

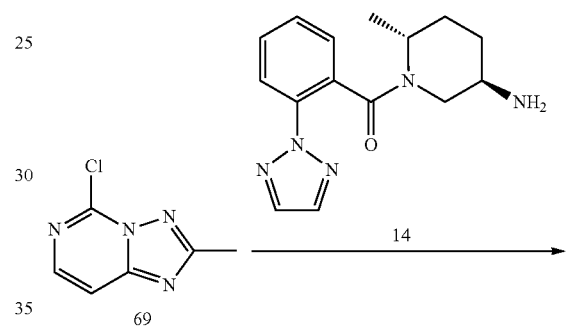

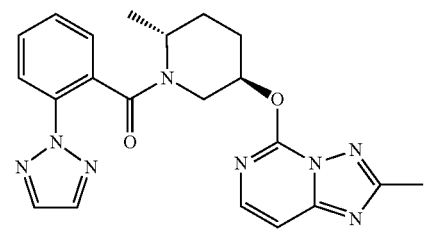

Example 105

Step 1: (2-(2H-1,2,3-triazol-2-yl)phenyl)((2R,5R)-2-methyl-5-((2-methyl-[1,2,4]triazolo[1,5-c]pyrimidin-5-yl)amino)piperidin-1-yl)methanone (Example 105)

A mixture of the compound 69 (example 104, step 4) (70.7 mg, 0.42 mmol) and compound 14 (example 19, step 2) (60 mg, 0.21 mmol) was stirred at 110° C. for 1 hour. After cooling to RT, the mixture was dissolved with DMF and purified by Prep-HPLC to give the title compound (8.35 mg) as white solid. LRMS m/z (M+H) 418.2 found, 418.2 required.

Example 106

8-(((3R,6R)-1-(2-(2H-1,2,3-triazol-2-yl)benzoyl)-6-methylpiperidin-3-yl)oxy)-2-methyl-[1,2,4]triazolo[4,3-a]pyridin-3(2H)-one

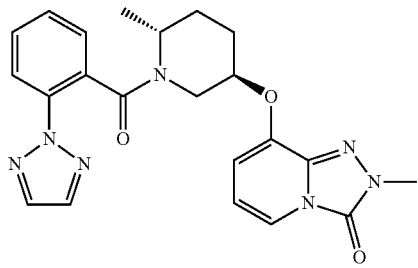 [SMILES: C[C@@H]1CC[C@@H](Oc2cccn3c(=O)n(C)nc23)CN1C(=O)c1ccccc1-n1nccn1]

Scheme for the Preparation of Example 106

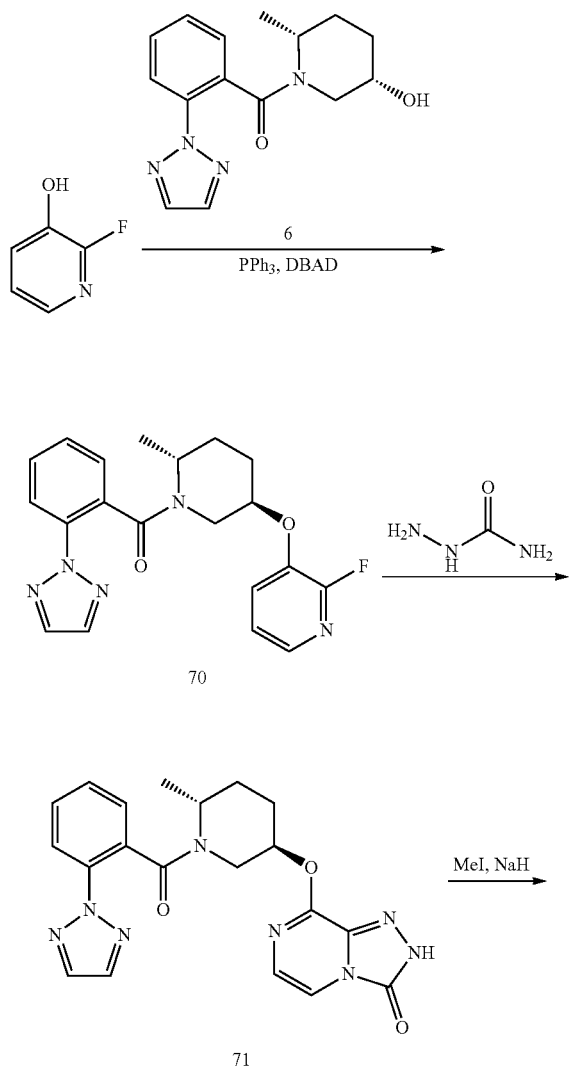

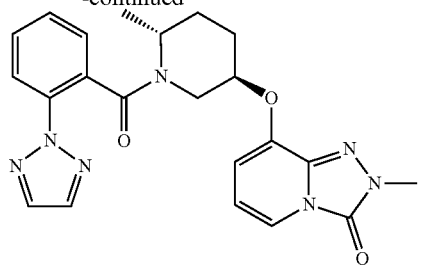

Example 106

Step 1: (2-(2H-1,2,3-triazol-2-yl)phenyl)((2R,5R)-5-((2-fluoro-1,2-dihydropyridin-3-yl)oxy)-2-methylpiperidin-1-yl)methanone (70)

To a solution of 2-fluoropyridin-3-ol (119 mg, 1.05 mmol) in THF (0.5 mL) was added compound 6 (example 5, step 2) (200 mg, 0.70 mmol) and Ph₃P (275 mg, 1.05 mmol) at RT. The resulting mixture was stirred for 10 minutes at RT, then DBAD (241 mg, 1.05 mol) was added. The resulting mixture was stirred at 50° C. for 12 hours. After cooling to RT, the mixture was quenched with water, extracted with EtOAc (40 mL×3). The combined organic layer was washed with brine, dried over Na₂SO₄ and concentrated in vacuo. The residue was purified by prep.TLC (50% EtOAc in petroleum ether) to provide the title compound (120 mg). LRMS m/z (M+H) 382.1 found, 382.1 required.

Step 2: 8-(((3R,6R)-1-(2-(2H-1,2,3-triazol-2-yl)benzoyl)-6-methylpiperidin-3-yl)oxy)-[1,2,4]triazolo[4,3-a]pyridin-3(2H)-one (71)

To a solution of the product from step 1 (50 mg, 0.13 mmol) in 2-ethoxyethanol (1.0 mL) was added hydrazinecarboxamide (19.5 mg, 0.26 mmol). The mixture was stirred at 180° C. under microwave for 1 hour. After cooling to RT, the mixture was quenched with water, extracted with EtOAc (30 mL×3). The combined organic layer was washed with brine, dried over Na₂SO₄ and concentrated in vacuo. The residue was purified by Prep-HPLC to give the title compound (20 mg). LRMS m/z (M+H) 420.1 found, 420.1 required.

Step 3: 8-(((3R,6R)-1-(2-(2H-1,2,3-triazol-2-yl)benzoyl)-6-methylpiperidin-3-yl)oxy)-2-methyl-[1,2,4]triazolo[4,3-a]pyridin-3(2H)-one (Example 106)

To a solution of the product from step 2 (30 mg, 0.071 mmol) in DMF (1.0 mL) was added NaH (5.7 mg, 0.143 mmol, 60 wt % in oil) at 0° C. The resulting mixture was stirred for half an hour, then MeI (0.1 mL) was added. The mixture was stirred at RT for 12 hours, quenched with water (5 drops) and filtered. The filtrate was purified by Prep-HPLC to give the title compound (15 mg). LRMS m/z (M+H) 434.2 found, 434.2 required.

Example B: Measurement of OX1 and OX2 Receptor Antagonistic Activity

The following table shows representative data for the compounds of the Examples as orexin receptor antagonists as determined by the assays described herein.

TABLE 14

| Example | hOX2 FLIPR IC$_{50}$ (nM) | hOX1 FLIPR IC$_{50}$ (nM) |
|---|---|---|
| 1 | 35.8 | 2374 |
| 2 | 59.0 | >10000 |
| 3 | 50.4 | >10000 |
| 4 | 31.9 | >10000 |
| 5 | 10.3 | 2389 |
| 6 | 8.0 | 1349 |
| 7 | 27.4 | >10000 |
| 8 | 39.1 | >10000 |
| 9 | 13.2 | 6697 |
| 10 | 31.2 | 2131 |
| 11 | 22.2 | >10000 |
| 12 | 46.2 | >10000 |
| 13 | 63.7 | >10000 |
| 14 | 36.8 | >10000 |
| 15 | 41.7 | >10000 |
| 16 | 33.5 | >10000 |
| 17 | 68.4 | >10000 |
| 18 | 58.7 | >10000 |
| 19 | 50.9 | >10000 |
| 20 | 49.0 | 3010 |
| 21 | 63.7 | >10000 |
| 22 | 45.4 | >10000 |
| 23 | 99.3 | >10000 |
| 24 | 88.2 | >10000 |
| 25 | 49.3 | >10000 |
| 26 | 12.1 | 1025 |
| 27 | 9.1 | 2457 |
| 28 | 9.5 | 1548 |
| 29 | 14.3 | 2555 |
| 30 | 13.9 | 916 |
| 31 | 23.7 | 1487 |
| 32 | 12.6 | 1173 |
| 33 | 8.9 | 1201 |
| 34 | 16.3 | 9061 |
| 35 | 73.7 | >10000 |
| 36 | 21.0 | 5100 |
| 37 | 29.2 | 1774 |
| 38 | 17.6 | 1791 |
| 39 | 62.6 | >10000 |
| 40 | 10.5 | 9025 |
| 41 | 45.7 | >10000 |
| 42 | 5.0 | 1795 |
| 43 | 15.7 | 1419 |
| 44 | 9.6 | 2061 |
| 45 | 108.0 | >10000 |
| 46 | 61.9 | >10000 |
| 47 | 64.9 | >10000 |
| 48 | 24.9 | >10000 |
| 49 | 51.8 | 2701 |
| 50 | 26.5 | 2132 |
| 51 | 31.8 | 8015 |
| 52 | 15.8 | 1570 |
| 53 | 21.3 | 2126 |
| 54 | 24.1 | 1443 |
| 55 | 44.9 | >10000 |
| 56 | 53.7 | >10000 |
| 57 | 13.1 | 1505 |
| 58 | 20.4 | >10000 |
| 59 | 12.8 | 4383 |
| 60 | 19.0 | 8623 |
| 61 | 170.4 | >10000 |
| 62 | 46.7 | 3853 |
| 63 | 28.2 | 3309 |
| 64 | 17.4 | 9998 |
| 65 | 24.0 | 9326 |
| 66 | 14.9 | 1234 |
| 67 | 182.0 | >10000 |
| 68 | 114.7 | >10000 |
| 69 | 26.8 | 3073 |
| 70 | 9.8 | 2208 |
| 71 | 16.0 | 7278 |
| 72 | 14.3 | 2673 |
| 73 | 14.0 | 3752 |
| 74 | 34.4 | 7495 |
| 75 | 20.6 | 1767 |
| 76 | 27.8 | >10000 |
| 77 | 27.9 | >10000 |
| 78 | 59.1 | >10000 |
| 79 | 44.2 | >10000 |
| 80 | 31.7 | 3524 |
| 81 | 51.9 | >10000 |
| 82 | 33.9 | >10000 |
| 83 | 49.1 | >10000 |
| 84 | 43.5 | >10000 |
| 85 | 15.5 | 1498 |
| 86 | 20.5 | 2753 |
| 87 | 15.7 | 830 |
| 88 | 7.3 | 512 |
| 89 | 19.2 | 938 |
| 90 | 124.8 | >10000 |
| 91 | 16.3 | 991 |
| 92 | 36.7 | 3133 |
| 93 | 46.4 | 3200 |
| 94 | 24.4 | 2158 |
| 95 | 17.8 | 2308 |
| 96 | 60.0 | >10000 |
| 97 | 123.7 | 6625 |
| 98 | 28.8 | 3101 |
| 99 | 42.3 | 8102 |
| 100 | 95.8 | >10000 |
| 101 | 38.5 | 9263 |
| 102 | 14.0 | 9245 |
| 103 | 23.5 | 2436 |
| 104 | 60.0 | 9140 |
| 105 | 27.6 | 7261 |
| 106 | 177.7 | >10000 |

The compounds of the examples possess greater selectivity for the orexin-2 receptor than for the orexin-1 receptor. As indicated by the data herein, the compounds of the present examples provide greater functional selectivity for the orexin-2 receptor over the orexin-1 receptor. The distinction in potency between the orexin-2 receptor and the orexin-1 receptor in the whole cell FLIPR functional assay provides enhanced predictive value for determining in vivo efficacy. Increasing the functional selectivity for the orexin-2 receptor reduces the potential for dual receptor antagonism in vivo. Such greater functional selectivity may provide benefits over other orexin receptor antagonists that are known in the art.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

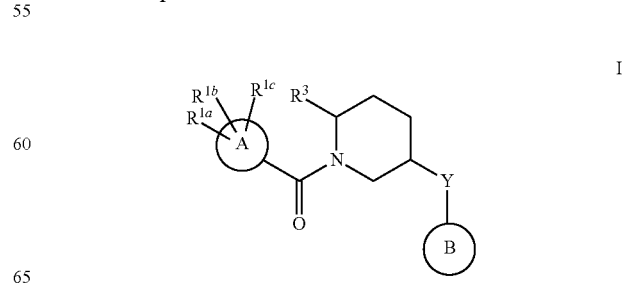

wherein:

A is selected from the group consisting of phenyl, naphthyl and heteroaryl;

B is selected from the group consisting of:

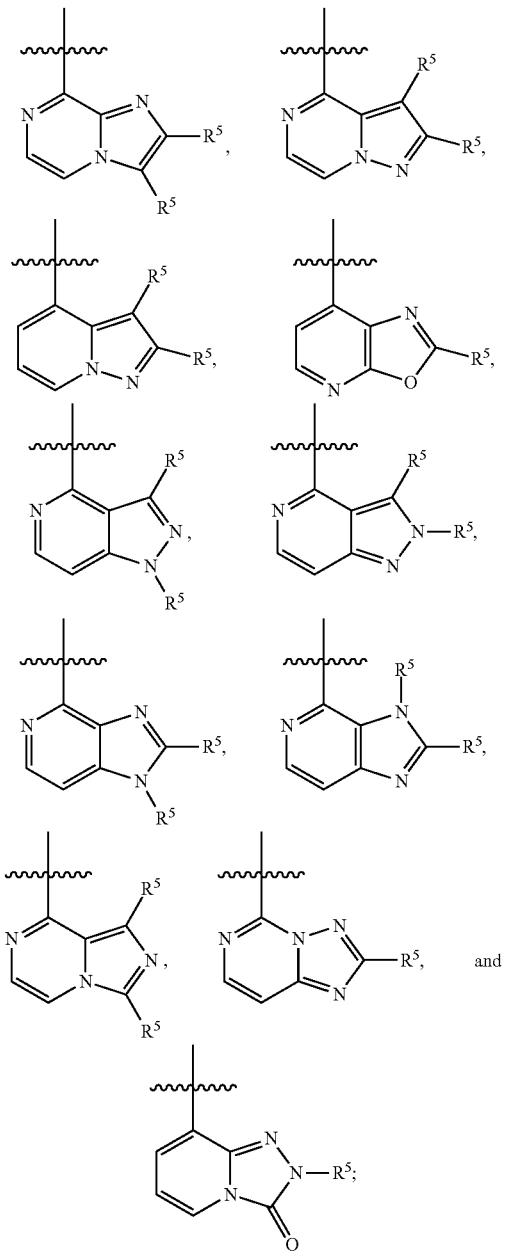

Y is O, S or NH;

each of $R^{1a}$, $R^{1b}$ and $R^{1c}$ is independently selected from the group consisting of:
(1) hydrogen,
(2) halogen,
(3) hydroxyl,
(4) —$(CH_2)_s$-$(C=O)_m$—$O_n$—$C_{1-6}$alkyl, and where the alkyl is unsubstituted or substituted with one or more substituents selected from $R^4$,
(5) —$(CH_2)_s$-$(C=O)_m$—$O_n$—$C_{3-6}$cycloalkyl, where the cycloalkyl is unsubstituted or substituted with one or more substituents selected from $R^4$,
(6) —$(CH_2)_s$-$(C=O)_m$—$C_{2-4}$alkenyl, where the alkenyl is unsubstituted or substituted with one or more substituents selected from $R^4$,
(7) —$(CH_2)_s$-$(C=O)_m$—$C_{2-4}$alkynyl, where the alkynyl is unsubstituted or substituted with one or more substituents selected from $R^4$,
(8) —$(CH_2)_s$-$(C=O)_m$—$O_n$-phenyl or —$(CH_2)_s$-$(C=O)_m$—$O_n$-naphthyl, where the phenyl or naphthyl is unsubstituted or substituted with one or more substituents selected from $R^4$,
(9) —$(CH_2)_s$-$(C=O)_m$—$O_n$—X, wherein X is heterocyclyl or heteroaryl, wherein the heterocyclyl or heteroaryl is unsubstituted or substituted with one or more substituents selected from $R^4$,
(10) —$(CH_2)_s$-$(C=O)_m$—$NR^{10}R^{11}$,
(11) —$(CH_2)_s$-$S(O)_2$—$NR^{10}OR^{11}$,
(12) —$(CH_2)_s$-$S(O)_q$—$R^{12}$, where q is 0, 1 or 2 and where $R^{12}$ is selected from the definitions of $R^{10}$ and $R^{11}$,
(13) —$CO_2H$,
(14) —CN, and
(15) —$NO_2$;
where m is 0 or 1, n is 0 or 1 (wherein if m is 0 or n is 0, a bond is present), and
s is independently 0, 1, 2 or 3;

$R^3$ is selected from hydrogen, $C_{1-6}$alkyl and $C_{3-6}$cycloalkyl, wherein the alkyl or cycloalkyl is unsubstituted or substituted with one or more substituents selected from $R^4$;

$R^4$ is independently selected from the group consisting of:
(1) hydroxyl,
(2) halogen,
(3) $C_{1-6}$alkyl,
(4) —$C_{3-6}$cycloalkyl,
(5) —O—$C_{1-6}$alkyl,
(6) —O(C=O)—$C_{1-6}$alkyl,
(7) —$NH_2$,
(7) —NH—$C_{1-6}$alkyl,
(8) —$NO_2$,
(9) phenyl,
(10) heterocyclyl,
(11) —$CO_2H$, and
(12) —CN;

$R^5$ is independently selected from the group consisting of:
hydrogen, halogen, OH, $NH_2$, CN, $C_1$-$C_6$alkylOR$^6$, —O(C=O)—$C_{1-6}$alkyl, —(C=O)—$NR^6_2$, $C_{1-6}$alkyl, $C_{1-6}$alkenyl, $C_3$-$C_8$cycloalkyl, wherein the alkyl, alkenyl or cycloalkyl is optionally substituted with one or more moieties selected from the group consisting of halogen, OH and $NH_2$;

$R^6$ is independently hydrogen or $C_{1-6}$alkyl;

$R^{10}$ and $R^{11}$ are independently selected from the group consisting of:
(a) hydrogen,
(b) $C_{1-6}$alkyl, which is unsubstituted or substituted with $R^4$,
(c) $C_{3-6}$alkenyl, which is unsubstituted or substituted with $R^4$,
(d) $C_{3-6}$alkynyl, which is unsubstituted or substituted with $R^4$,
(e) $C_{3-6}$cycloalkyl which is unsubstituted or substituted with $R^4$,
(f) phenyl, which is unsubstituted or substituted with $R^4$, and
(g) heterocyclyl, which is unsubstituted or substituted with $R^4$, or a pharmaceutically acceptable salt thereof.

2. The compound of claim 1 or a pharmaceutically acceptable salt thereof, of the formula Ia:

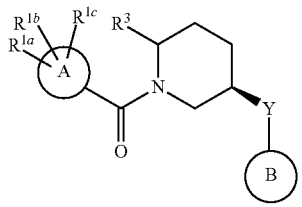

wherein
A is selected from the group consisting of phenyl, thienyl, pyridyl and pyrimidinyl;
Y is O, S or NH;
$R^{1a}$ and $R^{1b}$ are both H, $R^{1c}$ is selected from the group consisting of:
(1) hydrogen,
(2) halogen,
(3) hydroxyl,
(4) —$(CH_2)_s$-(C=O)$_m$—O$_n$—$C_{1-6}$alkyl, and where the alkyl is unsubstituted or substituted with one or more substituents selected from $R^4$,
(5) —$(CH_2)_s$-O$_n$—$C_{3-6}$cycloalkyl, where the cycloalkyl is unsubstituted or substituted with one or more substituents selected from $R^4$,
(6) -phenyl, where the phenyl is unsubstituted or substituted with one or more substituents selected from $R^4$,
(7) -heteroaryl selected from the group consisting of triazolyl, pyrimidinyl, tetrazolyl, pyrazolyl and pyridinyl, where the heteroaryl is unsubstituted or substituted with one or more substituents selected from $R^4$,
(8) —$(CH_2)_s$-S(O)$_q$—$R^{12}$, where q is 0, 1 or 2 and where $R^{12}$ is selected from
(a) $C_{1-6}$alkyl, which is unsubstituted or substituted with $R^4$,
(b) $C_{3-6}$alkenyl, which is unsubstituted or substituted with $R^4$,
(c) $C_{3-6}$alkynyl, which is unsubstituted or substituted with $R^4$,
n is 0 or 1, m is 0 or 1, (wherein if m is 0 or n is 0, a bond is present)
s is independently 0, 1, 2 or 3;
$R^3$ is selected from hydrogen or $C_{1-6}$alkyl, which is unsubstituted or substituted with one or more substituents selected from $R^4$;
$R^4$ is independently selected from the group consisting of:
(1) hydroxyl,
(2) halogen,
(3) $C_{1-6}$alkyl,
(4) —$NH_2$,
(5) —NH—$C_{1-6}$alkyl,
(6) —$NO_2$, and
(7) —CN;
$R^5$ is independently selected from the group consisting of: hydrogen, halogen, OH, $NH_2$, CN, $C_1$-$C_6$alkylOR$^6$, and $C_{1-6}$alkyl, wherein the alkyl is optionally substituted with one or more moieties selected from the group consisting of halogen, OH and $NH_2$;
$R^6$ is hydrogen or $C_{1-6}$alkyl;
or a pharmaceutically acceptable salt thereof.

3. The compound of claim 1 or a pharmaceutically acceptable salt thereof, wherein
B is:

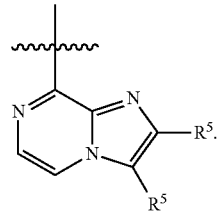

4. The compound of claim 1 or a pharmaceutically acceptable salt thereof wherein $R^3$ is methyl.

5. The compound of claim 1 or a pharmaceutically acceptable salt thereof, of the formula Ib:

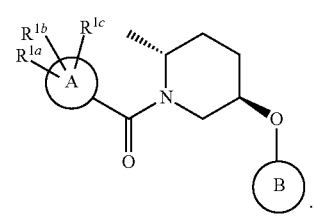

6. The compound of claim 1 or a pharmaceutically acceptable salt thereof wherein $R^5$ is selected from the group consisting of: halogen, CN, methyl, fluoro-methyl, difluoro-methyl, and trifluoro-methyl.

7. A compound which is selected from the group consisting of:
(2-(2H-1,2,3-triazol-2-yl)phenyl)((2R,5R)-5-(imidazo[1,2-a]pyrazin-8-yloxy)-2-methylpiperidin-1-yl)methanone;
((2R,5R)-5-(imidazo[1,2-a]pyrazin-8-yloxy)-2-methylpiperidin-1-yl)(2-((methylsulfonyl)methyl)phenyl)methanone;
((2R,5R)-5-(imidazo[1,2-a]pyrazin-8-yloxy)-2-methylpiperidin-1-yl)(2-(2,2,2-trifluoroethyl)phenyl)methanone;
((2R,5R)-5-(imidazo[1,2-a]pyrazin-8-yloxy)-2-methylpiperidin-1-yl)(2-propylphenyl)methanone;
(2-(2H-1,2,3-triazol-2-yl)phenyl)((2R,5R)-5-(imidazo[1,2-a]pyrazin-8-ylthio)-2-methylpiperidin-1-yl)methanone;
(2-(2H-1,2,3-triazol-2-yl)phenyl)((2R,5R)-2-methyl-5-((2-methylimidazo[1,2-a]pyrazin-8-yl)oxy)piperidin-1-yl)methanone;
(2-(2H-1,2,3-triazol-2-yl)thiophen-3-yl)((2R,5R)-2-methyl-5-((2-methylimidazo[1,2-a]pyrazin-8-yl)oxy)piperidin-1-yl)methanone;
(4-(2H-1,2,3-triazol-2-yl)thiophen-3-yl)((2R,5R)-2-methyl-5-((2-methylimidazo[1,2-a]pyrazin-8-yl)oxy)piperidin-1-yl)methanone;
1-(2-((2R,5R)-2-methyl-5-((2-methylimidazo[1,2-a]pyrazin-8-yl)oxy)piperidine-1-carbonyl)phenyl)cyclopropanecarbonitrile;
(4-fluoro-2-(2H-1,2,3-triazol-2-yl)phenyl)((2R,5R)-2-methyl-5-((2-methylimidazo[1,2-a]pyrazin-8-yl)oxy)piperidin-1-yl)methanone;

(2-(2H-tetrazol-2-yl)phenyl)((2R,5R)-2-methyl-5-((2-methylimidazo[1,2-a]pyrazin-8-yl)oxy)piperidin-1-yl)methanone;

((2R,5R)-2-methyl-5-((2-methylimidazo[1,2-a]pyrazin-8-yl)oxy)piperidin-1-yl)(2-((methylsulfonyl)methyl)phenyl)methanone;

((2R,5R)-2-methyl-5-((2-methylimidazo[1,2-a]pyrazin-8-yl)oxy)piperidin-1-yl)(4-(pyrimidin-2-yl)thiophen-3-yl)methanone;

((2R,5R)-2-methyl-5-((2-methylimidazo[1,2-a]pyrazin-8-yl)oxy)piperidin-1-yl)(2-(pyrimidin-2-yl)thiophen-3-yl)methanone;

(2-(2,2-difluoroethoxy)pyridin-3-yl)((2R,5R)-2-methyl-5-((2-methylimidazo[1,2-a]pyrazin-8-yl)oxy)piperidin-1-yl)methanone;

((2R,5R)-2-methyl-5-((2-methylimidazo[1,2-a]pyrazin-8-yl)oxy)piperidin-1-yl)(2-(2,2,2-trifluoroethoxy)pyridin-3-yl)methanone;

((2R,5R)-2-methyl-5-((2-methylimidazo[1,2-a]pyrazin-8-yl)oxy)piperidin-1-yl)(2-phenylpyridin-3-yl)methanone;

(2-(1H-pyrazol-1-yl)pyridin-3-yl)((2R,5R)-2-methyl-5-((2-methylimidazo[1,2-a]pyrazin-8-yl)oxy)piperidin-1-yl)methanone;

(2-(2H-1,2,3-triazol-2-yl)phenyl)((2R,5R)-2-methyl-5-((2-methylimidazo[1,2-a]pyrazin-8-yl)amino)piperidin-1-yl)methanone;

(2-(2H-1,2,3-triazol-2-yl)phenyl)((2R,5R)-5-((2-isopropylimidazo[1,2-a]pyrazin-8-yl)oxy)-2-methylpiperidin-1-yl)methanone;

(2-(2H-1,2,3-triazol-2-yl)phenyl)((2R,5R)-2-methyl-5-((2-(trifluoromethyl)imidazo[1,2-a]pyrazin-8-yl)oxy)piperidin-1-yl)methanone;

(2-(2H-1,2,3-triazol-2-yl)phenyl)((2R,5R)-2-methyl-5-((2-(trifluoromethyl)imidazo[1,2-a]pyrazin-8-yl)amino)piperidin-1-yl)methanone;

(2-(2H-1,2,3-triazol-2-yl)thiophen-3-yl)((2R,5R)-2-methyl-5-((2-(trifluoromethyl)imidazo[1,2-a]pyrazin-8-yl)amino)piperidin-1-yl)methanone;

8-(((3R,6R)-1-(2-(2H-1,2,3-triazol-2-yl)benzoyl)-6-methylpiperidin-3-yl)oxy)imidazo[1,2-a]pyrazine-2-carbonitrile;

(2-(2H-1,2,3-triazol-2-yl)phenyl)((2R,5R)-5-((2-(hydroxymethyl)imidazo[1,2-a]pyrazin-8-yl)oxy)-2-methylpiperidin-1-yl)methanone;

(2-(2H-1,2,3-triazol-2-yl)phenyl)((2R,5R)-5-((3-chloroimidazo[1,2-a]pyrazin-8-yl)oxy)-2-methylpiperidin-1-yl)methanone;

(2-(2H-tetrazol-2-yl)phenyl)((2R,5R)-5-((3-chloroimidazo[1,2-a]pyrazin-8-yl)oxy)-2-methylpiperidin-1-yl)methanone;

1-(2-((2R,5R)-5-((3-chloroimidazo[1,2-a]pyrazin-8-yl)oxy)-2-methylpiperidine-1-carbonyl)phenyl)cyclopropanecarbonitrile;

(2-(2H-1,2,3-triazol-2-yl)thiophen-3-yl)((2R,5R)-5-((3-chloroimidazo[1,2-a]pyrazin-8-yl)oxy)-2-methylpiperidin-1-yl)methanone;

(2-(2H-1,2,3-triazol-2-yl)phenyl)((2R,5R)-5-((3-chloroimidazo[1,2-a]pyrazin-8-yl)amino)-2-methylpiperidin-1-yl)methanone;

((2R,5R)-5-((3-chloroimidazo[1,2-a]pyrazin-8-yl)amino)-2-methylpiperidin-1-yl)(2-(pyrimidin-2-yl)phenyl)methanone;

(2-(2H-1,2,3-triazol-2-yl)phenyl)((2R,5R)-5-((3-fluoroimidazo[1,2-a]pyrazin-8-yl)oxy)-2-methylpiperidin-1-yl)methanone;

(2-(2H-1,2,3-triazol-2-yl)phenyl)((2R,5R)-5-((3-bromoimidazo[1,2-a]pyrazin-8-yl)oxy)-2-methylpiperidin-1-yl)methanone;

(2-(2H-1,2,3-triazol-2-yl)phenyl)((2R,5R)-2-methyl-5-((3-methylimidazo[1,2-a]pyrazin-8-yl)oxy)piperidin-1-yl)methanone;

8-(((3R,6R)-1-(2-(2H-1,2,3-triazol-2-yl)benzoyl)-6-methylpiperidin-3-yl)oxy)imidazo[1,2-a]pyrazine-3-carbonitrile;

(2-(2H-1,2,3-triazol-2-yl)phenyl)((2R,5R)-2-methyl-5-((3-vinylimidazo[1,2-a]pyrazin-8-yl)oxy)piperidin-1-yl)methanone;

(2-(2H-1,2,3-triazol-2-yl)phenyl)((2R,5R)-5-((3-ethylimidazo[1,2-a]pyrazin-8-yl)oxy)-2-methylpiperidin-1-yl)methanone;

(2-(2H-1,2,3-triazol-2-yl)phenyl)((2R,5R)-5-((3-(difluoromethyl)imidazo[1,2-a]pyrazin-8-yl)oxy)-2-methylpiperidin-1-yl)methanone;

((2R,5R)-5-((3-(difluoromethyl)imidazo[1,2-a]pyrazin-8-yl)oxy)-2-methylpiperidin-1-yl)(2-((methylsulfonyl)methyl)phenyl)methanone;

(2-(2H-1,2,3-triazol-2-yl)thiophen-3-yl)((2R,5R)-5-((3-(difluoromethyl)imidazo[1,2-a]pyrazin-8-yl)oxy)-2-methylpiperidin-1-yl)methanone;

(4-(2H-1,2,3-triazol-2-yl)thiophen-3-yl)((2R,5R)-5-((3-(difluoromethyl)imidazo[1,2-a]pyrazin-8-yl)oxy)-2-methylpiperidin-1-yl)methanone;

1-(2-((2R,5R)-5-((3-(difluoromethyl)imidazo[1,2-a]pyrazin-8-yl)oxy)-2-methylpiperidine-1-carbonyl)phenyl)cyclopropanecarbonitrile;

((2R,5R)-5-((3-(difluoromethyl)imidazo[1,2-a]pyrazin-8-yl)oxy)-2-methylpiperidin-1-yl)(4-fluoro-2-(2H-1,2,3-triazol-2-yl)phenyl)methanone;

(2-(2H-tetrazol-2-yl)phenyl)((2R,5R)-5-((3-(difluoromethyl)imidazo[1,2-a]pyrazin-8-yl)oxy)-2-methylpiperidin-1-yl)methanone;

((2R,5R)-5-((3-(difluoromethyl)imidazo[1,2-a]pyrazin-8-yl)oxy)-2-methylpiperidin-1-yl)(2-(methoxymethyl)phenyl)methanone;

(3-(1H-pyrazol-1-yl)pyrazin-2-yl)((2R,5R)-5-((3-(difluoromethyl)imidazo[1,2-a]pyrazin-8-yl)oxy)-2-methylpiperidin-1-yl)methanone;

((2R,5R)-5-((3-(difluoromethyl)imidazo[1,2-a]pyrazin-8-yl)oxy)-2-methylpiperidin-1-yl)(3-(pyridin-2-yl)pyrazin-2-yl)methanone;

methyl 2-((2R,5R)-5-((3-(difluoromethyl)imidazo[1,2-a]pyrazin-8-yl)oxy)-2-methylpiperidine-1-carbonyl)benzoate;

((2R,5R)-5-((3-(difluoromethyl)imidazo[1,2-a]pyrazin-8-yl)oxy)-2-methylpiperidin-1-yl)(3-phenylpyridin-2-yl)methanone;

((2R,5R)-5-((3-(difluoromethyl)imidazo[1,2-a]pyrazin-8-yl)oxy)-2-methylpiperidin-1-yl)(2-(2,2,2-trifluoroethoxy)pyridin-3-yl)methanone;

(2-(2,2-difluoroethoxy)pyridin-3-yl)((2R,5R)-5-((3-(difluoromethyl)imidazo[1,2-a]pyrazin-8-yl)oxy)-2-methylpiperidin-1-yl)methanone;

(2-(1H-pyrazol-1-yl)pyridin-3-yl)((2R,5R)-5-((3-(difluoromethyl)imidazo[1,2-a]pyrazin-8-yl)oxy)-2-methylpiperidin-1-yl)methanone;

((2R,5R)-5-((3-(difluoromethyl)imidazo[1,2-a]pyrazin-8-yl)oxy)-2-methylpiperidin-1-yl)(2-(pyrazin-2-yl)phenyl)methanone;

((2R,5R)-5-((3-(difluoromethyl)imidazo[1,2-a]pyrazin-8-yl)oxy)-2-methylpiperidin-1-yl)(2-(pyrimidin-2-yl)phenyl)methanone;

((2R,5R)-5-((3-(difluoromethyl)imidazo[1,2-a]pyrazin-8-yl)oxy)-2-methylpiperidin-1-yl)(4-(pyrimidin-2-yl)thiophen-3-yl)methanone;

((2R,5R)-5-((3-(difluoromethyl)imidazo[1,2-a]pyrazin-8-yl)oxy)-2-methylpiperidin-1-yl)(2-(pyrimidin-2-yl)thiophen-3-yl)methanone;

(2-(2H-1,2,3-triazol-2-yl)phenyl)((2R,5R)-2-methyl-5-((3-(trifluoromethyl)imidazo[1,2-a]pyrazin-8-yl)oxy)piperidin-1-yl)methanone;

(2-(2H-1,2,3-triazol-2-yl)thiophen-3-yl)((2R,5R)-2-methyl-5-((3-(trifluoromethyl)imidazo[1,2-a]pyrazin-8-yl)oxy)piperidin-1-yl)methanone;

1-(2-((2R,5R)-2-methyl-5-((3-(trifluoromethyl)imidazo[1,2-a]pyrazin-8-yl)oxy)piperidine-1-carbonyl)phenyl)cyclopropanecarbonitrile;

(2-(2H-tetrazol-2-yl)phenyl)((2R,5R)-2-methyl-5-((3-(trifluoromethyl)imidazo[1,2-a]pyrazin-8-yl)oxy)piperidin-1-yl)methanone;

((2R,5R)-2-methyl-5-((3-(trifluoromethyl)imidazo[1,2-a]pyrazin-8-yl)oxy)piperidin-1-yl)(2-((methyl sulfonyl)methyl)phenyl)methanone;

((2R,5R)-2-methyl-5-((3-(trifluoromethyl)imidazo [1,2-a]pyrazin-8-yl)oxy)piperidin-1-yl)(3-phenylpyridin-2-yl)methanone;

((2R,5R)-2-methyl-5-((3-(trifluoromethyl)imidazo[1,2-a]pyrazin-8-yl)oxy)piperidin-1-yl)(2-(2,2,2-trifluoroethoxy)pyridin-3-yl)methanone;

(2-(2,2-difluoroethoxy)pyridin-3-yl)((2R,5R)-2-methyl-5-((3-(trifluoromethyl)imidazo[1,2-a]pyrazin-8-yl)oxy)piperidin-1-yl)methanone;

(2-(1H-pyrazol-1-yl)pyridin-3-yl)((2R,5R)-2-methyl-5-((3-(trifluoromethyl)imidazo[1,2-a]pyrazin-8-yl)oxy)piperidin-1-yl)methanone;

((2R,5R)-2-methyl-5-((3-(trifluoromethyl)imidazo[1,2-a]pyrazin-8-yl)oxy)piperidin-1-yl)(2-(pyrimidin-2-yl)phenyl)methanone;

(2-(2H-1,2,3-triazol-2-yl)phenyl)((2R,5R)-5-((3-(2,2-difluoro-1-hydroxyethyl)imidazo[1,2-a]pyrazin-8-yl)oxy)-2-methylpiperidin-1-yl)methanone;

(2-(2H-1,2,3-triazol-2-yl)phenyl)((2R,5R)-5-((3-(1-hydroxyethyl)imidazo[1,2-a]pyrazin-8-yl)oxy)-2-methylpiperidin-1-yl)methanone;

(2-(2H-1,2,3-triazol-2-yl)phenyl)((2R,5R)-2-methyl-5-(pyrazolo[1,5-a]pyrazin-4-yloxy)piperidin-1-yl)methanone;

(2-(2H-1,2,3-triazol-2-yl)thiophen-3-yl)((2R,5R)-2-methyl-5-(pyrazolo[1,5-a]pyrazin-4-yloxy)piperidin-1-yl)methanone;

(4-(2H-1,2,3-triazol-2-yl)thiophen-3-yl)((2R,5R)-2-methyl-5-(pyrazolo[1,5-a]pyrazin-4-yloxy)piperidin-1-yl)methanone;

1-(2-((2R,5R)-2-methyl-5-(pyrazolo[1,5-a]pyrazin-4-yloxy)piperidine-1-carbonyl)phenyl)cyclopropanecarbonitrile;

(4-fluoro-2-(2H-1,2,3-triazol-2-yl)phenyl)((2R,5R)-2-methyl-5-(pyrazolo[1,5-a]pyrazin-4-yloxy)piperidin-1-yl)methanone;

((2R,5R)-2-methyl-5-(pyrazolo[1,5-a]pyrazin-4-yloxy)piperidin-1-yl)(4-(pyrimidin-2-yl)thiophen-3-yl)methanone;

((2R,5R)-2-methyl-5-(pyrazolo[1,5-a]pyrazin-4-yloxy)piperidin-1-yl)(2-(pyrimidin-2-yl)thiophen-3-yl)methanone;

(2-(2H-tetrazol-2-yl)phenyl)((2R,5R)-2-methyl-5-(pyrazolo[1,5-a]pyrazin-4-yloxy)piperidin-1-yl)methanone;

((2R,5R)-5-(imidazo[1,2-a]pyrazin-8-yloxy)-2-methylpiperidin-1-yl)(2-((methylsulfonyl)methyl)phenyl)methanone;

((2R,5R)-2-methyl-5-(pyrazolo[1,5-a]pyrazin-4-yloxy)piperidin-1-yl)(3-(pyridin-2-yl)pyrazin-2-yl)methanone;

methyl 2-((2R,5R)-2-methyl-5-(pyrazolo[1,5-a]pyrazin-4-yloxy)piperidine-1-carbonyl)benzoate;

(3-(1H-pyrazol-1-yl)pyrazin-2-yl)((2R,5R)-2-methyl-5-(pyrazolo[1,5-a]pyrazin-4-yloxy)piperidin-1-yl)methanone;

(2-ethoxyphenyl)((2R,5R)-2-methyl-5-(pyrazolo[1,5-a]pyrazin-4-yloxy)piperidin-1-yl)methanone;

((2R,5R)-2-methyl-5-(pyrazolo[1,5-a]pyrazin-4-yloxy)piperidin-1-yl)(2-propylphenyl)methanone;

(2-isopropoxypyridin-3-yl)((2R,5R)-2-methyl-5-(pyrazolo[1,5-a]pyrazin-4-yloxy)piperidin-1-yl)methanone;

(2-isopropoxyphenyl)((2R,5R)-2-methyl-5-(pyrazolo[1,5-a]pyrazin-4-yloxy)piperidin-1-yl)methanone;

((2R,5R)-2-methyl-5-(pyrazolo[1,5-a]pyrazin-4-yloxy)piperidin-1-yl)(2-(pyrimidin-2-yl)phenyl)methanone;

(2-(2H-1,2,3-triazol-2-yl)phenyl)((2R,5R)-2-methyl-5-(pyrazolo[1,5-a]pyrazin-4-ylamino)piperidin-1-yl)methanone;

(2-(2H-1,2,3-triazol-2-yl)phenyl)((2R,5R)-2-methyl-5-(pyrazolo[1,5-a]pyrazin-4-ylthio)piperidin-1-yl)methanone;

(2-(2H-1,2,3-triazol-2-yl)phenyl)((2R,5R)-5-((3-bromopyrazolo[1,5-a]pyrazin-4-yl)oxy)-2-methylpiperidin-1-yl)methanone;

(2-(2H-1,2,3-triazol-2-yl)phenyl)((2R,5R)-2-methyl-5-((3-methylpyrazolo[1,5-a]pyrazin-4-yl)oxy)piperidin-1-yl)methanone;

(2-(2H-1,2,3-triazol-2-yl)phenyl)((2R,5R)-2-methyl-5-(pyrazolo[1,5-a]pyridin-4-yloxy)piperidin-1-yl)methanone;

(2-(2H-1,2,3-triazol-2-yl)phenyl)((2R,5R)-2-methyl-5-(oxazolo[5,4-b]pyridin-7-yloxy)piperidin-1-yl)methanone;

(2-(2H-tetrazol-2-yl)phenyl)((2R,5R)-2-methyl-5-(oxazolo[5,4-b]pyridin-7-yloxy)piperidin-1-yl)methanone;

methyl 2-((2R,5R)-2-methyl-5-(oxazolo[5,4-b]pyridin-7-yloxy)piperidine-1-carbonyl)benzoate;

(2-ethoxyphenyl)((2R,5R)-2-methyl-5-(oxazolo[5,4-b]pyridin-7-yloxy)piperidin-1-yl)methanone;

(2-(2H-1,2,3-triazol-2-yl)phenyl)((2R,5R)-2-methyl-5-((1-methyl-1H-pyrazolo[4,3-c]pyridin-4-yl)oxy)piperidin-1-yl)methanone;

(2-(2H-1,2,3-triazol-2-yl)phenyl)((2R,5R)-2-methyl-5-((1-methyl-1H-pyrazolo[4,3-c]pyridin-4-yl)amino)piperidin-1-yl)methanone;

(2-(2H-1,2,3-triazol-2-yl)phenyl)((2R,5R)-2-methyl-5-((2-methy-2H-pyrazolo[4,3-c]pyridin-4-yl)amino)piperidin-1-yl)methanone;

(2-(2H-1,2,3-triazol-2-yl)phenyl)((2R,5R)-2-methyl-5-((1-methyl-1H-imidazo[4,5-c]pyridin-4-yl)oxy)piperidin-1-yl)methanone;

(2-(2H-1,2,3-triazol-2-yl)phenyl)((2R,5R)-2-methyl-5-((3-methyl-3H-imidazo[4,5-c]pyridin-4-yl)oxy)piperidin-1-yl)methanone;

(2-(2H-1,2,3-triazol-2-yl)phenyl)((2R,5R)-2-methyl-5-((3-methyl-3H-imidazo[4,5-c]pyridin-4-yl)amino)piperidin-1-yl)methanone;

(2-(2H-1,2,3-triazol-2-yl)phenyl)((2R,5R)-2-methyl-5-((1-methyl-1H-imidazo[4,5-c]pyridin-4-yl)amino)piperidin-1-yl)methanone;

(2-(2H-1,2,3-triazol-2-yl)phenyl)((2R,5R)-5-(imidazo[1,5-a]pyrazin-8-yloxy)-2-methylpiperidin-1-yl)methanone;

(2-(2H-1,2,3-triazol-2-yl)phenyl)((2R,5R)-2-methyl-5-((3-methylimidazo[1,5-a]pyrazin-8-yl)oxy)piperidin-1-yl)methanone;

(2-(2H-1,2,3-triazol-2-yl)phenyl)((2R,5R)-2-methyl-5-((2-methyl-[1,2,4]triazolo[1,5-c]pyrimidin-5-yl)oxy)piperidin-1-yl)methanone;

(2-(2H-1,2,3-triazol-2-yl)phenyl)((2R,5R)-2-methyl-5-((2-methyl-[1,2,4]triazolo[1,5-c]pyrimidin-5-yl)amino)piperidin-1-yl)methanone; and 8-(((3R,6R)-1-(2-(2H-1,2,3-triazol-2-yl)benzoyl)-6-methylpiperidin-3-yl)oxy)-2-methyl-[1,2,4]triazolo[4,3-a]pyridin-3(2H)-one;

or pharmaceutically acceptable salt thereof.

8. A pharmaceutical composition which comprises an inert carrier and a compound of claim 1 or a pharmaceutically acceptable salt thereof.

9. A method for enhancing the quality of sleep in a mammalian patient in need thereof which comprises administering to the patient a therapeutically effective amount of the compound of claim 1 or a pharmaceutically acceptable salt thereof.

* * * * *